US007705041B2

(12) United States Patent
Michelet et al.

(10) Patent No.: US 7,705,041 B2
(45) Date of Patent: Apr. 27, 2010

(54) INHIBITORS OF 15-HYDROXYPROSTAGLANDIN DEHYDROGENASE FOR STIMULATING PIGMENTATION OF THE SKIN OR SKIN APPENDAGES

(75) Inventors: Jean-Francois Michelet, Creteil (FR); Stephane Commo, Paris (FR)

(73) Assignee: L'Oreal, Paris (FR)

( * ) Notice: Subject to any disclaimer, the term of this patent is extended or adjusted under 35 U.S.C. 154(b) by 1003 days.

(21) Appl. No.: 11/202,192

(22) Filed: Aug. 12, 2005

(65) Prior Publication Data
US 2006/0034786 A1    Feb. 16, 2006

Related U.S. Application Data

(63) Continuation of application No. PCT/FR2004/000325, filed on Feb. 12, 2004.

(60) Provisional application No. 60/456,563, filed on Mar. 28, 2003.

(51) Int. Cl.
*A01N 43/02* (2006.01)
*A01N 43/08* (2006.01)
*A01N 43/10* (2006.01)

(52) U.S. Cl. .................................... 514/461
(58) Field of Classification Search ........ 514/381, 514/461
See application file for complete search history.

(56) References Cited

U.S. PATENT DOCUMENTS 5,514,374 A * 5/1996 Bonte et al. ............... 424/745
5,653,983 A * 8/1997 Meybeck et al. ........... 424/745
5,965,157 A * 10/1999 Li et al. .................... 424/450
6,103,765 A    8/2000 Neal
6,267,948 B1    7/2001 Ren et al.
6,414,027 B1 * 7/2002 Neal ......................... 514/573
6,486,147 B2 * 11/2002 Baldo et al. ............... 514/178
7,294,641 B2    11/2007 Boulle et al.
2005/0042674 A9    2/2005 Yu et al.

FOREIGN PATENT DOCUMENTS

| EP | 0884045 | 12/1998 |
| EP | 1145705 | 10/2001 |
| WO | WO 96/25943 | 8/1996 |
| WO | WO 99/51198 | 10/1999 |
| WO | WO 01/17479 | 3/2001 |
| WO | WO 03/072033 | 9/2003 |

OTHER PUBLICATIONS

Huang et. al., American Journal of Clinical Dermatology, 2002 3(5):301-308.*
Haider et al., Dermatologic Therapy, 2001, vol. 14, issue 1, pp. 1-6.*
Kung-Chao et al., Biochim Biophys Acta, Jul. 10, 1980, 614(1):abstract.*

* cited by examiner

*Primary Examiner*—Sreeni Padmanabhan
*Assistant Examiner*—Courtney Brown
(74) *Attorney, Agent, or Firm*—Buchanan, Ingersoll & Rooney P.C.

(57) ABSTRACT

Inhibitors of 15-hydroxyprostaglandin dehydrogenase (15-PGDH), for example tetrazole, styrylpyrazole, phenylfuran, phenylthiophene, phenylpyrrazole, pyrazolecarboxamide, 2-thioacetamide and azo compounds, are useful for promoting or stimulating pigmentation of the skin and/or skin appendages and/or for preventing and/or for limiting depigmentation and/or whitening of the skin and/or skin appendages, notably for preventing and/or limiting canities.

25 Claims, 2 Drawing Sheets

Figure 1:
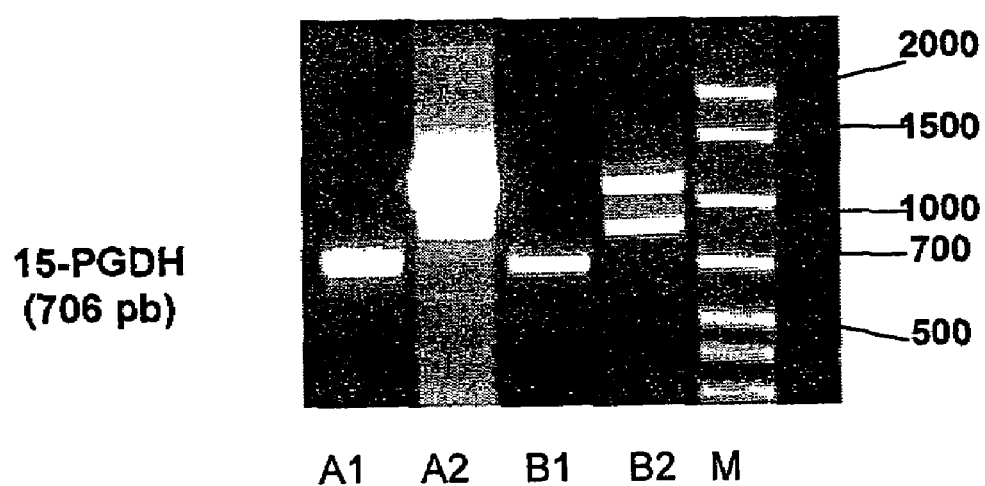

INHIBITORS OF 15-HYDROXYPROSTAGLANDIN DEHYDROGENASE FOR STIMULATING PIGMENTATION OF THE SKIN OR SKIN APPENDAGES

CROSS-REFERENCE TO PRIORITY/PCT/PROVISIONAL APPLICATIONS

This application claims priority under 35 U.S.C. §119 of FR 03/50023, filed Feb. 12, 2003, and of provisional application Ser. No. 60/456,563, filed Mar. 24, 2003, and is a continuation of PCT/FR 2004/000325, filed Feb. 12, 2004 and designating the United States (published in the French language on Sep. 2, 2004 as WO 2004/073594 A2; the title and abstract were also published in English), each hereby expressly incorporated by reference and each assigned to the assignee hereof.

BACKGROUND OF THE INVENTION

1. Technical Field of the Invention

The present invention relates to a cosmetic regime or regimen for promoting pigmentation of the skin and/or skin appendages, in particular of the hair and/or of body hair, and to the formulation of 15-hydroxyprostaglandin dehydrogenase inhibitors into compositions suited to combat canities. This invention relates in particular to the administration of tetrazole, styrylpyrazole, phenylfuran, phenylthiophene, phenylpyrrazole, pyrazolecarboxamide, 2-thioacetamide or azo compounds as agents for promoting pigmentation of the skin and/or skin appendages, and/or for limiting and/or preventing depigmentation.

2. Description of Background and/or Related and/or Prior Art

The color of the hair and of the human skin depends on various factors, and in particular on the seasons of the year, on race, on sex and on age. It is mainly determined by the concentration of melanin produced by melanocytes. Melanocytes are specialized cells that, by means of specific organelles, melanosomes, synthesize melanin.

Melanin synthesis, or melanogenesis, is complex and involves, diagrammatically, the following main steps:

Tyrosine→Dopa→Dopaquinone→Dopachrome→Melanin

Tyrosinase (monophenol dihydroxyl phenylalanine: oxygen oxidoreductase EC 1.14.18.1) intervenes in this series of reactions by catalyzing in particular the reaction consisting of the conversion of tyrosine to Dopa (dihydroxyphenylalanine) and the reaction consisting of the conversion of Dopa to Dopaquinone.

The upper part of the hair follicle is like a tubular invagination of the epidermis that extends to the deep layers of the dermis. The lower part, or hair bulb, itself comprises an invagination in which is found the dermal papilla. Around the dermal papilla, in the lower part of the bulb, is a zone populated with highly proliferative cells (cells of the matrix). These cells are the precursors of the keratinized cells that will constitute the hair. The cells that result from the proliferation of these precursors migrate vertically into the bulb and gradually become keratinized in the upper part of the bulb, and this group of keratinized cells will form the hair shaft. The pigmentation of the hair and of the body hairs requires the presence of melanocytes in the bulb of the hair follicle. These melanocytes are in an active state, i.e., they synthesize melanins. These pigments are transmitted to the keratinocytes intended to form the hair shaft, which will result in the growth of a pigmented hair or body hair. This structure is called "follicle pigmentary unit".

It is known that, in most populations, brown coloration of the skin and the maintaining of a constant color of the hair are considerable aspirations.

It is accepted that the appearance of gray or white body hairs and/or hair, or canities, is associated with a decrease in melanin in the hair shaft. This phenomenon occurs naturally during the life of an individual. However, human beings seek to have a younger appearance and, for esthetic purposes, they often attempt to combat this phenomenon, especially when it occurs at a relatively early age.

Many solutions have thus been proposed in the field of artificial coloration through the introduction of exogenous dyes aimed at giving the hair a color that is as close as possible to its natural color. Another approach consists in stimulating the natural pigmentation pathway.

Among the solutions proposed, mention may be made of compositions containing a phosphodiesterase inhibitor (WO 95/17161), DNA fragments (WO 95/01773), diacyl glyerol (WO 94/04122), prostaglandins (WO 95/11003) or pyrimidine 3-oxide derivatives (EP 829260).

However, need continues to exist for novel solutions that are effective for promoting pigmentation of the skin, of the hair and/or of body hair, and therefore preventing or decreasing canities.

SUMMARY OF THE INVENTION

Unexpectedly, it has now been demonstrated that it is possible to stimulate melanin synthesis by melanocytes by specifically inhibiting the degradation of prostaglandins synthesized by these melanocytes or those present in its environment.

For this reason, the present invention features formulation of at least one 15-hydroxyprostaglandin dehydrogenase inhibitor into a composition or for the preparation of a composition useful to promote pigmentation of the skin or skin appendages, in particular of the hair and/or of body hair.

The involvement of certain prostaglandins in the pigmentation, in humans or in animals, of body hair or of the skin has previously been described (Wand M., 1997, *Arch. Ophthalmol.*, 115; Abdel Malek et al., 1987, *Cancer Res.*, 47).

However, prostaglandins are molecules with a very short biological half-life that act in an autocrine or paracrine manner, which reflects the local and labile nature of prostaglandin metabolism (Narumiya S et al., 1999, *Physiol Rev.*, 79(4), 1193-1226).

Surprisingly, it has now been demonstrated that an enzyme specifically involved in the degradation of these prostaglandins is expressed in the fibroblasts of the dermal papilla of the hair, which is a determining compartment for the life of the hair. Specifically, the expression of 15-hydroxyprostaglandin dehydrogenase (15-PGDH) in this region has now been shown.

Furthermore, it also has been shown, in the context of the invention, that this enzyme is also expressed in the hair melanocytes, which to date had never been demonstrated.

15-PGDH is a key enzyme in prostaglandin deactivation; 15-PGDH type 1 corresponds to the classification EC 1.1.1.141 and is NAD+ dependent. This enzyme catalyzes a reaction consisting of the oxidation, on the carbon 15, of the hydroxyl to a ketone. It was isolated from pig kidney; inhibition thereof by a thyroid hormone, triiodothyronine, at doses much higher than physiological doses, has in particular been observed. 15-PGDH type 2 is NADP dependent.

However, the presence of 15-PGDH had never been demonstrated in the dermal papilla nor in the hair melanocytes, and the use of a 15-PGDH inhibitor for promoting pigmentation of the skin, of body hair and/or of the hair had never been proposed.

In accordance with the invention, it is possible to locally regulate the amount of prostaglandins (the method of action of which is autocrine or paracrine), in particular that present in the melanocytes, in particular of the hair, by acting on the degradation catalyzed by the 15-PGDH of both the melanocytes and the fibroblasts in the dermal papilla.

It has also been shown, surprisingly, that the hair melanocytes express prostaglandin H synthase 1 (PGHS-1 or COX-1, E.C: 1.14.99.1). This demonstrates, for the first time, that hair melanocytes possess autonomous prostaglandin metabolism.

Unexpectedly, it too has been shown, in the context of the present invention, that it is possible to specifically inhibit the 15-PGDH present at the level of the dermal papilla and/or of hair melanocytes. Such inhibition therefore makes it possible to impair the deactivation of the prostaglandins in the hair melanocytes' environment. The prostaglandins can therefore continue to stimulate the melanocytes via the autocrine or paracrine pathway. In fact, the application of such inhibitors stimulates melanin production by the melanocytes.

DETAILED DESCRIPTION OF BEST MODE AND SPECIFIC/PREFERRED EMBODIMENTS OF THE INVENTION

For the purpose of the invention, the term "15-PGDH inhibitor" means any substance, simple or complex compound, of natural or synthetic origin capable of inhibiting or of decreasing the activity of the 15-PGDH enzyme, and/or capable of inhibiting, decreasing or slowing down the reaction catalyzed by this enzyme. The 15-PGDH inhibitors according to the invention are preferably inhibitors of 15-PGDH type 1.

Advantageously, the inhibitor is a specific inhibitor of NAD-dependent 15-PGDH type 1.

The term "skin appendages" means all the tegumentary additions, and in particular the nails, body hair and the hair. The term "body hair and the hair" means all the hair additions, and in particular also the eyelashes and the eyebrows.

The compositions according to the invention may be administered by any appropriate route, in particular orally, parenterally or externally topically, and their formulation will be adjusted by those skilled in the art, in particular for cosmetic or dermatological compositions. Advantageously, the compositions according to the invention are formulated for topical administration. They contain a physiologically acceptable medium, in particular a cosmetically or pharmaceutically, especially dermatologically, acceptable medium.

In a preferred embodiment, a composition according to the invention contains excipients suitable for administration to the scalp.

The present invention therefore features in particular the administration of at least one 15-PGDH inhibitor as an agent for promoting and/or inducing and/or stimulating pigmentation of the skin and/or skin appendages, and/or as an agent for preventing and/or limiting depigmentation and/or whitening of the skin and/or skin appendages, in particular as an agent for preventing and/or limiting canities; this agent is more particularly administered to mammals, in particular to humans.

According to another of its embodiments, this invention relates to the cosmetic use of at least one 15-PGDH inhibitor in a cosmetic skincare or haircare composition, for promoting and/or inducing and/or stimulating pigmentation of the skin and/or skin appendages, and/or for preventing and/or limiting depigmentation and/or whitening of the skin and/or skin appendages, and/or preventing and/or limiting canities.

The invention also relates to the use of at least one 15-PGDH inhibitor, for preparing a composition suited for promoting and/or inducing and/or stimulating pigmentation of the skin and/or skin appendages, and/or intended for preventing and/or limiting depigmentation and/or whitening of the skin and/or skin appendages, and/or intended for preventing and/or limiting canities.

The compositions suitable for implementation of the invention are in particular cosmetic and/or dermatological compositions, or pharmaceutical compositions.

The term "cosmetic composition" means in particular any substance or preparation intended to be brought into contact with the various superficial parts of the human body (epidermis, body hair and hair system, nails, lips and external genital organs) or with the teeth or the buccal mucuous membranes for the purpose, exclusively or mainly, of cleansing them, of giving them a fragrance, of modifying their appearance and/or of correcting body odors and/or protecting them or of maintaining them in good condition (amended cosmetic directive 76/768/EEC).

However, for the purpose of the present invention, the term "cosmetic compositions" also means compositions suited to be absorbed by any route allowing systemic passage, in particular orally, for the purpose of protecting the superficial parts of the body or maintaining them in good condition, or of improving the appearance of individuals, in particular in terms of the skin and its appendages.

The physiologically acceptable medium in which the 15-PGDH inhibitors according to the invention are formulated may be anhydrous or aqueous.

The composition can comprise a cosmetically acceptable medium that may be water or a mixture of water and at least one solvent selected from among hydrophilic organic solvents, lipophilic organic solvents, amphiphilic organic solvents, and mixtures thereof.

The term "anhydrous medium" means a solvent medium containing less than 1% of water. This medium may be a solvent or a mixture of solvents chosen more particularly from $C_2$-$C_4$ lower alcohols such as ethyl alcohol, alkylene glycols such as propylene glycol, and alkyl ethers of alkylene glycols or of dialkylene glycols, in which the alkyl or alkylene radicals contain from 1 to 4 carbon atoms. The term "aqueous medium" means a medium of water or a mixture of water and of another physiologically acceptable solvent, chosen in particular from the organic solvents mentioned above. In the latter case, these other solvents, when they are present, represent approximately 5 to 95% by weight of the composition.

The physiologically acceptable medium may optionally contain other adjuvants normally used in the cosmetics or pharmaceutical field, such as surfactants, thickeners or gelling agents, cosmetic agents, preservatives, or basifying or acidifying agents, that are well known in the state of the art, and in amounts sufficient to obtain the desired presentation form, in particular the form of a more or less thickened lotion, a gel, an emulsion or a cream. The use may optionally take place in a pressurized aerosol form or in a form that is sprayed from a pump-action bottle.

For topical application, the composition that can be administered according to the invention may in particular be in the form of aqueous, alcoholic, aqueous-alcoholic or oily solutions or suspensions, or of a dispersion of the lotion or serum type, of emulsions that have a liquid or semi-liquid consistency or are pasty, obtained by dispersion of a fatty phase in an aqueous phase (O/W) or vice versa (W/O) or multiple emulsions, of a free or compacted powder to be used as it is or to be incorporated into a physiologically acceptable medium, or else of microcapsules or microparticles, or of vesicular dispersions of ionic and/or nonionic type. It may thus be in the form of a salve, a tincture, milks, a cream, an ointment, a powder, a patch, an impregnated pad, a solution, an emulsion or a vesicular dispersion, a lotion, aqueous or anhydrous gels, a spray, a suspension, a shampoo, an aerosol or a foam. It may be anhydrous or aqueous. It may also comprise solid preparations constituting soaps or cleansing cakes.

These compositions are prepared according to the usual methods.

The compositions according to the invention may in particular comprise a haircare composition, and in particular a shampoo, a setting lotion, a treating lotion, a styling cream or gel, restructuring lotions for the hair, a mask, etc.

The cosmetic compositions according to the invention will preferably be a cream, a hair lotion, a shampoo or a conditioner. These can be used in particular in treatments using an application that may or may not be followed by rinsing, or else in the form of a shampoo.

A composition in the form of a foam, or else in the form of spray or an aerosol, then comprising propellant under pressure, is also intended.

It can thus be in the form of a lotion, serum, milk, O/W or W/O cream, gel, salve, ointment, powder, balm, patch, impregnated pad, cake or foam.

In particular, the compositions for application to the scalp or the hair can be in the form of a haircare lotion, for example for daily or twice-weekly application, of a shampoo or of a hair conditioner, in particular for twice-weekly or weekly application, of a liquid or solid soap for cleansing the scalp, for daily application, of a hairstyle shaping product (lacquer, hair setting product or styling gel), of a treatment mask, or of a foaming gel or cream for cleansing the hair. These may also be in the form of a hair dye or mascara to be applied with a brush or a comb.

Moreover, for topical application to the eyelashes or body hair, the compositions of the invention may be in the form of a pigmented or unpigmented mascara, to be applied with a brush to the eyelashes or alternatively to beard or moustache hair.

For a composition administration by injection, the composition may be in the form of an aqueous lotion or an oily suspension. For oral use, the composition may be in the form of capsules, granules, oral syrups or tablets.

According to a particular embodiment, the composition according to the invention is in the form of a hair cream or hair lotion, a shampoo, a hair conditioner or a mascara for the hair or for the eyelashes.

The amounts of the various constituents of the physiological medium of the composition according to the invention are those generally used in the fields under consideration.

The subject compositions can also be in the form of a dye or a mascara to be applied with a brush or with a comb, in particular to the eyelashes, the eyebrows or the hair.

These can also be in the form of a varnish intended to be applied to the surface of the nail.

The amounts of the various constituents of the compositions that can be used according to the invention are those conventionally used in the fields under consideration.

When the composition according to the invention is an emulsion, the proportion of the fatty phase can range from 5% to 80% by weight, and preferably from 5% to 50% by weight, with respect to the total weight of the composition. The oils, the waxes, the emulsifiers and the co-emulsifiers used in the composition in the form of an emulsion are selected from among those conventionally used in the cosmetics field. The emulsifier and the co-emulsifier are present, in the composition, in a proportion ranging from 0.3% to 30% by weight, and preferably from 0.5% to 20%, or even from 1% to 8% by weight, with respect to the total weight of the composition. The emulsion may also contain lipid vesicles or spherules.

When the composition according to the invention is an oily solution or gel, the fatty phase can represent more than 90% of the total weight of the composition.

Advantageously, the composition is an aqueous, alcoholic or aqueous-alcoholic solution or suspension, and better still a water/ethanol solution or suspension. The alcohol fraction can represent from 5% to 99.9%, and better still from 8% to 80%.

For a mascara application, in particular for the eyelashes, the composition of the invention is a wax-in-water or wax-in-oil dispersion, a gelled oil or an aqueous gel, this mascara also being pigmented or nonpigmented.

Advantageously, the composition will comprise microspheres, nanospheres, liposomes, oleosomes or nanocapsules, in which at least one 15-PGDH-inhibiting agent will be encapsulated. Examples of such formulations are described in particular in EP-199,636, EP-375,520, EP-447,318, EP-557,489, WO 97/12602, EP-1,151,741 or U.S. Pat. No. 5,914,126.

By way of example, the microspheres may be prepared according to the method described in EP-0,375,520.

The nanospheres may be in the form of an aqueous suspension and may be prepared according to the methods described in FR-0,015,686 and FR-0,101,438.

The oleosomes comprise of an oil-in-water emulsion formed by oily globules that have a lamellar liquid-crystal coating, dispersed in an aqueous phase (see EP-0,641,557 and EP-0,705,593).

The 15-PGDH inhibitor may also be encapsulated in nanocapsules comprising a lamellar coating obtained from a silicone surfactant as described in EP-0,780,115; the nanocapsules may also be prepared based on water-dispersible sulfonic polyesters according, for example, to the technique described in FR-0,113,337.

In a known manner, the compositions according to the invention may also contain adjuvants that are normal in the cosmetics field, such as hydrophilic or lipophilic gelling agents, hydrophilic or lipophilic additives, preservatives, antioxidants, solvents, fragrances, fillers, UV-screening agents, odor absorbers and dyestuffs. The amounts of these various adjuvants are those conventionally used in the cosmetics field, and are for example from 0.1% to 20%, in particular less than or equal to 10%, of the total weight of the composition. According to their nature, these adjuvants can be introduced into the fatty phase, into the aqueous phase and/or into the lipid spherules.

The fatty phase may contain fatty or oily compounds that are liquid at ambient temperature (25° C.) and atmospheric pressure (760 mm of Hg), generally called oils. These oils may or may not be compatible with one another and can form a liquid fatty phase that is macroscopically homogeneous or a two-phase or three-phase system.

The fatty phase may, in addition to the oils, contain waxes, gums, lipophilic polymers, and "pasty" or viscous products containing solid components and liquid components.

The aqueous phase contains water and, optionally, an ingredient that is miscible in any proportion with water, for instance $C_1$ to $C_8$ lower alcohols, such as ethanol or isopropanol, polyols such as propylene glycol, glycerol or sorbitol, or else acetone or ether.

As oils or waxes that can be used in the invention, mention may be made of mineral oils (liquid petroleum jelly), plant oils (liquid fraction of shea butter, sunflower oil), animal oils (perhydrosqualene), synthetic oils (Purcellin oil), silicone oils or waxes (cyclomethicone) and fluoro oils (perfluoropolyethers), beeswax, carnauba wax or paraffin wax. Fatty alcohols and fatty acids (stearic acid) can be added to these oils.

As emulsifiers that can be used in the invention, mention may, for example, be made of glyceryl stearate or glyceryl laurate, sorbitol stearates or oleates, alkyl dimethicone copolyols (with alkyl≧8), and mixtures thereof for a W/O emulsion. Use may also be made of polyethylene glycol monostearate or monolaurate, polyoxyethylenated sorbitol stearate or oleate, dimethicone copolyols, and mixtures thereof, in particular polysorbate 60 and the mixture of PEG-6/PEG-32/Glycol Stearate sold under the name Tefose® 63 by Gattefosse.

As solvents that can be used in the invention, mention may be made of lower alcohols, in particular ethanol and isopropanol, and propylene glycol.

As hydrophilic gelling agents that can be used in the invention, mention may be made of carboxyvinyl polymers (carbomer), acrylic copolymers such as acrylate/alkyl acrylate copolymers, polyacrylamides, polysaccharides such as hydroxypropylcellulose, natural gums and clays, and as lipophilic gelling agents, mention may be made of modified clays such as Bentones®, metal salts of fatty acids such as aluminum stearates, hydrophobic silica and ethylcellulose. When the composition is thickened or gelled using a thickener, the latter is generally present in concentrations of between approximately 0.1% to 6% with respect to the total weight of the composition.

Preferably, the inhibitor(s) is (are) present at a concentration of greater than or equal to $10^{-3}$%, in particular of 0.001% to 5% w/v relative to the composition, even more preferably of 0.01% to 2%. However, these amounts will be adjusted by those skilled in the art according to the compound used, so as to obtain an enzymatic inhibition activity equivalent to virtually complete inhibition of the 15-PGDH enzyme under the conditions of application of the composition, the concentration used generally being greater than or equal to that for which 100% inhibition of 15-PGDH is observed in vitro. The concentration of 15-PGDH inhibitor will in particular be 50 to 500 times greater than the concentration for which 100% inhibition of 15-PGDH was observed in vitro; for example, concentrations of approximately 100 times that corresponding to complete inhibition in vitro will be used.

The effective amount of 15-PGDH inhibitor corresponds to the amount required to obtain the desired result (i.e., to promote pigmentation of the skin and/or skin appendages, and/or to limit whitening thereof and will be readily evaluated by those skilled in the art according to the nature of the inhibitor used, to the individual to whom it is applied and to the amount of time for this application.

Suitable 15-PGDH inhibitors may be determined by those skilled in the art: the inhibitor will in particular be selected from among traxanox, its salts and its esters, nafazatrom, sulfasalazines, PhCL28A (Berry et al., *J. Pharm. Pharmacol.*, 1985, 37, 622-628), or the thiazolidinediones as described by Cho et al. (*Arch. Biochem. Biophys.*, 2002; 405, 247-251).

Preferably, inhibitors of NAD-dependent 15-PGDH according to the invention are not inhibitors of prostaglandin H synthases or cyclooxygenases, also referred to by the abbreviation COX, which are enzymes involved in prostaglandin synthesis.

In particular, if the 15-PGDH inhibitor(s) is (are) introduced into the compositions according to the invention in the form of plant extracts, these extracts are essentially free of flavonoids and/or have no inhibitory activity on COXs (PGHSS) at the dosages used.

According to a particularly advantageous embodiment of the invention, the composition will comprise at least one 15-PGDH-specific inhibitor; the term "specific inhibitor" means an active agent that inhibits prostaglandin synthesis, in particular PGF2α or PGE2 synthesis, very little or not at all. Preferably, the 15-PGDH inhibitor will inhibit prostaglandin synthase (PGF synthase) very little or not at all.

This is because, in the research laboratories of the assignee hereof, it has now been found, unexpectedly, that PGF synthase is also expressed in the dermal papilla. The maintaining of an effective amount of prostaglandins at the site of action therefore results from a complex biological balance between the synthesis and the degradation of these molecules. The exogenous introduction of compounds that inhibit the catabolism will therefore be less effective if this activity is combined with inhibition of the synthesis.

As a supplement to or as a replacement for this exogenous introduction, it has now been demonstrated that it is possible to promote the maintenance of an endogenous pool of prostaglandins, and therefore the maintenance of, or even an increase in, pigmentation of the skin and skin appendages, in particular of the hair.

By application of the present invention, it is now possible to target particularly active compounds for which the 15-PGDH-inhibiting activity is significantly greater than the PGF-synthase-inhibiting activity. The ratio between the inhibitory activities respectively on 15-PGDH and on PGF synthase, for the dose administered, determined in particular by means of the concentrations that inhibit 50% of the enzyme activity, will be at least greater than 1, preferably at least 3:1, advantageously greater than or equal to 5:1. Agents that are particularly suitable for implementing the invention have a ratio of 15-PGDH-inhibiting activity to PGF synthase-inhibiting activity of greater than or equal to 10:1, in particular greater than or equal to 15, preferably greater than or equal to 25:1.

In this regard, compounds that are particularly suitable according to the invention are the compounds corresponding to the formulae below:

Molecule A:

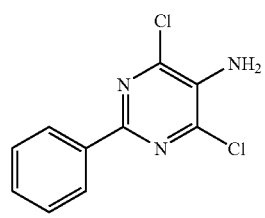

Molecule B:

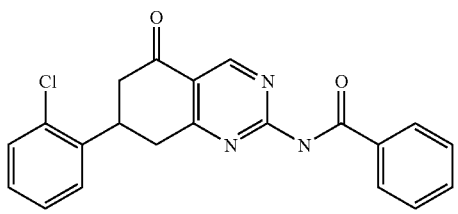

The selection of other agents that are active on 15-PGDH inhibition according to the present invention can be made by those skilled in the art by carrying out a simple test using potential candidates. This test will entail comparing the kinetics of a reaction catalyzed by this enzyme, in a reaction medium comprising a substrate for the enzyme and possible cosubstrates, in the presence or absence of the compound for which it is desired to evaluate the 15-PGDH-inhibiting role; the reaction conditions (pH, temperature, reaction time, etc.) are those that are suitable for the reaction, and are the same for the measurement in the presence or in the absence of the compound or of the substance to be tested.

For this, for example, the 15-PGDH enzyme at a final concentration of $7 \times 10^{-3}$ mg/ml, and its cosubstrate (β-NAD) and a substrate (PGE2) at the concentrations corresponding to the conditions conventionally used for this test, as described, for example, by Cho and Taï (Inhibition of NAD-dependent 15-hydroxyprostaglandin dehydrogenase (15-PGDH) by cyclooxygenase inhibitors and chemopreventive agents. *Prostaglandins, Leukotrienes and Essential Fatty Acids,* 2002, 67(6): 461-465), for example 1.5 mM of β-NAD and 50 μM of prostaglandin E2, are brought together. The reaction rate is measured at 37° C. for 1 minute. The same reaction is carried out, but adding the compound to be tested to the medium at the beginning of the reaction. The maximum enzyme reaction rate per unit time (Vmax) measured in the presence of the compound is compared with that of the control without compound, and the percentage inhibition [100−(Vmax test×100)/Vmax control] is determined.

The compounds noted as being 15-PGDH inhibitors are then tested for their ability to inhibit PGF synthase. For this, for example, the PGFS enzyme at a final concentration of $25 \times 10^{-3}$ mg/ml, and its cosubstrate (β-NADPH2) and a substrate (for example, phenanthrene quinone) at the concentrations conventionally used for this test, as described, for example, by Suzuki et al. (cDNA cloning, expression and mutagenesis study of liver-type prostaglandin F synthase. *J. Biol. Chem.* 1999, 274(1): 241-248), i.e., 100 μM of β-NADPH2 and 20 μM of phenanthrene quinone, are brought together. The maximum reaction rate per unit time at 37° C. is measured. The same reaction is carried out, but adding the compound to be tested to the medium at the beginning of the reaction. The maximum enzyme reaction rate with the compound is compared with that of the control without compound, and the percentage inhibition [100−(Vmax test×100)/Vmax control] is determined.

The percentage inhibition of the reaction catalyzed by the 15-PGDH is then compared with that of the reaction catalyzed by PGFS. More specifically, the ratio of the IC50 values for a compound with respect to PGFS and to 15-PGDH (IC50 PGFS/IC50 15-PGDH) is established. The IC50 is the concentration of the compound for which the Vmax is reduced by 50%.

The activity of compounds showing selective inhibition of 15-PGDH for the purpose of the present invention may also be demonstrated by measuring the amount of prostaglandins in a cellular model that mimics the enzymatic environment of the hair papilla. This makes it possible to evaluate the effectiveness of an inhibitor selective for 15-PGDH on the protection of prostaglandins in a complex biological system producing the various types of enzymes involved in the metabolism of these molecules. For example, a culture of promonocytes, which are precursors of macrophages under certain conditions, is used, which model is very widely used to study prostaglandin metabolism.

In fact, phorbol esters (10 nM PMA) bring about, in 24 hours, differentiation of the U937 promonocyte line to macrophages; this differentiation is accompanied by the induction of 15-PGDH (Tong and Tai, *Biochim Biophys Acta.,* 2000; 1497: 61-68).

Moreover, stimulation of these macrophages with LPS (lipopolysaccharide extracted from the bacterial wall) induces (at 100 ng/ml) in 6 hours PGHS-2 (or COX-2), which is the enzyme responsible (in the same way as COX-1) for the synthesis of PGH2, the precursor (inter alia), via PGFS, of PGF2α (Arias-Negrete et al., 1995, *Biochem Biophys Res Commun.,* 208(2), 582-589).

In a 1st step, macrophage precursors are cultured in a suitable medium, in the presence of a compound that stimulates their differentiation and the induction of 15-PGDH, and then the production of prostaglandins by these cells is stimulated, for example with LPS in the form of an extract or purified LPS; this 2nd step is carried out in the presence or absence of the compound to be tested. The concentrations of prostaglandins, in particular of PGF2α, obtained in the presence of the 15-PGDH-inhibiting compound to be tested are compared with that of the control containing only the 15-PGDH inducer, it being possible for these measurements to be carried out by any method known to those skilled in the art, in particular by enzymatic immunoassay. At the time of the assay, the amount of PGF2α measured is therefore the result of the two enzyme activities for which the compounds tested are more or less active: that of PGFS, which results in the synthesis of PGF2α, and that of 15-PGDH, which results in the degradation. In the presence of a nonselective 15-PGDH inhibitor (also an inhibitor of PGFS), a decrease in PGF2α (corresponding to a decrease in synthesis through the action of the product on PGFS) will be observed. In the presence of a selective 15-PGDH inhibitor, an increase in PGF2α, which corresponds to the decrease in degradation, will be observed. The compounds for which the amount of PGF2α observed is at least 5%, preferably at least 10%, greater than that of the control (inducer of prostaglandin synthesis alone) therefore have a protective role with respect to prostaglandin F2α. Advantageously, for the compounds suitable for implementing the invention, the concentration of prostaglandins with the compound to be tested is at least 20%, or even 30%, greater than or equal to that of the control.

Such compounds are in particular those described in application WO 03/090699;

Acetyltetrazole Compounds:

Such compounds are in particular certain salified or nonsalified acetyltetrazoles that are inhibitors of 15-hydroxyprostaglandin dehydrogenase.

According to one of the embodiments of the invention, the 15-OGDH inhibitor comprises at least an effective amount of a tetrazole compound of formula (I) or (II) or of one of its salts:

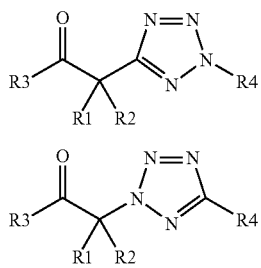

in which:

R₁ and R₂ are independently selected from among hydrogen, halogens, OR₅, SR₅, NR₅R'₅, COOR₅, COR₅, CONR₅R'₅, CF₃, CN, NR₅COR'₅, SO₂R₅, SO₂NR₅R'₅, NR₅SO₂R'₅, CSR₅, OCOR₅, COSR₅, SCOR₅, CSNR₅R'₅, NR₅CONR'₅R"₅, NR₅C(=NR'₅)NR"5R₅'", NR₅CSR'₅, NR₅CSNR'₅R"₅, linear or branched C₁-C₂₀ alkyl radicals, and rings having 4 to 7 atoms, optionally containing at least one hetero atom, with the proviso that these rings may be separated or attached, the alkyl radicals and the rings also being saturated or unsaturated, and optionally substituted with at least one substituent A₁, where R₅, R'₅, R"₅ and R'" independently denote hydrogen, a linear or branched C₁-C₂₀ alkyl radical, or a hydrocarbon-based ring having 4 to 7 atoms, the hydrocarbon-based ring or the alkyl radical being saturated or unsaturated, and optionally substituted with at least one substituent A₂;

R₃ is selected from among hydrogen, OR₆, SR₆, NR₅R₁₆, CF₃, NR₆COR'₆, NR₆SO₂R'₆, NR₅CONR'₆R"₆, NR₆CSR'₆, NR₆CSNR'₆R"₆, linear or branched C₁-C₂₀ alkyl radicals, and separated or attached hydrocarbon-based rings having 4 to 7 atoms, the alkyl radicals and the hydrocarbon-based rings also being saturated or unsaturated, and optionally substituted with at least one substituent A₃, with R₆, R'₆ and R"₆ independently denoting hydrogen, a linear or branched C₁-C₂₀ alkyl radical, or a hydrocarbon-based ring having 4 to 7 atoms, the alkyl radical or the hydrocarbon-based ring being saturated or unsaturated, and optionally substituted with at least one substituent A₄;

R₄ is selected from among hydrogen, COOR₇, CONR₇R'₇, SO₂R₇, SO₂NR₇R'₇, COR₇, CSR₇, COSR₇, CSNR₇R'₇, linear or branched C₁-C₂₀ alkyl radicals, and separated or attached hydrocarbon-based rings having 4 to 7 atoms, the alkyl radicals and the hydrocarbon-based rings also being saturated or unsaturated, and optionally substituted with at least one substituent A₅; R₄ may also represent, in the case of formula (II), a halogen, OR₇, SR₇, NR₇R'₇, CF₃, CN, NR₇COR'₇, NR₇SO₂R'₇, OCOR₇, SCOR₇, NR₇CONR'₇R"₇, NR₇C(=NR'₇)NR'₇R"₇, NR₇CSR'₇ or NR₇CSNR'₇R"₇, with R₇, R₁₇, R₁₇ and R'"₇ independently denoting hydrogen, a linear or branched C₁-C₂₀ alkyl radical, or a hydrocarbon-based ring having 4 to 7 atoms, the alkyl radical or the hydrocarbon-based ring being saturated or unsaturated, and optionally substituted with at least one substituent A₆;

A₁ and A₂ are independently selected from among halogens, heterocycles containing from 4 to 7 atoms and at least one hetero atom, OR₈, SR₈, NR₈R'₈, COOR₈, CONR₈R'₈, CF₃, CN, NR₈COR'₈, SO₂R₈, SO₂NR₈R'₈, NR₈SO₂R'₈, COR₈, CSR₈, OCOR₈, COSR₈, SCOR₈, CSNR₈R'₈, NR₈CONR'₈R"₈, NR₈C(=NR'₈)NR"₈R'"₈, NR₈CSR'₈, NR₈CSNR'₈R"₈;

A₃ and A₄ are independently selected from among halogens, R₉, OR₉, SR₉, NR₉R'₉, COOR₉, CONR₉R'₉, CF₃, CN, NR₉COR'₉, SO₂R₉, SO₂NR₉R'₉, NR₉SO₂R'₉, CSR₉, OCOR₉, COSR₉, SCOR₉, CSNR₉R'₉, NR₉CONR'₉R"₉, NR₉C(=NR'₉)NR"₉R'"₉, NR₉CSR'₉, NR₉CSNR'₉R"₉;

A₅ and A₆ are independently selected from among halogens, R₁₀, OR₁₀, SR₁₀, NR₁₀R'₁₀, CF₃, CN, NR₁₀COR'₁₀, SO₂R₁₀, SO₂NR₁₀R₁₀, NR₁₀SO₂R'₁₀, CSR₁₀, OCOR₁₀, SCOR₁₀, CSNR₁₀R'₁₀, NR₁₀CONR'₁₀R"₁₀, NR₁₀C(=NR'₁₀)NR"₁₀R'"₁₀, NR₁₀CSR'₁₀, NR₁₀CSNR'₁₀R"₁₀;

R₈, R'₈, R"₈, R'"₈, R₉, R'₉, R"₉, R'"₉, R₁₀, R'₁₀, R"₁₀, and R'"₁₀ independently denote hydrogen, a saturated or unsaturated, linear or branched C₁-C₂₀ alkyl radical, a saturated or unsaturated hydrocarbon-based ring having 4 to 7 atoms, or a benzyl radical.

The invention also features the administration of at least one tetrazole compound of formula (I) or (II) or tautomeric form, or of one of its salts, as defined above, as an agent for inducing and/or stimulating pigmentation of the hair of human beings and/or of the skin.

Advantageously, the compounds of formula (I) or (II), in salified or nonsalified form, exhibit a 15-PGDH-inhibiting activity that is greater than the PGF synthase-inhibiting activity.

In the subsequent text, and unless expressly mentioned, the use of the term "compound of formula (I) or (II)" should be understood to mean both the compound of formula (I) or of formula (II), in the form of an acid or base and in the form of a salt.

The term "at least one" according to the invention means one or more (2, 3 or more). In particular, the composition may contain one or more compounds of formula (I), one or more compounds of formula (II) or a mixture of compounds of formula (I) and of formula (II). This or these compounds may be cis or trans isomers or a mixture of cis/trans isomers. They may also be in tautomeric form. They may also be enantiomers and/or diastereoisomers or a mixture of these isomers, in particular a racemic mixture.

For the purpose of the invention, the term "hydrocarbon-based" ring means a ring containing only carbon-carbon bonds so as to form the ring.

According to the invention, the rings employed for R₁ to R₄ in formulae (I) and (II) independently contain from 4 to 7 atoms, and better still from 5 to 6 atoms. They may be saturated or unsaturated. They may also be alone or attached to another ring whose chemical structure is the same or different. In addition, R₁ and R₂ optionally contain one or more hetero atoms such as S, N or O, or combinations thereof.

According to the invention, the rings employed for R₅, R'₅, R"₅, R'"₅, R₆, R'₆, R"₆, R'"₆, R₇, R'₇, R"₇, R'"₇, R₈, R'₈, R"₈, R'"₈, R₉, R'₉, R"₉, R'"₉, R₁₀, R'₁₀, R"₁₀ and R'"₁₀ in formulae (I) and (II) independently contain from 4 to 7 carbon atoms, and better still from 5 to 6 carbon atoms. They may be saturated, or better still unsaturated.

Moreover, the heterocycles employed for A₁ and A₂ in formulae (I) and (II) contain one or more hetero atoms such as S, N or O, or combinations thereof. They also independently contain from 4 to 7 atoms, and better still from 5 to 6 atoms. In addition, they may be saturated or unsaturated.

As saturated hydrocarbon-based rings that can be used in formulae (I) or (II), mention may be made of the cyclopentyl or cyclohexyl radical. As heterocycles, mention may be made of pyridine, piperidine, morpholine, pyrrole, furan and thiazole rings. As unsaturated hydrocarbon-based rings, mention may be made of the phenyl or naphthyl radical. In addition, these rings may be substituted with one or more substituents having the definition indicated above for A₁, A₂, A₃, A₄, A₅ and $A_6$, depending on whether it is a question of $R_1$, $R_2$, $R_3$, $R_4$, $R_5$, $R'_5$, $R''_5$, $R'''_5$, $R_6$, $R'_6$, $R''_6$, $R_7$, $R'_7$, $R''_7$ or $R'''_7$.

According to the invention, the expression "linear or branched $C_1$-$C_{20}$ alkyl radical" means acyclic radicals originating from the removal of a hydrogen atom from the molecule of a linear or branched hydrocarbon having from 1 to 20 carbon atoms, and in particular methyl, ethyl, propyl, isopropyl, butyl, isobutyl, tert-butyl, pentyl, hexyl, heptyl or octyl radicals, and also their corresponding positional isomers. As examples of (saturated) alkyl radicals that can be used in the invention, mention may be made of methyl, ethyl, n-butyl, isopropyl or n-hexyl radicals.

As a halogen atom, exemplary are chlorine, fluorine, iodine or bromine atoms, and more especially chlorine atoms.

According to the invention, the compounds of formula (I) or (II) are in isolated form, i.e., nonpolymeric form. In addition, the substituents $A_1$, $A_2$, $A_3$, $A_4$, $A_5$ and $A_6$ may be located in any position of the ring bearing it, and in particular in the position adjacent to the group bearing the tetrazole ring.

According to one embodiment, at least one of $R_1$ and $R_2$ is a hydrogen atom or a halogen atom, and in particular a fluorine or chlorine atom. In particular, $R^1$ and $R_2$ represent hydrogen.

Advantageously, $R_3$ is $NR_6R'_6$ or an aryl radical, and in a particular embodiment, a naphthyl or phenyl radical, optionally substituted with the substituent $A_3$. In particular, $A_3$ is $OR_9$.

According to one embodiment, $R_6$ is hydrogen and $R'_6$ an aryl radical, in particular phenyl, optionally substituted with the group $OR_9$.

In particular, $R_9$ is a saturated, linear or branched $C_1$-$C_{20}$, and better still $C_1$-$C_{10}$, alkyl radical, and for example the methyl radical.

According to one embodiment of the invention, $R_4$ is an aryl radical, and in particular a naphthyl or phenyl radical.

According to the invention, the expression "salts of a compound of formula (I) or (II)" means the organic or inorganic salts of a compound of formula (I) or (II).

As inorganic salts that can be used according to the invention, exemplary are sodium salts or potassium salts, and also zinc ($Zn^{2+}$) salts, calcium ($Ca^{2+}$) salts, copper ($Cu^{2+}$) salts, iron ($Fe^{2+}$) salts, strontium ($Sr^{2+}$) salts, magnesium ($Mg^{2+}$) salts and manganese ($Mn^{2+}$) salts; hydroxides and carbonates.

The organic salts that can be used according to the invention are, for example, triethanolamine salts, monoethanolamine salts, diethanolamine salts, hexadecylamine salts, N,N, N',N'-tetrakis(2-hydroxy-propyl)ethylenediamine salts or trishydroxymethylaminomethane salts.

Compounds that are suitable for implementing the invention are in particular the 15-PGDH-inhibiting compounds of formula (I) or (II) as defined above, in which:

$R_1$ and $R_2$ are independently selected from among hydrogen, halogens, $OR_5$, $SR_5$, $NR_5R'_5$, $COOR_5$, $CF_3$, CN, linear or branched $C_1$-$C_{20}$ alkyl radicals, and rings having 4 to 7 atoms, optionally containing at least one hetero atom, it being possible for these rings to be separated or attached, the alkyl radicals and the rings also being saturated or unsaturated, where $R_5$ and $R'_5$ independently denote hydrogen, a linear or branched $C_1$-$C_{20}$ alkyl radical, or a hydrocarbon-based ring having 4 to 7 atoms, the hydrocarbon-based ring or the alkyl radical being saturated or unsaturated;

$R_3$ is selected from among hydrogen, $OR_6$, $SR_6$, $NR_6R'_6$, $CF_3$, linear or branched $C_1$-$C_{20}$ alkyl radicals, and separated or attached hydrocarbon-based rings having 4 to 7 atoms, the alkyl radicals and the hydrocarbon-based rings also being saturated or unsaturated, and optionally substituted with at least one substituent $A_3$, with $R_6$ and $R'_6$ independently denoting hydrogen, a linear or branched $C_1$-$C_{20}$ alkyl radical, or a hydrocarbon-based ring having 4 to 7 atoms, the alkyl radical or the hydrocarbon-based ring being saturated or unsaturated, and optionally substituted with at least one substituent $A_4$;

$R_4$ is selected from among hydrogen, $COOR_7$, $CSR_7$, linear or branched $C_1$-$C_{20}$ alkyl radicals, and separated or attached hydrocarbon-based rings having 4 to 7 atoms, the alkyl radicals and the hydrocarbon-based rings also being saturated or unsaturated; $R_4$ may also represent, in the case of formula (II), a halogen, $OR_7$, $SR_7$, $NR_7R'_7$, $CF_3$ or CN, with $R_7$ and $R'_7$ independently denoting hydrogen, a linear or branched $C_1$-$C_{20}$ alkyl radical, or a hydrocarbon-based ring having 4 to 7 atoms, the alkyl radical or the hydrocarbon-based ring being saturated or unsaturated, and optionally substituted with at least one substituent selected from among $OR_{10}$, $SR_{10}$, $NR_{10}R'_{10}$ and $CF_3$, with $R_{10}$ and $R'_{10}$ denoting a saturated or unsaturated, linear or branched $C_1$-$C_{20}$ alkyl radical;

$A_3$ and $A_4$ are independently selected from among halogens, $R_9$, $OR_9$, $SR_9$, $NR_9R'_9$, $COOR_9$ and $CF_3$, with $R_9$ and $R'_9$ independently denoting hydrogen, a saturated or unsaturated, linear or branched $C_1$-$C_{20}$ alkyl radical, a saturated or unsaturated hydrocarbon-based ring having 4 to 7 atoms, or a benzyl radical.

According to another embodiment of the invention, the 15-PGDH-inhibiting compounds are such that, in formula (I) or (II) defined above, $R_3$ is selected from among hydrogen, $OR_6$, $SR_6$, $NR_6R'_6$, $CF_3$, linear or branched $C_1$-$C_{20}$ alkyl radicals, and separated or attached hydrocarbon-based rings having 4 to 7 atoms, the alkyl radicals and the hydrocarbon-based rings also being saturated or unsaturated, and optionally substituted with at least one substituent $A_3$, with $R_6$ and $R'_6$ independently denoting hydrogen, a linear or branched $C_1$-$C_{20}$ alkyl radical, or a hydrocarbon-based ring having 4 to 7 atoms, the alkyl radical or the hydrocarbon-based ring being saturated or unsaturated, and optionally substituted with at least one substituent $A_4$;

$R_4$ is selected from among hydrogen, linear or branched $C_1$-$C_{20}$ alkyl radicals, and separated or attached hydrocarbon-based rings having 4 to 7 atoms, the alkyl radicals and the hydrocarbon-based rings also being saturated or unsaturated, and optionally substituted with at least one substituent selected from among $OR_{10}$, $SR_{10}$, $NR_{10}R'_{10}$ and $CF_3$, with $R_{10}$ and $R'_{10}$ denoting a saturated or unsaturated, linear or branched $C_1$-$C_{20}$ alkyl radical;

$A_3$ and $A_4$ are independently selected from among $R_9$, $OR_9$, $SR_9$, $NR_9R'_9$ and $COOR_9$, with $R_9$ and $R'_9$ independently denoting hydrogen, a saturated or unsaturated, linear or branched $C_1$-$C_{20}$ alkyl radical, a saturated or unsaturated hydrocarbon-based ring having 4 to 7 atoms, or a benzyl radical.

As examples of tetrazole compounds of formula (I) that can be used in the invention, mention may be made of the following compounds:

Compound 1:
1-Phenyl-2-(2-phenyl-2H-tetrazol-5-yl)ethanone

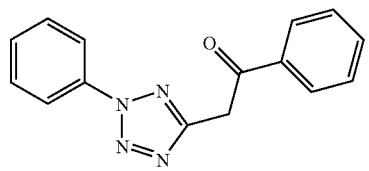

Compound 2: 1-(2-Methoxyphenyl)-2-(2-phenyl-2H-tetrazol-5-yl)ethanone

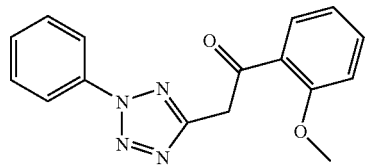

2-Ethyl-(2-phenyl-2H-tetrazol-5-yl) acetate

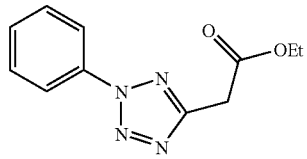

2-(2-Phenyl-2H-tetrazol-5-yl)acetic acid

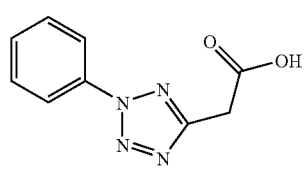

1-(3,4,5-Trimethoxyphenyl)-2-(2-phenyl-2H-tetrazol-5-yl)ethanone

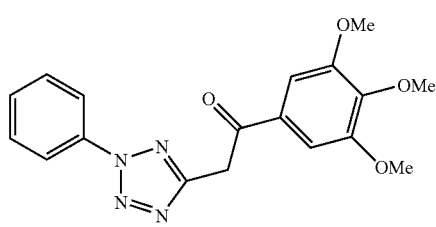

4-[2-(2-Phenyl-2H-tetrazol-5-yl)acetyl]benzoic acid

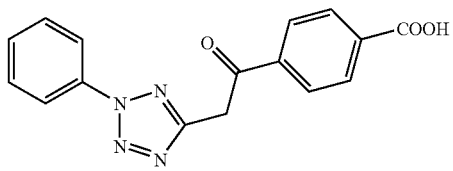

1-(4-Benzyloxyphenyl)-2-(2-phenyl-2H-tetrazol-5-yl)ethanone

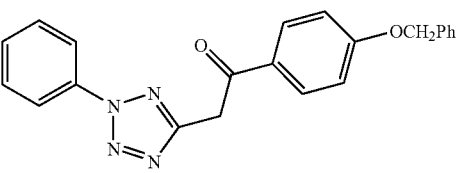

3-Methoxy-1-phenyl-2-(2-phenyl-2H-tetrazol-5-yl)propan-1-one

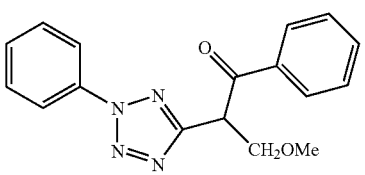

As examples of tetrazole compounds of formula (II) that can be used in the invention, mention may be made of the following compounds:

Compound 3: N-(2-Phenyl)-2-(5-phenyl-2H-tetrazol-2-yl)acetamide

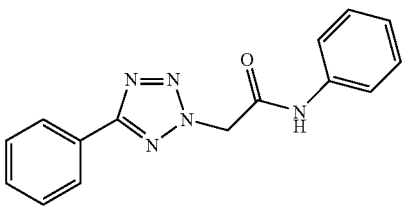

Compound 4: N-(2-Methoxyphenyl)-2-(5-phenyl-2H-tetrazol-2-yl)acetamide

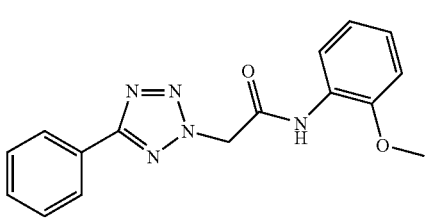

N-(4-Methylphenyl)-2-{5-[3-(trifluoromethyl)phenyl]-2H-tetrazol-2-yl}acetamide

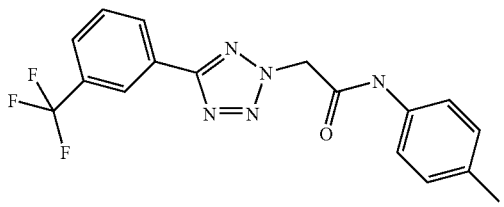

N-(2-Methoxyphenyl)-2-(2H-tetrazol-2-yl)acetamide

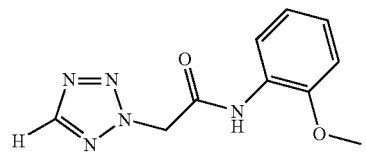

2-(5-Phenyl-2H-tetrazol-2-yl)acetamide

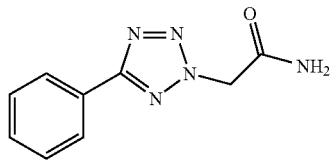

N-(2-Methoxyphenyl)-2-[5-(2-naphthyl)-2H-tetrazol-2-yl]acetamide

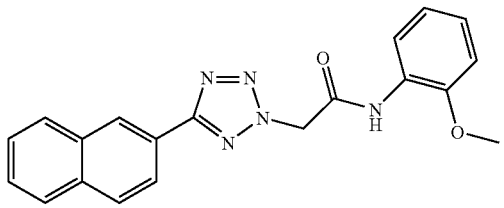

N-(2-Methoxyphenyl)-2-[5-(4-methoxyphenyl)-2H-tetrazol-2-yl)acetamide

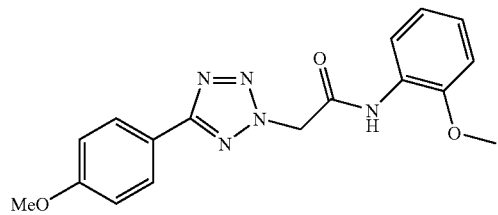

N-(3-Hydroxypropyl)-2-(5-phenyl-2H-tetrazol-2-yl)acetamide

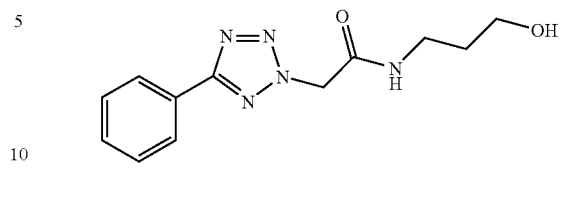

3-Hydroxy-N-(2-methoxyphenyl)-2-(5-phenyltetrazol-2-yl)propionamide

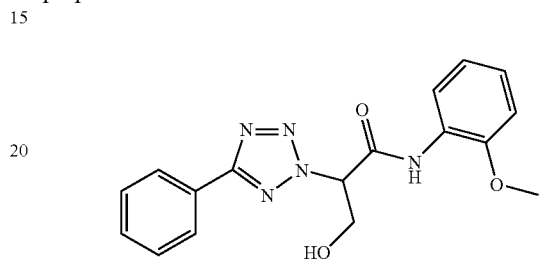

3-Methoxy-N-(2-methoxyphenyl)-2-(5-phenyltetrazol-2-yl)propionamide

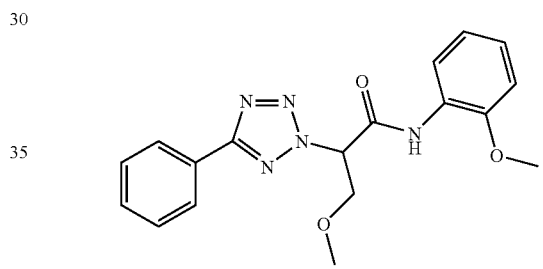

The compounds of formula (I) or (II), salified or nonsalified, can be produced in a known manner.

1) Preparation of 5-acetyltetrazoles (formula I):

The compounds (I) of the invention can be prepared by means of a method described in the literature: D. Moderhack et al., *J. Chem. Soc. Perkin Trans.*, 1, 2001, 720-728.

The reaction scheme is as follows:

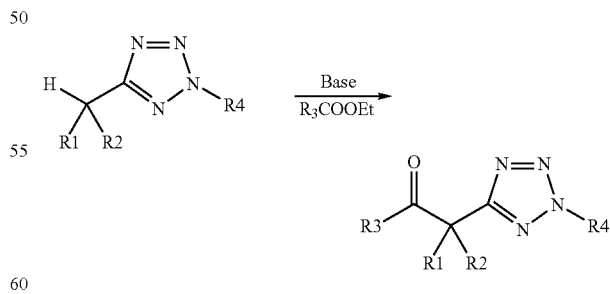

2) Preparation of 2-acetyltetrazoles (formula II):

The compounds of formula (II) of the invention can be prepared by alkylation, with α-chlorocarbonylated reactants, of tetrazoles substituted in the 5-position. This reaction is particularly suitable in the case of the synthesis of 5-phenyltetrazoles (corresponding to $R_4$=phenyl). This type of preparation is known to those skilled in the art, and in particular from F. Eindberg, *J. Org. Chem.*, 1970, 35, 11, 3978-3980.

The reaction scheme is as follows:

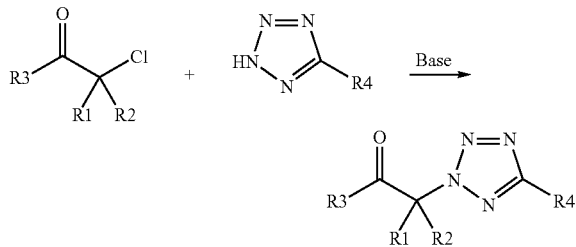

The effective amount of a compound of formula (I) or (II), or of one of its salts, corresponds to the amount required to obtain the desired result (i.e., to increase pigmentation of the hair and/or of body hair and/or of the skin. Those skilled in the art are therefore in a position to evaluate this effective amount, which depends on the nature of the compound used, on the individual to whom it is applied, and on the amount of time for this application.

In the subsequent text, and unless otherwise indicated, the amounts of the various ingredients of the composition are given as a percentage by weight with respect to the total weight of the composition.

To provide an order of magnitude according to the invention, the compound of formula (I), or one of its salts, can be used in an amount representing from $10^{-3}$% to 5% of the total weight of the composition, and preferably in an amount representing from $10^{-2}$% to 2% of the total weight of the composition, for example from 0.5% to 2%.

Phenylfuran, Phenylthiophene and Phenylpyrrole Heterocyclic Compounds:

According to another embodiment, the 15-PGDH inhibitors that are administered according to the invention are certain heterocyclic compounds, and in particular certain phenylfurans, phenylthiophenes or phenylpyrroles, that may be salified or nonsalified.

According to the invention, administrated may therefore be at least one heterocyclic compound of formula (I), or one of its salts,

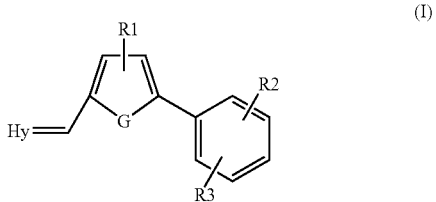

in which:

Hy is a heterocycle having 4, 5, 6 or 7 atoms, optionally comprising at least one carbonyl function and/or one thiocarbonyl function, said heterocycle being optionally substituted with at least one substituent selected from among a halogen, the groups OR, SR, NRR', COR, CSR, NRCONR'R", C(=NR)R', C(=NR)NR'R", NRC(=NR')NR"R"', OCOR, COSR, SCOR, CSNRR', NRCSR', NRCSNR'R", COOR, CONRR', CF$_3$, CN, NRCOR', SO$_2$R', SO$_2$NRR' or NRSO$_2$R', saturated or unsaturated, linear or branched C$_1$-C$_{20}$ alkyl radicals, and saturated or unsaturated rings having 4 to 7 atoms, optionally containing at least one hetero atom, it being possible for these rings to be separated or attached, it also being possible for the alkyl radicals and the rings to be substituted, where R, R', R" and R"', which may be identical or different, denote a hydrogen, or a linear or branched C$_1$-C$_{20}$ alkyl radical or an aryl radical, that is optionally substituted;

G is O, S or NH;

R$_1$, R$_2$ and R$_3$ represent, independently of one another, a hydrogen, a halogen, a group OR$_0$, SR$_0$, NR$_0$R'$_0$, COR$_0$, CSR$_0$, NR$_0$CONR'$_0$R"$_0$, C(=NR$_0$)R'$_0$, C(=NR$_0$)NR'$_0$R"$_0$, NR$_0$C(=NR'$_0$)NR"$_0$ R"'$_0$, OCOR$_0$, COSR$_0$, SCOR$_0$, CSNR$_0$R'$_0$, NR$_0$CSR'$_0$, NR$_0$CSNR'$_0$R"$_0$, COOR$_0$, CONR$_0$R'$_0$, CF$_3$, NO$_2$, CN, NR$_0$COR'$_0$, SO$_2$R'$_0$, SO$_2$NR$_0$R'$_0$ or NR$_0$SO$_2$R'$_0$, a saturated or unsaturated, linear or branched C$_1$-C$_{20}$ alkyl radical, or at least one saturated or unsaturated ring having 4 to 7 atoms, optionally containing at least one hetero atom, it being possible for the rings to be separated or attached, it also being possible for the alkyl radicals and the rings to be substituted, where R$_0$, R'$_0$, R"$_0$ and R"'$_0$, which may identical or different, denote a hydrogen, or linear or branched C$_1$-C$_{20}$ alkyl radical or an aryl radical, that is optionally substituted.

The compounds and the compositions containing them are useful for inducing and/or stimulating pigmentation of keratin fibers, in particular human keratin fibers, such as the eyelashes and the hair of human beings, and/or of the skin.

The invention also applies to keratin fibers of mammals of the animal species (dog, horse or cat, for example).

The present invention also relates to the cosmetic use of at least one heterocycle of formula (I), or of one of its salts, in a cosmetic care composition and/or makeup composition for human keratin fibers, for inducing and/or stimulating their pigmentation, and to the use of at least one compound of formula (I), or of one of its salts, for preparing a care composition or treatment composition for human keratin fibers, suited to induce and/or stimulate pigmentation of the fibers.

The human keratin fibers to which the invention is applied are in particular the hair, the eyebrows, the eyelashes, beard hair, moustache hair and pubic hair. More especially the invention applies to human hair and/or to human eyelashes.

This invention also features a method for cosmetic treatment (regime or regimen) of keratin fibers (hair or eyelashes in particular) and/or of the skin, including the scalp and the eyelids, in particular to stimulate pigmentation of the keratin fibers and/or of the skin of human beings, characterized in that it entails applying to the keratin fibers and/or the skin a cosmetic compound comprising an effective amount of at least one compound of formula (I), or of one of its salts, in leaving said composition in contact with the keratin fibers and/or the skin, and optionally in rinsing the fibers and/or said skin.

According to the invention, the term "at least one" means one or more (2, 3 or more). In particular, the composition may contain one or more compounds of formula (I). This or these compounds may be cis or trans or Z or E isomers or a mixture of cis/trans or Z/E isomers. They may also be in tautomeric form. In particular, the heterocycle Hy may be in the cis or trans or Z or E position, and better still in the Z position with respect to the adjacent double bond. This or these compounds may be enantiomers and/or diastereoisomers or a mixture of these isomers, in particular a racemic mixture.

For the purpose of the invention, the term "alkyl radical" means a hydrocarbon-based ring that may be linear or branched and saturated or unsaturated. Preferably, the alkyl radical contains from 1 to 10 carbon atoms. As examples of alkyl radicals that can be used in the invention, mention may be made of methyl, ethyl, isopropyl, n-butyl, tert-butyl, n-hexyl, 2-ethylhexyl, ethylene or propylene radicals. This radical may optionally be substituted, in particular with $OR_0$, with $R_0$ being H or a saturated, linear or branched $C_1$-$C_{20}$, and better still $C_1$-$C_{10}$, and for example $C_1$-$C_5$, alkyl radical.

According to the invention, the hetero atom(s) of Hy may be O, N, S, P, Si or Se, and in particular O, N or S. The heterocycle Hy may be saturated or unsaturated. In addition, it may contain 4, 5, 6 or 7 atoms and one or more carbonyl functions or thiocarbonyl functions or both, the carbon of these functions being part of the heterocycle.

In a particular embodiment of the invention, Hy is an aromatic ring having 5 atoms, containing, as hetero atom, sulfur, nitrogen and combinations thereof. In addition, this heterocycle Hy contains one or two carbonyl groups, in which groups the carbon is part of the heterocycle. By way of example, this heterocycle has the following formula (II):

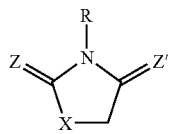

(II)

where Z, Z' and X independently represent S or O, and R is H or a saturated, linear or branched $C_1$-$C_{10}$ alkyl radical. X may also represent NH. Advantageously, Z and Z' represent oxygen, which corresponds to a 1,3-thiazolidine-2,4-dione ring.

According to the invention, the rings employed as substituent ($S_1$) contain from 4 to 7 atoms, and better still from 5 to 6 atoms. They may be saturated or unsaturated and may optionally contain one or more hetero atoms such as S, N or O, or combinations thereof. In addition, these rings may be alone or attached to another ring whose chemical structure is the same or different. When they are attached, they form fused rings.

As saturated hydrocarbon-based rings that can be used, mention may be made of the cyclopentyl or cyclohexyl radical, and as unsaturated hydrocarbon-based rings, mention may be made of the cyclohexanyl or phenyl ring. As attached hydrocarbon-based rings, mention may be made of the naphthyl radical. As heterocycles, mention may be made of pyridine, piperidine, morpholine, pyrrole, furan or thiazole rings. In addition, these rings may be substituted with one or more substituents having the definition indicated above for R or $R_0$.

According to the invention, the compounds of formula (I) are in isolated form, i.e., nonpolymeric form. They are phenylfurans, phenylthiophenes or phenylpyrroles. In addition, $R_1$ may be located in the 3-position or 4-position, taking G to be in the 1-position of the heterocycle having 5 atoms. Moreover, $R_2$ and $R_3$ may be located in any position of the phenyl ring bearing them, and in particular in the para-position or meta-position with respect to the part (A) below:

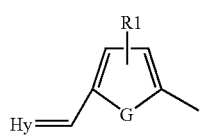

(A)

Preferably, $R_1$ is a hydrogen atom.

Advantageously, at least one of $R_2$ and $R_3$ is $CF_3$, $OR_0$ or $COOR_0$ with $R_0$ being H or a saturated or unsaturated, linear or branched $C_1$-$C_{20}$, and better still $C_1$-$C_{10}$, alkyl radical. As an example of an alkyl radical that can be used, mention may be made of methyl, ethyl, tert-butyl, isopropyl, n-butyl or n-hexyl. In particular, $COOR_0$ is COOH or $COOCH_2$—$CH_3$. In addition, $OR_0$ is in particular OH or $OCH_3$. In particular, $R_2$ is COOH or OH and $R_3$ is H; $R_2$ is $COOCH_2$—$CH_3$ and $R_3$ is H; or $R_2$ and $R_3$ represent $CF_3$ or $OCH_3$.

According to the invention, the expression "salts of compounds of formula (I)" means the simple or double, organic or inorganic salts of a compound of formula (I).

As inorganic salts that can be used according to the invention, mention may be made of: simple or double sodium salts or potassium salts, and also zinc ($Zn^{2+}$) salts, calcium ($Ca^{2+}$) salts, copper ($Cu^{2+}$) salts, iron ($Fe^{2+}$) salts, strontium ($Sr^{2+}$) salts, magnesium ($Mg^{2+}$) salts, ammonium salts and manganese ($Mn^{2+}$) salts; hydroxides, carbonates, halides (such as chlorides), sulfates, nitrates or phosphates. Preferably the salt is a sodium salt.

The organic salts that can be used according to the invention are, for example, triethanolamine salts, monoethanolamine salts, diethanolamine salts, hexadecylamine salts, N,N,N',N'-tetrakis(2-hydroxypropyl)-ethylenediamine salts or trishydroxymethylaminomethane salts, According to a particular embodiment of the invention, the heterocyclic compounds to which the invention applies have the following formula (III), and better still the following formula (IIIa), or the corresponding salt form (monosalt or disalt):

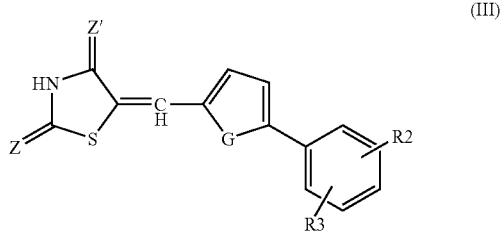

(III)

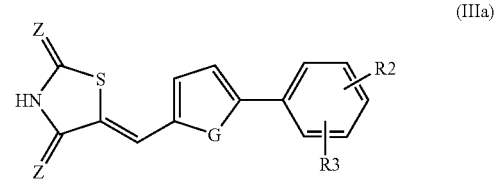

(IIIa)

in which Z, Z' and G independently represent O or S; at least one of $R_2$ and $R_3$ is $CF_3$, $OR_0$ or $COOR_0$ with $R_0$ being H or a saturated or unsaturated, linear or branched $C_1$-$C_{20}$, and better still $C_1$-$C_{10}$, alkyl radical.

The present invention also features novel heterocyclic compounds of formula (IV) below, or in the form of one of its salts, having in particular the property of inhibiting 15-PGDH and/or of preserving the amount and/or the activity of prostaglandins in particular in the hair follicle of human beings:

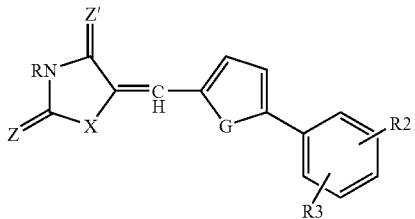

in which Z, Z' and G independently represent O or S; X is O, NH or S; R is hydrogen or a saturated, linear or branched $C_1$-$C_{10}$ alkyl radical; at least one of $R_2$ and $R_3$ is a hydrogen, CN, $NO_2$, $CF_3$, a phenyl radical, $OR_0$ or $COOR_0$, or a saturated, linear or branched $C_1$-$C_{20}$, and better still $C_1$-$C_{10}$, alkyl radical, optionally substituted with $OR_0$, with $R_0$ being H or a saturated, linear or branched $C_1$-$C_{20}$, and better still $C_1$-$C_{10}$, alkyl radical, on the condition that, when X=S and Z=Z'=G or Z≠Z', then $R_2$ and $R_3$ are other than COOH.

According to a particular embodiment, the heterocyclic compound has the following formula (V) or is a corresponding salt:

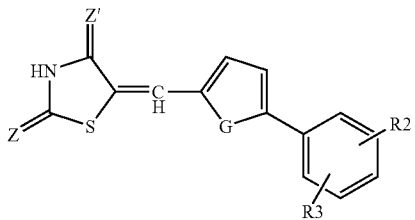

in which Z, Z' and G independently represent O or S; at least one of $R_2$ and $R_3$ is phenyl $NO_2$, $CF_3$, $OR_0$, $COOR_0$ or a saturated, linear or branched $C_1$-$C_{20}$, and better still $C_1$-$C_{10}$, alkyl radical, optionally substituted with $OR_0$, with $R_0$ being H or a saturated, linear or branched $C_1$-$C_{20}$, and better still $C_1$-$C_{10}$, alkyl radical, on the condition that, when Z=Z'=G or Z≠Z', then $R_2$ and $R_3$ are other than COOH.

Advantageously, when Z=Z'=G, at least one of $R_2$ and $R_3$ is $CF_3$, $OR_0$ or $COOR_0$ with $R_0$ being a saturated, linear or branched $C_1$-$C_{10}$, and better still $C_1$-$C_5$, alkyl radical. According to another preferred embodiment of the invention, when Z=Z' and they are other than G, at least one of $R_2$ and $R_3$ is $CF_3$ or $COOR_0$, with $R_0$ being H.

According to another embodiment of the invention, the heterocyclic compound has the following formula (VI) or a corresponding salt form:

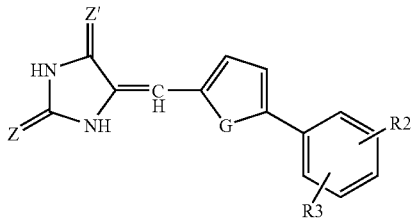

in which Z, Z' and G independently represent O or S; at least one of $R_2$ and $R_3$ is a hydrogen, CN, $CF_3$, $NO_2$, $OR_0$, $COOR_0$ or a saturated, linear or branched $C_1$-$C_{20}$, and better still $C_1$-$C_{10}$, alkyl radical, optionally substituted with $OR_0$, with $R_0$ being H or a saturated, linear or branched $C_1$-$C_{20}$, and better still $C_1$-$C_{10}$, alkyl radical.

According to another embodiment of the invention, the heterocyclic compound has the following formula (VII) or the corresponding salt form:

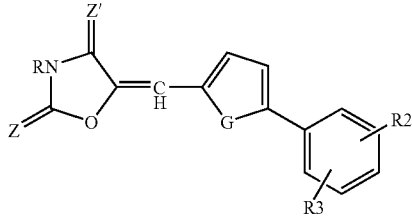

in which Z, Z' and G independently represent O or S; R is a saturated, linear or branched $C_1$-$C_{10}$ alkyl radical; at least one of $R_2$ and $R_3$ is a saturated, linear or branched $C_1$-$C_{20}$, and better still $C_1$-$C_{10}$, alkyl radical, $NO_2$ or $OR_0$, with $R_0$ being H or a saturated, linear or branched $C_1$-$C_{20}$, and better still $C_1$-$C_{10}$, alkyl radical.

Preferably, the heterocyclic compound of the invention is in the Z form.

The compounds of formula (I) or their salts may be produced in a known manner as described in document WO 01/066541. The compounds of formula (I) are solid at ambient temperature.

Styrylpyrazole Compounds:

According to another embodiment, the 15-PGDH inhibitors that are administered according to the invention comprise at least one styrylpyrazole compound, or one of its physiologically acceptable salts.

Such compounds correspond to formula (I):

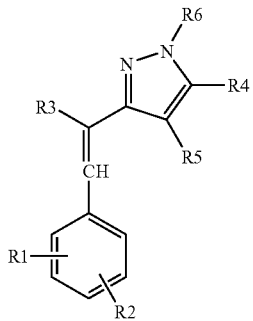

in which:

$R_1$, $R_2$, $R_4$ and $R_5$, which may be identical or different, are selected from among hydrogen, a halogen, the groups $OR_7$, $SR_7$, $NR_7R_{17}$, $COOR_7$, $CONR_7R'_7$, $CF_3$, CN, $NR_7COR'_7$, $SO_2R_7$, $SO_2NR_7R'_7$, $NR_7SO_2R'_7$, $COR_7$, $CSR_7$, $OCOR_7$, $COSR_7$, $SCOR_7$, $CSNR_7R'_7$, $NR_7CONR'_7R''_7$, $NR_7C(=NR'_7)NR''_7R'''_7$, $NR_7CSR'_7$ or $NR_7CSNR'_7R''_7$, saturated or unsaturated, linear or branched $C_1$-$C_{20}$ alkyl radicals, and saturated or unsaturated rings having 4 to 7 atoms, optionally containing at least one hetero atom, it being possible for these rings to be separated or attached, it also being possible for the alkyl radicals and the rings to be substituted with at least one substituent $A_1$, with $R_7$, $R'_7$, $R''_7$ and $R'''_7$ independently denoting hydrogen, a linear or branched $C_1$-$C_{20}$ alkyl radical or a ring having 4 to 7 atoms, optionally containing at least one hetero atom, isolated or attached to another ring, the alkyl radical or said rings being saturated or unsaturated, and optionally substituted with at least one substituent $A_2$;

$R_3$ is selected from among CN, $COOR_8$, $CONR_8R'_8$, $COR_8$, $SO_2R_8$ and $SO_2NR_8R'_8$, with $R_8$ and $R'_8$ independently denoting hydrogen, a linear or branched $C_1$-$C_{20}$ alkyl radical or a ring having 4 to 7 atoms, isolated or attached to another ring and optionally containing at least one hetero atom, the alkyl radical or said rings being saturated or unsaturated, and optionally substituted with at least one substituent $A_3$;

$R_6$ is selected from among hydrogen, the groups $COOR_9$, $COR_9$, $CSR_9$, $COSR_9$, $CONR_9R'_9$, $SO_2R_9$ or $SO_2NR_9R'_9$, saturated or unsaturated, linear or branched $C_1$-$C_{20}$ alkyl radicals, and saturated or unsaturated rings having 4 to 7 atoms, optionally containing at least one hetero atom, it being possible for these rings to be separated or attached, it also being possible for the alkyl radicals and the rings to be substituted with at least one substituent $A_4$, with $R_9$ and $R'_9$, which may be identical or different, denoting hydrogen, a linear or branched $C_1$-$C_{20}$ alkyl radical, or a ring having 4 to 7 atoms, optionally containing at least one hetero atom, isolated or attached to another ring, the alkyl radical or said rings being saturated or unsaturated, and optionally substituted with at least one substituent $A_5$;

$A_1$, $A_2$, $A_3$, $A_4$ and $A_5$ being independently selected from among halogens, and the groups $OR_{10}$, $SR_{10}$, $NR_{10}R'_{10}$, $COOR_{10}$, $CH_2COOR_{10}$, $CONR_{10}R'_{10}$, $CF_3$, CN, $NR_{10}COR'_{10}$, $SO_2R_{10}$, $SO_2NR_{10}R'_{10}$, $NR_{10}SO_2R'_{10}$, $COR_{10}$, $CSR'_{10}$, $OCOR_{10}$, $COSR_{10}$, $SCOR_7$, $CSNR_{10}$, $R'_{10}$, $NR_{10}CONR'_{10}R''_{10}$, $NR_{10}C(=NR'_{10})NR''_{10}R'''_{10}$, $NR_{10}CSNR'_{10}R''_{10}$ or $NR_{10}CSR'_{10}$, with $R_{10}$, $R'_{10}$, $R''_{10}$ and $R'''_{10}$, which may be identical or different, denoting hydrogen, a linear or branched $C_1$-$C_{20}$ alkyl radical, or a ring having 4 to 7 atoms, optionally containing at least one hetero atom, isolated or attached to another ring, the alkyl radical or said rings being saturated or unsaturated.

The invention also relates to the use, in particular cosmetic use, of at least one pyrazole compound of formula (I), or of one of its salts, as defined above, as an agent for inducing and/or stimulating pigmentation of keratin fibers, in particular human keratin fibers, such as the eyelashes and the hair of human beings, and/or of the skin.

The invention also applies to the keratin fibers of mammals of the animal species (dog, horse or cat, for example).

The invention also relates to the cosmetic use of at least one pyrazole compound of formula (I), or of one of its salts, in a cosmetic care composition and/or makeup composition for human keratin fibers, for inducing and/or stimulating their pigmentation and/or that of the skin, and also to the use of at least one compound of formula (I), or of one of its salts, for preparing a care composition or a treatment composition for human keratin fibers, intended to induce and/or stimulate pigmentation of the fibers and/or of the skin.

The human keratin fibers to which the invention applies are in particular the hair, the eyebrows, the eyelashes, beard hair, moustache hair and pubic hair. More especially, the invention applies to human hair and/or to human eyelashes.

The invention also relates to the cosmetic use of at least one pyrazole compound of formula (I), or of one of its salts, in a cosmetic haircare composition for human beings, for promoting pigmentation of the hair and/or of the skin.

This invention also features the cosmetic use of at least one pyrazole compound of formula (I), or of one of its salts, in a cosmetic care composition and/or makeup composition for the eyelashes of human beings, for inducing and/or stimulating pigmentation of the eyelashes and/or increasing their density, and also the use of at least one compound of formula (I), or of one of its salts, for preparing a care composition and/or a treatment composition for the eyelashes of human beings, intended to induce and/or stimulate pigmentation of the eyelashes. This composition thus makes it possible to keep the eyelashes in good condition and/or to improve their condition and/or their appearance.

According to the invention, the term "at least one" means one or more (2, 3 or more). In particular, the composition may contain one or more compounds of formula (I). This or these compounds may be cis or trans or Z or E isomers or a mixture of cis/trans or Z/E isomers. In particular, the aromatic ring may be in the cis or trans or Z or E position, and better still in the Z position, with respect to the pyrazole ring. This or these compounds may also be in tautomeric form. They may also be enantiomers and/or diastereoisomers or a mixture of these isomers, in particular a racemic mixture.

According to the invention, the rings employed for $R_1$ to $R_{10}$, $R'_7$, $R''_7$, $R'''_7$, $R'_8$, $R'_9$, $R'_{10}$, $R''_{10}$ and $R'''_{10}$ contain from 4 to 7 atoms, and better still from 5 to 6 atoms. They may be saturated or unsaturated and may optionally contain one or more hetero atoms such as S, N or O, or combinations thereof. They may be alone or attached to another ring, which may be identical or different. As saturated carbon rings that can be used, mention may be made of the cyclopentyl or cyclohexyl radical. As heterocycles, mention may be made of pyridine, piperidine, morpholine, pyrrole, furan or thiazole rings. As unsaturated carbon rings, mention may be made of the phenyl or naphthyl radical. In addition, these rings may be substituted with a substituent having the definition indicated above for $A_1$. Advantageously, when $R_6$ contains one or more hetero atoms, the bond with the nitrogen of the pyrazole ring occurs in the form of an N—C bond.

According to one embodiment of the invention, the substituent(s) borne by the alkyl or aryl radicals, i.e., $A_1$ to $A_5$, are halogen atoms, and in particular chlorine, bromine, iodine or fluorine atoms, preferably chlorine atoms, or linear or branched $C_1$-$C_{20}$ alkyl radicals or else perfluoroalkyl radicals. As an example of perfluoroalkyl radicals that can be used, mention may be made of $CF_3$.

For the purpose of the invention, the term "alkyl radical" means a hydrocarbon-based radical that may be linear or branched and saturated or unsaturated. Preferably, the alkyl radical contains from 1 to 10 carbon atoms.

As examples of an alkyl radical that can be used according to the invention, mention may be made of methyl, ethyl, isopropyl, n-butyl, n-hexyl, 2-ethylhexyl, ethylene or propylene.

According to the invention, the compounds of formula (I) (or their salt(s)) are in isolated form, i.e., nonpolymeric form. In addition, $R_1$ and $R_2$ may be located in any position of the phenyl ring, and in particular in the ortho-position with respect to the branching of the pyrazole part.

Advantageously, $R_1$ and $R_2$ do not simultaneously represent $OR_7$.

Preferably, at least one of $R_1$ and $R_2$ is a hydrogen atom, $OR_7$, $CF_3$ or a halogen atom, and in particular a chlorine atom, $R_7$ representing a $C_1$-$C_{10}$ alkyl radical, and for example methyl. In particular, $R^1$ and/or $R_2$ represent(s) a halogen atom, and in particular a chlorine atom.

Advantageously, $R_3$ is CN, $COOR_8$, $CONR_8R_{18}$ or $COR_8$, and for example CN.

According to one embodiment of the invention, $R_4$, $R_5$ and $R_6$ represent, independently of one another, a $C_1$-$C_{10}$ alkyl radical optionally substituted with $OR_{10}$ such as CH₂CH₂OR₁₀, NH₂, H or CN, or a saturated or unsaturated hydrocarbon-based ring, such as a phenyl ring, R₁₀ representing H, for example. Advantageously, R₆ is CH₂CH₂OR₁₀, and in particular CH₂CH₂OH, or the phenyl radical. Preferably, R₄ is NH₂ or H. According to an advantageous embodiment, R₅ is CN or H.

According to the invention, the expression "salts of a compound of formula (I)" means the organic or inorganic salts of a compound of formula (I).

As inorganic salts that can be used according to the invention, mention may be made of sodium salts or potassium salts, and also zinc ($Zn^{2+}$) salts, calcium ($Ca^{2+}$) salts, copper ($Cu^{2+}$) salts, iron ($Fe^{2+}$) salts, strontium ($Sr^{2+}$) salts, magnesium ($Mg^{2+}$) salts, ammonium salts and manganese ($Mn^{2+}$) salts; hydroxides, carbonates, halides (chlorides), sulfates, nitrates or phosphates.

The organic salts that can be used according to the invention are, for example, triethanolamine salts, monoethanolamine salts, diethanolamine salts, hexadecylamine salts, N,N,N',N'-tetrakis(2-hydroxy-propyl)ethylenediamine salts or trishydroxymethylaminomethane salts.

According to a particular embodiment of the invention, the pyrazole compounds to which the invention applies are of formula (II) or are one of its salts:

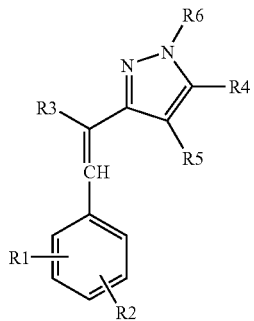

in which:

R₁, R₂, R₄ and R₅ independently represent H, a halogen, OR₇, SR₇, NR₇R'₇, COOR₇, CONR₇R'₇, CF₃ or CN, a saturated or unsaturated $C_1$-$C_{10}$ alkyl radical, or a saturated or unsaturated ring, that is separated or attached to another ring, optionally containing at least one hetero atom, it also being possible for the alkyl radicals and the rings to be substituted with at least one substituent A₁, with R₇ and R'₇ independently denoting H, a $C_1$-$C_{10}$ alkyl radical, or a ring that is isolated or attached to another ring;

R₃ is CN, COOR₈, CONR₈R'₈ or COR₈, with R₈ and R'₈ independently denoting H, a $C_1$-$C_{10}$ alkyl radical, or a ring that is isolated or attached to another ring and that optionally contains at least one hetero atom, said rings being saturated or unsaturated, and optionally substituted with at least one substituent A₁;

R₆ is hydrogen, COOR₉, COR₉, a saturated or unsaturated $C_1$-$C_{10}$ alkyl radical, or a saturated or unsaturated ring that is separated or attached to another ring, optionally containing at least one hetero atom, it also being possible for the alkyl radicals and the rings to be substituted with at least one substituent A₁, with R₉ and R'₉ independently denoting H, a $C_1$-$C_{20}$ alkyl radical, or a ring that is isolated or attached to another ring;

the rings having from 5 to 6 atoms;

the hetero atoms being O, N or S, or a combination thereof.

Advantageously, the compound of formula (I) or (II) is in the z form.

According to another embodiment of the invention, the pyrazole compounds have the following formula (III) or are one of its salts:

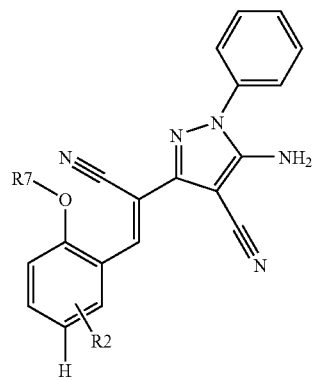

R₇ is
a) a saturated or unsaturated, linear or branched $C_1$-$C_{10}$ alkyl radical optionally substituted with at least one substituent A₁; or b) a saturated or unsaturated ring $C^1$ having 4 to 7 atoms, optionally containing at least one hetero atom and/or optionally being substituted with at least one substituent A₁ and/or optionally attached to at least one saturated or unsaturated ring $C^2$ having 4 to 7 atoms, optionally containing at least one hetero atom;

R₂ is
OR₇, SR₇, NR₇R'₇, COOR₇, CONR₇R'₇, CF₃, CN, NR₇COR'₇, SO₂R₇, SO₂NR₇R'₇, NR₇SO₂R'₇, COR₇, CSR₇, OCOR₇, COSR₇, SCOR₇, CSNR₇R'₇, NR₂CONR'₇R"₇, NR₇C(=NR'₇)NR"₇R'"₇, NR₇CSR'₇ or NR₇CSNR'₇R"₇, a saturated or unsaturated $C_1$-$C_{10}$ alkyl radical, or a saturated or unsaturated ring $C^3$ that is separated or attached to another ring $C^4$, optionally containing at least one hetero atom, it also being possible for the alkyl radicals and the rings to be substituted with at least one substituent A₁, where R₇ and R'₇, which may be identical or different, denote:

the hydrogen atom or a saturated or unsaturated, linear or branched $C_1$-$C_{10}$ alkyl radical, a $C_5$ aromatic ring optionally including at least one hetero atom, optionally substituted with at least one substituent A₂; and where the hetero atoms are selected from N, O and S, and a combination thereof.

Since the compounds of formula (III) or their salts are novel, the present invention also features styrylpyrazole compounds of formula (III) or one of its salts.

Advantageously, R₂ is OR₇ and R₇ is a saturated $C_1$-$C_{10}$ alkyl radical such as methyl.

As examples of pyrazole compounds of formula (I) according to the invention, mention may be made of the following compounds:

Compound 1:

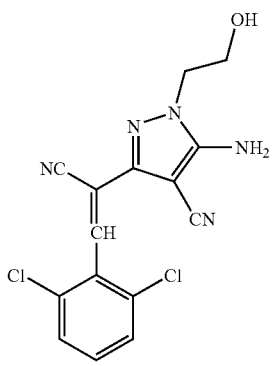

Compound 2:

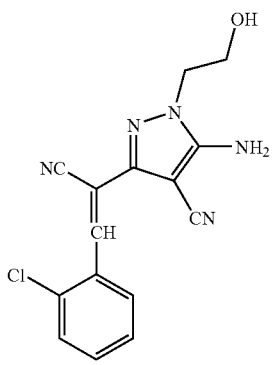

Compound 3:

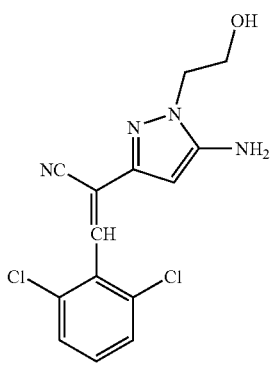

Compound 4:

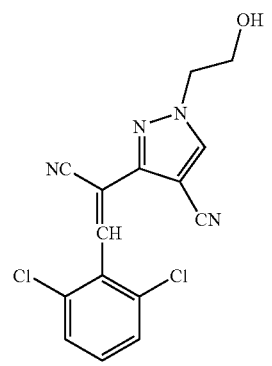

-continued

Compound 5:

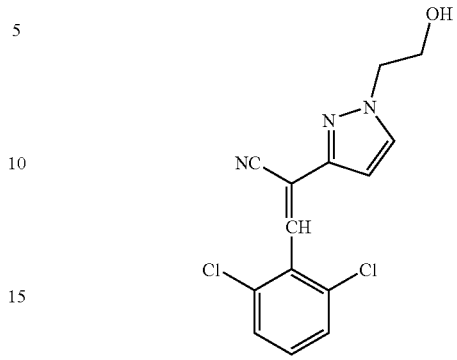

The compounds of formula (I) or their salts, certain of which are known as such, can be produced by condensation of a benzaldehyde, optionally substituted with a pyrazole substituted with an activated methylene, with one of the nitrile, acid, ester, amide or ketone functions. Water is eliminated simultaneously by azeotropic distillation and the installation of a "Dean-Stark" apparatus. This type of preparation is known by those skilled in the art from EP-0,245,825. These compositions are in the form of a solid, and in particular in pulverulent form, or else in liquid form.

In the subsequent text, and unless otherwise indicated, the amounts of the various ingredients of the composition are given as a percentage by weight with respect to the total weight of the composition.

To provide an order of magnitude according to the invention, the compound of formula (I) or one of its salts or a mixture of compounds of formula (I) and/or of their salt can be used in an amount representing from $10^{-3}$% to 105% of the total weight of the composition, and preferably in an amount representing from $10^{-3}$% to 5%, and better still from $10^{-2}$% to 2%, of the total weight of the composition, for example from 0.5% to 2%.

Pyrazolecarboxamide Compounds:

According to another embodiment, the 15-PGDH inhibitor that is administered according to the invention comprises at least one pyrazole compound of formula (I) or one of its salts:

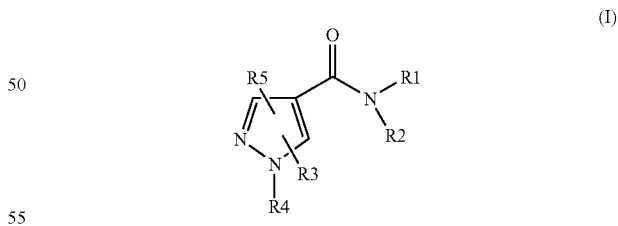

in which:
R$_1$ and R$_2$ are selected independently from among:
    hydrogen,
    saturated or unsaturated, linear or branched $C_1$-$C_{20}$ alkyl radicals optionally substituted with at least one substituent T$_1$,
    saturated or unsaturated rings containing at least one hetero atom selected from among O, N and S, and saturated hydrocarbon-based rings, these rings containing from 4 to 7 atoms and it being possible for them to be optionally attached, to contain a carbonyl or thiocarbonyl function and/or to be substituted with at least one substituent $T_2$ selected from A and R, it also being possible for $R_1$ and $R_2$ to form a heterocycle having 4 to 7 atoms with the nitrogen to which they are attached;

$R_3$ and $R_5$ are selected independently from among:
hydrogen, '''
A,
halogens,
the groups $OR_6$ $SR_6$ $NR'_6{}_6$ CN, $CF_3$, $COR_6$, $CSR_6$, $COOR_6$, $COSR_6$, $CSOR_6$, $CSSR_6$, $NR_6COR'_6$, $NR_6CSR'_6$, $OCOR_6$, $SCOR_6$, $CSNR_6R'_6$, $SO_2R_6$, $SO_2NR_6R'_6$, $NR_6SO_2R'_6$, $NR_6C(=NR_{16})NR''_6R'''_6$ and $SiR_6R'_6R''_6$,
saturated or unsaturated rings having 4 to 7 atoms, optionally containing at least one hetero atom from O, N and S, it being possible for these rings to be optionally attached, to contain a carbonyl or thiocarbonyl function and/or to be substituted with at least one substituent $T_3$ selected from A and R;

$R_4$ is selected from among:
hydrogen,
A,
the groups $COR_6$, $CSR_6$, $COOR_6$, $CONR_6R'_6$, $CSNR_6R'_6$, $SO_2R_6$ and $SO_2NR_6R'_6$,
saturated or unsaturated hydrocarbon-based rings having 4 to 7 atoms, heterocycles having 5 atoms containing from one to four hetero atoms, heterocycles having 6 atoms containing from one to three nonadjacent hetero atoms, heterocycles having 4 or 7 atoms containing from one to three hetero atoms, the hetero atoms being selected from among O, N and S, these heterocycles being saturated or unsaturated, it being possible for said rings and said heterocycles to be optionally attached, to contain a carbonyl or thiocarbonyl function and/or to be substituted with at least one substituent $T_4$ selected from A and R;

$R_6$, $R'_6$, $R''_6$ and $R'''_6$ are selected from among:
hydrogen,
saturated or unsaturated, linear or branched $C_1$-$C_{20}$ alkyl radicals optionally substituted with at least one substituent R',
saturated or unsaturated rings having 4 to 7 atoms, optionally containing at least one hetero atom selected from among O, N and S, it being possible for these rings to be optionally attached, to contain a carbonyl or thiocarbonyl function and/or to be substituted with at least one substituent R;

R is selected from among:
saturated or unsaturated, linear or branched $C_1$-$C_{20}$ alkyl radicals,
halogens,
the groups $OR_7$, $SR_7$, $NR_7R'_7$, CN, $CF_3$, $COR_7$, $CSR_7$, $COOR_7$, $COSR_7$, $CSOR_7$, $CSSR_7$, $NR_7COR'_7$ $NR_7CSR_{17}$, $OCOR_7$, $SCOR_7$, $CSNR_7R'_7$, $SO_2R_7$, $SO_2NR_7R'_7$, $NR_7SO_2R_{17}$, $NR_7C(=NR'_7)NR''_7R'''_7$ and $SiR_7R'_7R''R'''_7$;

R' is selected from among:
saturated or unsaturated, linear or branched $C_1$-$C_{20}$ alkyl radicals, halogens,
the groups $OR_7$, $SR_7$, $NR_7R'_7$, CN, $CF_3$, $COR_7$, $CSR_7$, $COOR_7$, $COSR_7$, $CSOR_7$, $CSSR_7$, $NR_7COR'_7$, $NR_7CSR'_7$, $OCOR_7$, $SCOR_7$, $CSNR_7R'_7$, $SO_2R_7$, $SO_2NR_7R'_7$, $NR_7SO_2R_{17}$, $NR_7C(=NR'_7)NR'_7R'''_7$ and $SiR_7R'_7R''_7$;
saturated or unsaturated rings having 4 to 7 atoms, optionally containing at least one hetero atom selected from among O, N and S, it being possible for these rings to be optionally attached and/or to contain a carbonyl or thiocarbonyl function;

$R_7$, $R'_7$, $R''_7$ and $R'''_7$ independently represent hydrogen or a saturated or unsaturated, linear or branched $C_1$-$C_{20}$ alkyl;

A is a saturated or unsaturated, linear or branched $C_1$-$C_{20}$ alkyl radical optionally substituted with at least one substituent $T_5$ chosen from: R' and saturated or unsaturated rings having 4 to 7 atoms, optionally containing at least one hetero atom selected from among O, N and S, it being possible for these rings to be optionally attached, to contain a carbonyl or thiocarbonyl function and/or to be substituted with at least one substituent R;

$T_1$ is selected from among $OR_6$, $SR_6$, $NR_6R'_6$, CN, $CF_3$, $COR_6$, $CSR_6$, $COOR_6$, $COSR_6$, $CSOR_6$, $CSSR_6$, $NR_6COR'_6$, $NR_6CSR'_6$, $OCOR_6$, $SCOR_6$, $CSNR_6R'_6$, $SO_2R_6$, $SO_2NR_6R'_6$, $NR_6SO_2R'_6$, $NR_6C(=NR'_6)NR''_6R'''_6$ and $SiR_6R'_6R''_6$, halogens, and saturated or unsaturated rings having 4 to 7 atoms, optionally containing at least one hetero atom selected from among O, N and S, it being possible for these rings to be optionally attached, to contain a carbonyl or thiocarbonyl function and to be substituted with at least one substituent R.

The invention also relates to the use of at least one pyrazole compound of formula (I), or of one of its salts, as defined above, as an agent for inducing and/or stimulating pigmentation of keratin fibers, in particular human keratin fibers, such as the hair and the eyelashes of human beings, and/or of the skin.

The invention also applies to the keratin fibers of mammals of the animal species (dog, horse or cat, for example).

The invention also relates to the cosmetic use of at least one pyrazole compound of formula (I), or of one of its salts, in a cosmetic care and/or makeup composition for human keratin fibers, for inducing and/or stimulating their pigmentation, and also to the use of at least one compound of formula (I), or of one of its salts, for preparing a care composition or a treatment composition for human keratin fibers, intended to induce and/or stimulate pigmentation of the fibers.

The human keratin fibers to which the invention applies are in particular the hair, the eyebrows, the eyelashes, beard hair, moustache hair and pubic hair. More especially, the invention applies to human hair and/or to human eyelashes.

The invention also relates to the cosmetic use of at least one pyrazole compound of formula (I), or of one of its salts, in a cosmetic haircare composition for human beings, for reducing canities and/or increasing the pigmentation. This invention also features the use of at least one pyrazole compound of formula (I), or of one of its salts, for preparing a hair composition for human beings, intended to induce and/or stimulate pigmentation of the hair and/or to impair whitening thereof.

The present invention in particular features the use of novel pyrazolecarboxamide compounds of formula III or one of its salts:

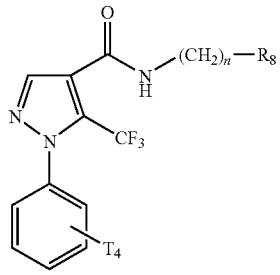

(III)

where $R_8$ is OH or $—S—(CH_2)_m—R_9$, with $R_9$ representing H or Hy; T4 is H or 4-COOH; n is an integer ranging from 1 to 10 and m is an integer ranging from 1 to 10; Hy is a heterocycle having 4 to 7 atoms.

In the subsequent text, and unless expressly mentioned, the use of the term "compound of formula I" should be understood to mean both the compound of the formula (I) in the form of an acid or a base, and one of its salts.

According to the invention, the term "at least one" means one or more (2, 3 or more). In particular, the composition may contain one or more compounds of formula (I). This or these compounds may be cis or trans or Z or E isomers or a mixture of cis/trans or Z/E isomers. They may also be in tautomeric form. This or these compounds may also be enantiomers and/or diastereoisomers or a mixture of these isomers, in particular a racemic mixture.

According to the invention, the rings employed for $R_1$, $R_2$, $R_3$, $R_4$, $R_5$, $R_6$, $R'_6$, $R''_6$, $R'''_6$, $R'$, $T_1$ and $T_5$ contain from 4 to 7 atoms, and better still from 5 to 6 atoms. They may be saturated or unsaturated and may optionally contain one or more hetero atoms such as S, N or O, or combinations thereof. As saturated carbon rings that can be used, mention may be made of the cyclopentyl or cyclohexyl radical. As heterocycles, mention may be made of pyridine, piperidine, morpholine, pyrrole, furan, thiophene, imidazole, oxazole, thiazole, pyrazole, pyrimidine, pyrazine or pyridazine rings. As unsaturated carbon rings, mention may be made of the phenyl radical. In addition, these rings may be substituted in particular with a substituent such as A or R. Furthermore, $R_1$ and $R_2$ may form a heterocycle with the nitrogen to which they are attached, containing from 4 to 7 atoms, and better still from 5 to 6 atoms, and containing from 1 to 3 hetero atoms selected from among O, N and S.

For $R_4$, the pyridine, piperidine, morpholine, pyrrole, furan, thiophene, imidazole, oxazole, thiazole, pyrazole, pyrimidine or pyrazine ring can be used as a heterocycle.

In addition, these rings (or heterocycles) may be alone or attached to another ring whose chemical structure is the same or different, and may thus form fused rings. As fused rings, mention may be made of the naphthyl, benzofuran, benzothiophene or indole radical.

For the purpose of the invention, the term "alkyl radical" means a hydrocarbon-based radical that may be linear or branched, and saturated or unsaturated. In particular, the alkyl radical contains from 1 to 10 carbon atoms.

As examples of an alkyl radical that can be used according to the invention, mention may be made of methyl, ethyl, isopropyl, n-butyl, tert-butyl, n-hexyl, 2-ethylhexyl, ethylene or propylene radicals.

As a halogen atom, exemplary are chlorine, fluorine or bromine atoms, and better still of fluorine and of chlorine atoms According to the invention, the compounds of formula (I) are in isolated form, i.e., nonpolymeric form.

According to a particular embodiment of the invention, the pyrazolecarboxamide compound has the following formula (II) or is one of its salts:

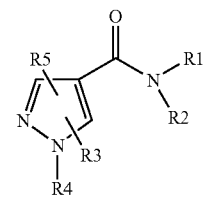

(II)

in which:

$R_1$ and $R_2$ are selected independently from among:
  hydrogen,
  saturated or unsaturated, linear or branched $C_1$-$C_{20}$ alkyl radicals optionally substituted with at least one substituent $T_1$, it also being possible for $R_1$ and $R_2$ to form a heterocycle having 4 to 7 atoms with the nitrogen to which they are attached;

$R_3$ and $R_5$ are selected independently from among:
  hydrogen,
  A,
  halogens,
  the groups $OR_6$ $SR_6$ $NR_6R'_6$ CN, $CF_3$, $COOR_6$,
  saturated or unsaturated rings having 4 to 7 atoms, optionally containing at least one hetero atom selected from among O, N and S, it being possible for these rings to be optionally attached and/or to be substituted with at least one substituent $T_3$ selected from A and R;

$R_4$ is selected from among:
  hydrogen,
  A,
  the groups $COR_6$, $COOR_6$,
  saturated or unsaturated hydrocarbon-based rings having 4 to 7 atoms, it being possible for these rings to be optionally substituted with at least one substituent $T_4$ selected from A and R;

$R_6$, and $R'_6$ are selected from among:
  hydrogen,
  saturated or unsaturated, linear or branched $C_1$-$C_{20}$ alkyl radicals optionally substituted with at least one substituent R',
  saturated or unsaturated rings having 4 to 7 atoms, optionally containing at least one hetero atom selected from among O, N and S, it being possible for these rings to be optionally attached and/or to be substituted with at least one substituent R;

R is selected from among:
  saturated or unsaturated, linear or branched $C_1$-$C_{20}$ alkyl radicals,
  halogens,
  the groups $OR_7$, $SR_7$, $NR_7R'_7$, CN, $CF_3$, $COOR_7$;

R' is selected from among:
saturated or unsaturated, linear or branched $C_1$-$C_{20}$ alkyl radicals,
halogens,
the groups $OR_7$, $SR_7$, $NR_7R'_7$, CN, $CF_3$, $COOR_7$,
saturated or unsaturated rings having 4 to 7 atoms, optionally containing at least one hetero atom selected from among O, N and S, it being possible for these rings to be optionally attached;
$R_7$ and $R'_7$ independently represent hydrogen or a saturated or unsaturated, linear or branched $C_1$-$C_{20}$ alkyl;
A is a saturated or unsaturated, linear or branched $C_1$-$C_{20}$ alkyl radical optionally substituted with at least one substituent $T_5$ selected from among halogens, the groups $OR_7$, $SR_7$, $NR_7R'_7$, CN, $CF_3$ and $COOR_7$, and saturated or unsaturated rings having 4 to 7 atoms, optionally containing at least one hetero atom selected from among O, N and S, it being possible for these rings to be optionally attached and/or to be substituted with at least one substituent R;
$T_1$ is selected from among $OR_6$, $SR_6$, $NR_6R'_6$, CN, $CF_3$, $COOR_6$, halogens, and saturated or unsaturated rings having 4 to 7 atoms, optionally containing at least one hetero atom selected from among O, N and S, it being possible for these rings to be optionally attached and to be substituted with at least one substituent R.

According to one embodiment of the invention, at least one of $R_1$ and $R_2$ is a saturated $C_1$-$C_{20}$, and better still $C_1$-$C_{10}$, alkyl radical substituted with $SR_6$ or OH. In particular, $R_6$ is a $C_1$-$C_{20}$, and better still $C_1$-$C_{10}$, alkyl radical optionally substituted with a heterocycle Hy having 4 to 7 atoms. For example, at least one of $R_1$ and $R_2$ is a group $(CH_2)_nS_nR_8$ with $R_8$ representing OH or $-S-(CH_2)_mR_9$, with $R_9$ representing H or $Hy(CH_2)_mHy$, where n and m each represent an integer ranging from 1 to 20, and better still from 1 to 10. In particular, $R_1$ is hydrogen and $R_2$ is $(CH_2)_mS(CH_2)_mR_9Hy$, with n having the value 2 and m having the value 1. For example, Hy is a heterocycle having 5 atoms, containing, for example, oxygen as hetero atom, for instance furan.

Advantageously, at least one of $R_3$ and $R_5$ is $CF_3$. In particular, $R_3$ is $CF_3$ and $R_5$ is H.

According to a particular embodiment, $R_4$ is a hydrocarbon-based ring containing 5 to 6 atoms, which is in particular unsaturated, and especially a phenyl radical optionally substituted with $T_4$, and for example with 4-COOH.

According to a particular embodiment of the invention, the pyrazolecarboxamide compound has the following formula (III) or is one of its salts:

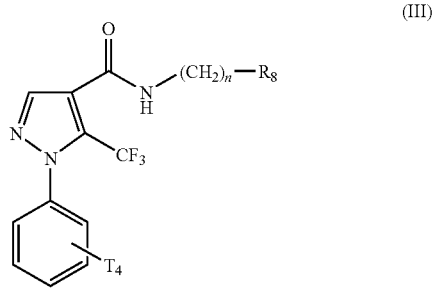

(III)

where $R_8$ is OH or $-S-(CH_2)_m-R_9$, with $R_9$ representing H or Hy; $T_4$ is H or 4-COOH; n and m independently represent an integer ranging from 1 to 10, and better still from 1 to 5; Hy representing a heterocycle in particular having 5 to 6 atoms.

According to the invention, the expression "salts of a compound of formula (I)" means the organic or inorganic salts of a compound of formula (I).

As inorganic salts that can be used according to the invention, mention may be made of: sodium or potassium salts, and also zinc ($Zn^{2+}$) salts, calcium ($Ca^{2+}$) salts, copper ($Cu^{2+}$) salts, iron ($Fe^{2+}$) salts, strontium ($Sr^{2+}$) salts, magnesium ($Mg^{2+}$) salts, manganese ($Mn^{2+}$) salts, ammonium salts; hydroxides, carbonates, halides, chlorides, sulfates, phosphates or nitrates.

The organic salts that can be used according to the invention are, for example, triethanolamine salts, monoethanolamine salts, diethanolamine salts, hexadecylamine salts, N,N,N',N'-tetrakis(2-hydroxy-propyl)ethylenediamine salts or trishydroxymethylaminomethane salts.

The compounds of formula (I) are salified or nonsalified, some of which are known as such. They can be produced in a known manner, and in particular as described in the document T. W. Waldrep et al., *J. Agr. Food Chem.*, 1990, 38, 541-544. They are in a solid form, in particular a pulverulent form.

To provide an order of magnitude according to the invention, the compound of formula (I) or one of its salts or mixture of compounds of formula (I) and/or of their salt can be used in an amount representing from $10^{-3}$% to 10% of the total weight of the composition, and preferably in an amount representing from $10^{-3}$% to 5%, and better still from $10^{-2}$% to 2% of the total weight of the composition, for example from 0.5% to 2%.

The compositions of the invention may be for cosmetic or pharmaceutical use. Preferably, the composition of the invention is for cosmetic use. Thus, the composition should contain a non-toxic physiologically acceptable medium that can be applied to the skin, including the scalp and the eyelids, or to the keratin fibers of human beings. For the purpose of the invention, the term "cosmetic" means a composition with a pleasant appearance, smell and feel.

The compounds of formula (I), which may be salified or nonsalified, can be used in a composition that must be ingested, injected or applied to the skin or to keratin fibers (to any area of the skin or fibers to be treated).

According to the invention, the compound of formula (I) can be administered orally in an amount of from 0.1 to 300 mg per day, 5 to 10 mg/d.

A preferred composition of the invention is a composition for cosmetic use, and in particular for topical application to the skin and keratin fibers, and more especially to the scalp, the hair and the eyelashes.

This composition may be in any of the known pharmaceutical forms suitable for the method of use.

2-Alkylideneaminooxyacetamide Compounds:

According to yet another embodiment, 15-PGDH inhibitors that are useful according to the invention comprise certain 2-alkylideneaminooxyacetamide compounds, and in particular certain thiophene- or furan-aminooxyacetamides, that may be salified or nonsalified. The present invention therefore also features the administration of at least one 2-alkylideneaminooxyacetamide compound of formula (I) or of one of its salts:

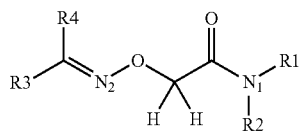
(I)

in which:
a) $R_1$ and $R_2$ are selected independently from among:
1) saturated or unsaturated, linear or branched $C_1$-$C_{20}$ alkyl radicals optionally substituted with at least one substituent $T_1$ selected from among:
halogens,
the groups $CF_3$, CN, OR, SR, NRR', NRC(=NR')NR''R''', COR, CSR, COOR, CONRR', NRCOR', NRCONR'R'', $SO_2NRR'$, $NRSO_2R'$, $SO_2R$, SiRR'R'',
saturated or unsaturated rings having 4 to 7 atoms, optionally containing at least one hetero atom so as to form a heterocycle Hy, it being possible for these rings to be optionally attached, to contain a carbonyl or thiocarbonyl function and/or to be substituted with at least one substituent $T_2$,
2) saturated or unsaturated rings having 4 to 7 atoms, optionally containing at least one hetero atom so as to form a heterocycle Hy, it being possible for these rings to be optionally attached, to contain a carbonyl or thiocarbonyl function and/or to be substituted with at least one substituent $T_3$ selected from among:
halogens,
the groups $CF_3$, CN, OR, SR, NRR', NRC(=NR')NR''R''', COR, CSR, COOR, CONRR', NRCOR', NRCONR'R'', $SO_2NRR'$, $NRSO_2R'$, $SO_2R$, SiRR'R'',
saturated or unsaturated, linear or branched $C_1$-$C_{20}$ alkyl radicals optionally substituted with at least one substituent $T_1$,
saturated or unsaturated rings having 4 to 7 atoms, optionally containing at least one hetero atom so as to form a heterocycle Hy, it being possible for these rings to be optionally attached, to contain a carbonyl or thiocarbonyl function and/or to be substituted with at least one substituent $T_2$;

with the proviso that, when $R_1$ and $R_2$ are both heterocycles Hy, at least one heterocycle is attached to the nitrogen $N_1$ of formula (I) via a carbon;
3) the groups CN, C(=NR)R', C(=NR)NR'R'', COR, CSR, COOR, CONRR';
4) $R_1$ may also be a hydrogen atom or a group $SO_2R$ or $SO_2NRR'$;
5) $R_1$ and $R_2$ may also form a heterocycle Hy, optionally substituted with at least one substituent $T_2$ and optionally attached to an aryl radical or to a saturated or unsaturated carbon ring having 4 to 7 atoms and possibly containing a carbonyl or thiocarbonyl function, or attached to another heterocycle Hy;
b) $R_3$ and $R_4$ are selected independently from among:
1) linear or branched $C_1$-$C_{20}$ alkyl radicals or carbon rings having 4 to 7 atoms, possibly containing a carbonyl or thiocarbonyl function, these alkyl groups or these rings being saturated or unsaturated, and optionally substituted with at least one substituent $T_4$ selected chosen from among:
halogens,
the groups $CF_3$, CN, OR, SR, NRR', NRC(=NR')NR''R''', COR, CSR, COOR, CONRR', NRCOR', NRCONR'R'', $SO_2NRR'$, $NRSO_2R'$, $SO_2R$, SiRR'R'',
aryl radicals or heterocycles Hy, these radicals and heterocycles being optionally substituted with at least one substituent $T_2$ and optionally attached to an aryl radical or to a carbon ring, that is saturated or unsaturated, has 4 to 7 atoms, and may contain a carbonyl or thiocarbonyl function, or attached to another heterocycle Hy;
2) aryl radicals or heterocycles Hy, these aryl radicals and these heterocycles being optionally attached to any aryl radical or to a carbon ring, that is saturated or unsaturated, has 4 to 7 atoms, and may contain a carbonyl or thiocarbonyl function, or attached to a heterocycle Hy, these aryl radicals, this carbon ring or these heterocycles Hy being optionally substituted with at least one substituent $T_3$;
3) the groups $CF_3$, CN, OR, SR, NRR', NRC(=NR')NR''R''', COR, CSR, COOR, $CH_2COOR$, CONRR', NRCOR', NRCONR'R'', $SO_2NRR'$, $NRSO_2R'$, $SO_2R$, SiRR'R'';
4) $R_3$ and $R_4$ may also be a hydrogen atom;
c) R, R', R'' and R''', which may be identical or different, denote one of the following groups:
a hydrogen,
a saturated or unsaturated, linear or branched $C_1$-$C_{20}$ alkyl radical optionally substituted with at least one substituent $T_2$,
saturated or unsaturated rings having 4 to 7 atoms, optionally containing at least one hetero atom so as to form a heterocycle Hy, it being possible for these rings to be optionally attached, to contain a carbonyl or thiocarbonyl function and/or to be substituted with at least one substituent $T_2$;
d) $T_2$ is:
saturated or unsaturated, linear or branched $C_1$-$C_{20}$ alkyl radical,
a halogen,
a group selected from among CN, $CF_3$, $OR_5$, $SR_5$, $NR_5R_6$, $NR_5C(=NR_6)NR_7R_8$, $COR_5$, $CSR_5$, $COOR_5$, $CH_2COOR_5$, $CONR_5R_6$, $NR_5COR_6$, $NR_5CONR_5R_7$, $SO_2NR_5R_6$, $NRSO_2R_5$, $SO_2R_5$, $SiR_5R_6R_7$, in which $R_5$, $R_6$, $R_7$ and $R_8$, which may be identical or different, denote hydrogen or a saturated or unsaturated, linear or branched $C_1$-$C_{20}$ alkyl radical,
an aryl radical or a heterocycle Hy optionally attached to an aryl radical or to a carbon ring, that is saturated or unsaturated and has 4 to 7 atoms, or attached to another heterocycle Hy;
e) Hy is a saturated or unsaturated heterocycle having 4 to 7 atoms that may contain from 1 to 4 hetero atoms selected from N, O and S, and/or may contain a carbonyl or thiocarbonyl function.

The invention also applies to the keratin fibers of mammals of the animal species (dog, horse, sheep or cat, for example).

This invention also features the cosmetic use of at least one oxyacetamide of formula (I), or of one of its salts, in a cosmetic care and/or makeup composition for human keratin fibers, for inducing and/or stimulating pigmentation thereof, or impairing whitening thereof, and also to the use of at least one compound of formula (I), or of one of its salts, for preparing a care composition or a treatment composition for human keratin fibers, useful to induce and/or stimulate pigmentation of the fibers and/or impair whitening thereof.

The human keratin fibers to which the invention applies are in particular the hair, the eyebrows, the eyelashes, beard hair, moustache hair and pubic hair. More especially, the present invention applies to human hair and/or to human eyelashes.

Thus, the present invention also features a care or makeup composition for keratin fibers, in particular a haircare or mascara composition, for topical application, containing a physiologically acceptable medium and an effective amount of at least one compound of formula (I) or of one of its salts, as described above.

This invention also features the use, in particular cosmetic use, of at least one 2-alkylideneaminooxyacetamide compound of formula (1), or of one of its salts, as defined above, as an agent for inducing and/or stimulating pigmentation of keratin fibers, in particular human keratin fibers, and/or of the skin.

In the following text, and unless expressly mentioned, the use of the term "compound of formula (I)" should be understood to mean both the compound of formula (I) in neutral, acidic or basic form, and in the form of salts.

According to the invention, the term "at least one" means one or more (2, 3 or more). In particular, the composition may contain one or more compounds of formula (I). This or these compounds may be cis or trans or Z or E isomers or a mixture of cis/trans or Z/E isomers. They may also be in tautomeric form. This or these compounds may be enantiomers and/or diastereoisomers or a mixture of these isomers, in particular a racemic mixture.

For the purpose of the invention, the term "alkyl radical" means a hydrocarbon-based radical that may be linear or branched and saturated or unsaturated. Preferably, the alkyl radical contains from 1 to 10 carbon atoms.

According to the invention, the rings employed for $R_1$, $R_2$, $R_3$, $R_5$, $R_6$, $R_7$, $R_8$, R, R', R", R'", $T_1$, $T_2$ and $T_3$ contain from 4 to 7 atoms, and better still from 5 to 6 atoms. They may be saturated or unsaturated and may optionally comprise one or more hetero atoms such as S, N or O, or combinations thereof. The rings may also contain one or more carbonyl functions or thiocarbonyl functions or both, the carbon of these functions being part of the heterocycle. As saturated carbon rings that can be used, mention may be made of the cyclobutyl, cyclopentyl, cyclohexyl or cycloheptyl radical. As heterocycles Hy, mention may be made of pyridine, piperidine, morpholine, pyrrole, furan, thiophene, imidazole, oxazole, thiazole, pyrazole, pyrimidine, piperazine, pyrazine, pyridazine, triazine, pyrrolidine or thiazolidine rings. As unsaturated carbon rings, mention may be made of the cyclohexenyl or phenyl ring, and as aryl radicals, mention may be made of the phenyl or naphthyl radical. In addition, these rings may be substituted, in particular with a substituent $T_2$.

Furthermore, these rings may be alone or attached to another ring whose chemical structure is the same or different, and may thus form fused rings.

For all the definitions of $R_1$ to $R_8$ and of R, R', R" and R'", certain carbons of the saturated or unsaturated carbon rings or heterocycles having 4, 5, 6 or 7 atoms may also be part of a carbonyl or thiocarbonyl function, for instance:

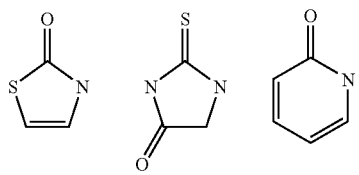

Where $R_1$ and $R_2$ form a heterocycle, this heterocycle may, for example, be the pyrrolidine, pyrrole, imidazole, triazole, piperidine, morpholine, piperazine or tetrazole ring.

As an example of an alkyl radical that can be used in the invention, exemplary are methyl, ethyl, isopropyl, n-butyl, tert-butyl, n-hexyl, 2-ethylhexyl or alternatively ethylene or propylene radicals. This radical may be optionally substituted with one or more substituents $T_4$, for example selected from among OR and COOR.

As a halogen atom, exemplary are chlorine, fluorine or bromine atoms, and better still fluorine and chlorine atoms.

According to the invention, the compounds of formula (I) are in isolated form, i.e., nonpolymeric form.

According to one embodiment, at least one of $R_3$ and $R_4$ is a saturated $C_1$-$C_{20}$, and better still $C_1$-$C_{10}$, alkyl radical group, for instance the methyl or ethyl radical, or a heterocycle Hy. For example, at least one of $R_3$ and $R_4$ is a saturated $C_1$-$C_{20}$ alkyl radical and the other a heterocycle Hy. In particular, $R_3$ is the methyl or ethyl radical and $R_4$ is a heterocycle having 5 atoms. For example Hy is a heterocycle having 5 atoms, containing for example sulfur or oxygen as hetero atom, for instance thiophene or furan.

Advantageously, at least one of $R_1$ and $R_2$ is a hydrogen atom, a saturated or unsaturated carbon ring and in particular an aryl radical. In particular, $R_2$ is H and $R_1$ is a phenyl radical optionally substituted with an alkyl or an alkoxy such as the methoxy group.

According to the invention, the expression "salts of a compound of formula (I)" means the simple or double, organic or inorganic salts of a compound of formula (I).

As inorganic salts that can be used according to the invention, mention may be made of: sodium salts and potassium salts, and also zinc ($Zn^{2+}$) salts, calcium ($Ca^{2+}$) salts, copper ($Cu^{2+}$) salts, iron ($Fe^{2+}$) salts, strontium ($Sr^{2+}$) salts, magnesium ($Mg^{2+}$) salts, ammonium salts and manganese ($Mn^{2+}$) salts; hydroxides, carbonates, halides, sulfates, nitrates or phosphates.

The organic salts that can be used according to the invention are, for example, triethanolamine salts, monoethanolamine salts, diethanolamine salts, hexadecylamine salts, N,N,N',N'-tetrakis(2-hydroxy-propyl)ethylenediamine salts and trishydroxymethylaminomethane salts.

The compounds of formula (I), which may be salified or nonsalified, are known as such and can be prepared in the known manner. For example, the synthesis can be carried out in three steps. The condensation of a ketone with hydroxylamine hydrochloride gives an oxime. The latter can be alkylated with the sodium salt of 2-chloroacetic acid. The acid formed is then converted to an amide via the formation of an acid chloride and reaction of the latter with an amine. Such a preparation is described by A. Buzas et al., *Chimie Thérapeutique [Therapeutic Chemistry]*, 1972, 2, 140-142.

To provide an order of magnitude according to the invention, the compound of formula (I) or one of its salts or a mixture of compounds of formula (I) and/or of their salts can be used in an amount representing from $10^{-3}$% to 10% of the total weight of the composition, and preferably in an amount representing from $10^{-3}$% to 5%, and better still from $10^{-2}$% to 2% of the total weight of the composition, for example from 0.5% to 2%.

According to the invention, the compound of formula (I) can be administered orally in an amount of from 0.1 to 300 mg per day, 5 to 10 mg/d.

2-Thioacetamide Compounds:

According to another embodiment, the 15-PGDH inhibitor according to the invention comprises at least one 2-thioacetamide compound of formula (I) or one of its salts:

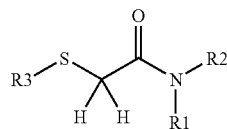

in which:
a) $R_1$ and $R_2$ independently represent:
1) a hydrogen atom,
2) a $C_1$-$C_{20}$ alkyl radical optionally substituted with at least one substituent $A_1$,
3) a hydrocarbon-based ring $C_1$, optionally attached to a ring $C_2$ optionally containing at least one hetero atom so as to form a heterocycle $Hy_1$, it being possible for these rings $C_1$ and $C_2$ to contain at least one carbonyl or thiocarbonyl function and to be substituted with at least one substituent $A_3$,
4) a heterocycle $Hy_2$, optionally attached to a ring $C_2$ optionally containing at least one hetero atom so as to form a heterocycle $Hy_3$, it being possible for these rings $Hy_2$ and $C_2$ to contain a carbonyl or thiocarbonyl function and to be substituted with at least one substituent $A_3$, or
5) a group C(=NR)R', C(=NR)NR'R", COR, CSR, COOR, CONRR', $SO_2R$ or $SO_2NRR'$;
b) $R_3$ is:
1) a $C_1$-$C_{20}$ alkyl radical optionally substituted with at least one substituent $A_2$,
2) a hydrocarbon-based ring $C_3$, optionally attached to a ring $C_4$ optionally containing at least one hetero atom so as to form a heterocycle $Hy_3$, it being possible for these rings $C_3$ and $C_4$ to contain at least one carbonyl or thiocarbonyl function and to be substituted with at least one substituent $A_3$,
3) a heterocycle $Hy_4$ representing a pyrrole, furan, thiophene or pyrazole ring, optionally attached to a ring $C_5$ representing a phenyl, pyridine or pyrimidine ring, it being possible for these two rings $Hy_4$ and $C_5$ to be substituted with at least one substituent $A_3$,
4) a pyridine ring optionally attached to a ring $C_2$ optionally containing at least one hetero atom so as to form a heterocycle $Hy_1$, it being possible for this pyridine ring and this ring $C_2$ to contain at least one carbonyl or thiocarbonyl function and to be substituted with at least one substituent $A_4$,
5) a heterocycle $Hy_5$ that is different from $Hy_4$ and from the pyridine ring, optionally attached to a ring $C_2$ optionally containing at least one hetero atom so as to form a heterocycle $Hy_1$, it being possible for these rings $Hy_5$ and $C_2$ to contain at least one carbonyl or thiocarbonyl function and to be substituted with at least one substituent $A_3$, or
6) a group C(=NR)R', C(=NR)NR'R", COR, CSR, COOR or CONRR';
c) $A_1$ is:
1) a halogen,
2) a group $CF_3$, CN, OR, SR, NRR', NRC(=NR')NR"R', COR, CSR, COOR, CONRR', CSNRR'NRCSR', NRCSNR'R", NRCOR', NRCONR'R", $SO_2NRR'$, $NRSO_2R'$, $SO_2R$ or SiRR'R",
3) a hydrocarbon-based ring $C_6$, optionally attached to a ring $C_7$ optionally containing at least one hetero atom so as to form a heterocycle $Hy_6$, it being possible for these rings $C_6$ and $C_7$ to contain at least one carbonyl or thiocarbonyl function and to be substituted with at least one substituent $A_5$,
4) a heterocycle $Hy_7$ optionally attached to a ring $C_7$ optionally containing at least one hetero atom so as to form a heterocycle $Hy_6$, it being possible for these rings $Hy_7$ and $C_7$ to contain at least one carbonyl or thiocarbonyl function and to be substituted with at least one substituent $A_5$;
d) $A_2$ is:
1) a halogen,
2) a group $CF_3$, CN, OR, SR, NRR', NRC(=NR')NR"R', COR, CSR, COOR, CONRR', CSNRR', NRCSR', NRCSNR'R", NRCOR', NRCONR'R", $SO_2NRR'$, $NRSO_2R'$, $SO_2R$ or SiRR'R", or
3) a ring $C_8$, optionally attached to a ring $C_9$, these rings $C_8$ and $C_9$ optionally containing at least one hetero atom so as to form a heterocycle $Hy_8$ and/or at least one carbonyl or thiocarbonyl function and/or being substituted with at least one substituent $A_5$;
e) $A_3$ is:
1) $A_2$, or
2) a $C_1$-$C_{20}$ alkyl group, optionally substituted with at least one substituent $A_5$;
f) $A_4$ is:
1) a halogen,
2) a group $CF_3$, CN, OR, SR, NRC(=NR')NR"R', COR, CSR, COOR, CONRR', CSNRR', NRCSR', NRCSNR'R", NRCOR', NRCONR'R", $SO_2NRR'$, $NRSO_2R'$, $SO_2R$ or SiRR'R",
3) a $C_1$-$C_{20}$ alkyl group optionally substituted with at least one substituent $A_5$,
4) a ring $C_8$ optionally attached to a ring $C_9$, these rings $C_8$ and $C_9$ optionally containing at least one hetero atom so as to form a heterocycle $Hy_8$ and/or at least one carbonyl or thiocarbonyl function and/or being substituted with at least one substituent $A_5$;
g) $A_4$ is:
1) a halogen,
2) a group $CF_3$, CN, $OR_5$, $SR_5$, $NR_5R'_5$, $NR_5C(=NR_5')NR"_5R'"_5$, $COR_5$, $CSR_5$, $COOR_5$, $CONR_5R'_5$, $CSNR_5R'_5$, $NR_5CSR'_5$, $NR_5CSNR'_5R"_5$, $NR_5COR'_5$, $NR_5CONR'_5R"_5$, $SO_2NR_5R'_5$, $NR_5SO_2R'_5$, $SO_2R_5$ or $SiR_5R'_5R"_5$, $R_5$, $R'_5$ and $R"_5$ being a hydrogen atom or a $C_1$-$C_{20}$ alkyl group,
3) a $C_1$-$C_{20}$ alkyl group, or
4) a ring $C_{10}$, optionally attached to another ring $C_{11}$, these rings optionally containing at least one hetero atom so as to form a heterocycle $Hy_9$ and/or containing at least one carbonyl or thiocarbonyl function;
h) R, R', R" and R', which may be identical or different, represent:
1) a hydrogen atom,
2) a $C_1$-$C_{20}$ alkyl group optionally substituted with at least one substituent $A_5$, or
3) a ring $C_{12}$ optionally attached to another ring $C_{13}$, these rings optionally containing at least one hetero atom so as to form a heterocycle $Hy_{10}$ and possibly being substituted with at least one substituent $A_5$;
i) $Hy_1$ to $Hy_{10}$ independently represent a heterocycle that may contain from 1 to 4 hetero atoms selected from N, O and S.

The invention also relates to the use, in particular cosmetic use, of at least one 2-thioacetamide compound of formula (I), or of one of its salts, as defined above, as an agent for inducing and/or stimulating pigmentation of human keratin fibers, in particular the eyelashes and/or the hair, and/or of the skin.

In the subsequent text, and unless expressly mentioned, the use of the term "compound of formula (I)" should be understood to mean both the compound of formula (I) in the form of an acid or of a base, and one of its salts. It may also be in tautomeric form.

According to the invention, the term "at least one" means one or more (2, 3 or more). In particular, the composition may contain one or more compounds of formula (I). This or these compounds may be cis or trans isomers or a mixture of cis/trans isomers. They may also be in tautomeric form. This or these compounds may be enantiomers and/or diastereoisomers or a mixture of these isomers, in particular a racemic mixture.

For the purpose of the invention, the term "hydrocarbon-based" means a group of hydrogen and carbon atoms.

For the purpose of the invention, the term "alkyl radical" means a hydrocarbon-based radical that may be linear or branched and saturated or unsaturated. In particular, the alkyl radical contains from 1 to 20 carbon atoms, preferably from 1 to 10. As examples of alkyl radicals that can be used in the invention, mention may be made of methyl, ethyl, isopropyl, n-butyl, tert-butyl, n-hexyl, 2-ethylhexyl, ethylene or propylene radicals.

According to the invention, the rings $C_1$ to $C_{13}$, $Hy_2$, $Hy_4$ and $Hy_5$ of formula (I) contain from 3 to 7 atoms, and better still from 5 to 6 atoms, and may be saturated or unsaturated. In addition, the rings $C_2$, $C_4$, $C_7$, $C_8$, $C_9$, $C_{10}$, $C_{11}$, $C_{12}$ and $C_{13}$ may optionally comprise one or more hetero atoms such as S, N or O, or combinations thereof, and may thus form heterocycles. $Hy_7$ is a heterocycle that may contain from 1 to 4 hetero atoms selected from N, S and O, and a combination thereof, and that contains from 3 to 15 atoms, and better still from 5 to 6 atoms. According to a particular embodiment of the invention, the heterocycle $Hy_7$ may contain up to 15 atoms, such as a crown ether having 5 —$CH_2CH_2O$— units. These rings may also be attached to another ring whose chemical nature is identical or different. In addition, these rings may be substituted, in particular with a substituent $A_3$ or $A_5$.

As saturated hydrocarbon-based rings that can be used in the invention, mention may be made of the cyclopropyl, cyclobutyl, cyclopentyl, cyclohexyl or cycloheptyl radical. As unsaturated hydrocarbon-based rings, mention may be made of the cyclohexenyl or phenyl ring. As attached hydrocarbon-based rings that can be used, mention may be made of the naphthyl radical.

According to the invention, $R_1$ and/or $R_2$ may represent a hydrocarbon-based ring as defined above, that is in particular saturated. According to the invention, $R_1$ and/or $R_2$ may also represent a heterocycle $Hy_2$ containing from 3 to 7 atoms, and better still from 5 to 6 atoms, and containing from 1 to 4 hetero atoms selected from N, O and S, and a combination thereof. This heterocycle may in addition contain one or more carbonyl or thiocarbonyl functions. By way of example, $Hy_2$ is one of the following heterocycles: azetidine, pyrrole, dihydropyrrole, pyrrolidine, furan, dihydrofuran, tetrahydrofuran, thiophene, dihydrothiophene, tetrahydrothiophene, imidazole, dihydroimidazole, imidazolidine, dihydrothiazole, thiazolidine, dihydropyrazole, pyrazolidine, oxazole, dihydrooxazole, oxazolidine, isoxazole, dihydroisoxazole, isoxazolidine, isothiazole, dihydroisothiazole, isothiazolidine, triazole, dihydrotriazole, triazolidine, oxadiazole, dihydrooxadiazole, oxadiazolidine, thiadiazole, dihydrothiadiazole, thiadiazolidine, tetrazole, pyridine, dihydropyridine, tetrahydropyridine, piperidine, pyran, dihydropyran, tetrahydropyran, pyrimidine, dihydropyrimidine, tetrahydropyrimidine, piperazine, pyridazine, pyrazine, triazine, morpholine, azepine or diazepine. Preferably, $Hy_2$ is a piperidine ring. This heterocycle $Hy_2$ may also be attached to a saturated or unsaturated ring $C_2$ having 4 to 7 atoms, $C_2$ optionally containing at least one hetero atom selected from among O, N and S so as to form a heterocycle $Hy_1$. $C_2$ may also contain one or more carbonyl or thiocarbonyl functions. As an example of a heterocycle Hy, that can be used in the invention, mention may be made of pyridine, piperidine, morpholine, pyrrole, furan, thiophene, imidazole, oxazole, thiazole, pyrazole, pyrimidine, piperazine, pyrazine, pyridazine, triazine, pyrrolidine or thiazolidine rings.

According to the invention, $R_1$ and/or $R_2$ may also represent an alkyl radical in which at least one of the hydrogens is substituted with a heterocycle $Hy_7$. This heterocycle may contain from 3 to 7 atoms, and better still from 5 to 6 atoms, and may comprise from 1 to 4 hetero atoms selected from N, O and S, and a combination thereof. According to a particular embodiment of the invention, this heterocycle $Hy_7$ may contain up to 15 atoms, such as a crown ether comprising 5 —$CH_2CH_2O$— units. According to another embodiment, $Hy_7$ contains a carbonyl function. As heterocycles $Hy_7$ that can be used in the invention, mention may be made of the following rings: azetidine, pyrrole, dihydropyrrole, pyrrolidine, furan, dihydrofuran, tetrahydrofuran, thiophene, dihydrothiophene, tetrahydrothiophene, imidazole, dihydroimidazole, imidazolidine, thiazole, dihydrothiazole, thiazolidine, pyrazole, dihydropyrazole, pyrazolidine, oxazole, dihydrooxazole, oxazolidine, isoxazole, dihydroisoxazole, isoxazolidine, isothiazole, dihydroisothiazole, isothiazolidine, triazole, dihydrotriazole, triazolidine, oxadiazole, dihydrooxadiazole, oxadiazolidine, thiadiazole, dihydrothiadiazole, thiadiazolidine, tetrazole, pyridine, dihydropyridine, tetrahydropyridine, pyran, dihydropyran, tetrahydropyran, pyrimidine, dihydropyrimidine, tetrahydropyrimidine, piperazine, pyridazine, pyrazine, triazine, morpholine, azepine, diazepine, a crown ether comprising 15 atoms and 5 —$CH_2CH_2O$— units, or pyrrolidinone. Preferably, $Hy_7$ is one of the following rings: pyrrole, oxyazole, pyridine, furan, pyrrolidine, morpholine, tetrahydrofuran, a crown ether comprising 15 atoms (5 —$CH_2CH_2O$— units), or pyrrolidinone.

According to the invention, $R_3$ may represent a saturated or unsaturated hydrocarbon-based ring $C_3$ having 3 to 7 carbon atoms, and better still 5 to 6 carbon atoms, optionally attached to a heterocycle $Hy_3$. This heterocycle $Hy_3$ may contain from 4 to 7 atoms, and better still from 5 to 6 atoms, and may comprise from 1 to 4 hetero atoms selected from N, O and S, and a combination thereof. In addition, this heterocycle $Hy_3$ may contain one or more carbonyl or thiocarbonyl functions.

As heterocycles $Hy_3$ that can be used in the invention, mention may be made of azetidine, pyrrole, dihydropyrrole, pyrrolidine, furan, dihydrofuran, tetrahydrofuran, thiophene, dihydrothiophene, tetrahydrothiophene, imidazole, dihydroimidazole, imidazolidine, dihydrothiazole, thiazolidine, pyrazole, dihydropyrazole, pyrazolidine, oxazole, dihydrooxazole, oxazolidine, isoxazole, dihydroisoxazole, isoxazolidine, isothiazole, dihydroisothiazole, isothiazolidine, triazole, dihydrotriazole, triazolidine, oxadiazole, dihydrooxadiazole, oxadiazolidine, thiadiazole, dihydrothiadiazole, thiadiazolidine, tetrazole, pyridine, dihydropyridine, tetrahydropyridine, piperidine, pyran, dihydropyran, tetrahydropyran, pyrimidine, dihydropyrimidine, tetrahydropyrimidine, piperazine, pyridazine, pyrazine, triazine, morpholine, azepine or diazepine rings. Preferably, $Hy_3$ is one of the following rings: pyrrole, pyridine, pyrimidine, imidazole, triazole, furan, thiophene, oxazole or thiazole.

According to the invention, $R_3$ may also represent:
a pyridine ring optionally attached to a ring $C_2$ whose chemical nature is identical or different,
a heterocycle $Hy_4$ selected from pyrrole, furan, thiophene and pyrazole rings, optionally attached to a phenyl, pyridine or pyrimidine ring, another heterocycle $Hy_5$ containing from 3 to 7 atoms, and better still from 5 to 6 atoms, and containing from 1 to 4 hetero atoms selected from N, O and S, and a combination thereof. This heterocycle $Hy_5$ may also contain one or more carbonyl or thiocarbonyl functions and may be attached to another ring $C_2$ whose chemical nature is identical or different.

By way of example, the heterocycle $Hy_5$ is selected from among azetidine, dihydropyrrole, pyrrolidine, dihydrofuran, tetrahydrofuran, dihydrothiophene, tetrahydrothiophene, imidazole, dihydroimidazole, imidazolidine, thiazole, dihydrothiazole, thiazolidine, dihydropyrazole, pyrazolidine, oxazole, dihydrooxazole, oxazolidine, isoxazole, dihydroisoxazole, isoxazolidine, isothiazole, dihydroisothiazole, isothiazolidine, triazole, dihydrotriazole, triazolidine, oxadiazole, dihydrooxadiazole, oxadiazolidine, thiadiazole, dihydrothiadiazole, thiadiazolidine, tetrazole, dihydropyridine, tetrahydropyridine, piperidine, pyran, dihydropyran, tetrahydropyran, pyrimidine, dihydropyrimidine, tetrahydropyrimidine, piperazine, pyridazine, pyrazine, triazine, morpholine, azepine, diazepine, 2-benzothiazolyl and thiazolo[2,3-c][1,2,4]triazole rings. Preferably, $Hy_5$ is one of the following rings: 2-benzothiazolyl, thiazolo[2,3-c][1,2,4]triazole, imidazole, thiazole, triazole, oxazole, pyrimidine, pyrazine or pyridazine.

As examples of heterocycles $Hy_1$, $Hy_6$, $Hy_8$, $Hy_9$ and $Hy_{10}$ that can be used according to the invention, mention may be made, independently, of azetidine, pyrrole, dihydropyrrole, pyrrolidine, furan, dihydrofuran, tetrahydrofuran, thiophene, dihydrothiophene, tetrahydrothiophene, imidazole, dihydroimidazole, imidazolidine, thiazole, dihydrothiazole, thiazolidine, pyrazole, dihydropyrazole, pyrazolidine, oxazole, dihydrooxazole, oxazolidine, isoxazole, dihydroisoxazole, isoxazolidine, isothiazole, dihydroisothiazole, isothiazolidine, triazole, dihydrotriazole, triazolidine, oxadiazole, dihydrooxadiazole, oxadiazolidine, thiadiazole, dihydrothiadiazole, thiadiazolidine, tetrazole, pyridine, dihydropyridine, tetrahydropyridine, piperidine, pyran, dihydropyran, tetrahydropyran, pyrimidine, dihydropyrimidine, tetrahydropyrimidine, piperazine, pyridazine, pyrazine, triazine, morpholine, azepine and diazepine rings. Pyrrole, pyrrolidine, imidazole, furan, pyrazole, pyridine, pyrimidine, triazole, pyrazine, pyridazine, piperidine, piperazine or morpholine rings are preferably used.

The heterocycles of formula (I) may also be attached to a ring whose chemical nature is identical or different.

As attached heterocycles that can be used in the invention, mention may be made of purine or pteridine rings. As heterocycles attached to a hydrocarbon-based ring that can be used in the invention, mention may be made of benzofuran, benzothiophene, benzothiazole, indole, benzimidazole, quinoline, isoquinoline or quinazoline radicals.

As halogen atoms that can be used in the invention, exemplary are chlorine, fluorine or bromine atoms, and better still fluorine and chlorine atoms.

According to the invention, the compounds of formula (I) are in isolated form, i.e., nonpolymeric form.

According to a particular embodiment of the invention, at least one of $R_1$ and $R_2$ is a hydrogen atom; a $C_1$-$C_{20}$ alkyl radical in which at least one hydrogen is substituted with at least one substituent $A_1$; a saturated or unsaturated hydrocarbon-based ring having 3 to 6 carbon atoms, in which at least one hydrogen is optionally substituted with the halogen group such as $CF_3$ or halogen atoms, and in particular with 1 or 2 chlorine or bromine atoms when the ring is a phenyl. This group and these halogen atoms may be situated in the para-, meta- or ortho-position with respect to the nitrogen atom bearing $R_1$ and $R_2$. The hydrocarbon-based ring is in particular a cyclopentyl, cyclopropyl, cyclobutyl or cyclohexyl radical, or an aryl radical such as phenyl. In particular, $R_1$ is H and $R_2$ is a cyclopentyl, cyclopropyl, cyclobutyl or cyclohexyl radical or a phenyl radical substituted with a bromine atom or 2 chlorine atoms.

According to another embodiment, $R_1$ is H and $R_2$ is a saturated or unsaturated heterocycle having 5 to 6 atoms, containing from 1 to 4 hetero atoms selected from N, O and S, and optionally substituted with at least one alkyl, $CF_3$, OR, SR, NRR', COR, COOR, CONRR' or NRCOR' radical, with R and R' representing H or alkyl. For example, $R_2$ is a piperidine ring optionally substituted with at least one $C_1$-$C_{10}$ alkyl radical, and in particular methyl.

According to another embodiment, $R_1$ is H and $R_2$ is a saturated $C_1$-$C_{20}$ alkyl, optionally substituted with at least one substituent $A_1$. In particular, $A_1$ is a saturated or unsaturated ring having 5 to 6 atoms, optionally containing from 1 to 4 hetero atoms selected from N, O and S, that may contain at least one carbonyl function and may be optionally substituted with at least one group selected from among alkyl, F, $CF_3$, OR, SR, NRR', COR, COOR, CONRR' or NRCOR', with R and R' representing H or alkyl; a crown ether ring comprising 15 atoms and 5 —$CH_2CH_2O$— units; a group selected from among $CF_3$, OR, SR, NRR', COR, COOR, CONRR', NRCOR' or SiRR'R" with R, R' and R" representing H or alkyl.

According to another embodiment of the invention, $R_3$ is a phenyl or a heterocycle having 5 to 6 atoms, substituted with one or two substituents $A_3$ or attached to a hydrocarbon-based or heterocyclic ring having 5 to 6 atoms. In particular, $R_3$ is a heterocycle containing at least one nitrogen atom as hetero atom and optionally a sulfur atom, this heterocycle being optionally attached to a phenyl or thiazole ring, itself optionally attached to a hydrocarbon-based ring, in particular phenyl, or substituted with a COR or CN group or two groups, respectively COR and CN. In particular, $R_3$ is a phenyl, 2-benzothiazolyl, 2-pyridyl, 6-acetylnicotinonitrile, triazolyl or 4a,8a-dihydrobenzo[4,5]thiazolo[2,3-c][1,2,4]triazolyl group.

According to a particular embodiment of the invention, the 2-thioacetamide compound has one of the formulae (II) and (III) below:

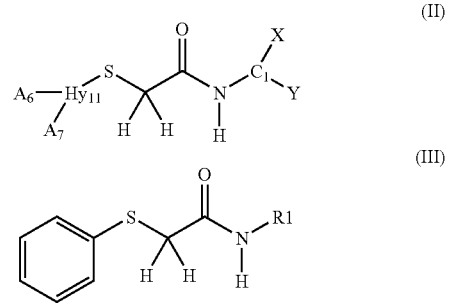

in which X and Y independently represent a hydrogen atom or a halogen; $C_1$ is a saturated or unsaturated hydrocarbon-based ring having 3 to 6 carbon atoms; $Hy_{11}$ is a heterocycle having 5 to 6 atoms, containing at least one hetero atom selected from N and S, and a combination thereof; $A_6$ and $A_7$ independently represent a substituent selected from among hydrogen, alkyl, COR, OR, SR, CN, COOR and the saturated or unsaturated rings $C_8$ having 5 or 6 atoms, optionally containing from 1 to 4 hetero atoms selected from among S and N, and combinations thereof, and/or being optionally attached to a hydrocarbon-based ring $C_9$ having 5 to 6 carbon atoms; $R_1$ is a saturated or unsaturated, linear or branched $C_1$-$C_{20}$ alkyl radical optionally substituted with at least one substituent $A_1$, a hydrocarbon-based ring or a heterocycle $Hy_2$ optionally substituted with at least one substituent $A_3$, $C_8$, $C_9$, $A_1$, $Hy_2$ and $A_3$ having the meaning given above.

According to the invention, the expression "salts of a compound of formula (I)" means the organic or inorganic salts of a compound of formula (I).

As inorganic salts that can be used according to the invention, mention may be made of: sodium salts or potassium salts, and also zinc ($Zn^{2+}$) salts, calcium ($Ca^{2+}$) salts, copper ($Cu^{2+}$) salts, iron ($Fe^{2+}$) salts, strontium ($Sr^{2+}$) salts, magnesium ($Mg^{2+}$) salts and manganese ($Mn^{2+}$) salts; hydroxides and carbonates.

The organic salts that can be used according to the invention are, for example, triethanolamine salts, monoethanolamine salts, diethanolamine salts, hexadecylamine salts, N,N,N',N'-tetrakis(2-hydroxy-propyl)ethylenediamine salts and trishydroxymethylaminomethane salts.

As examples of 2-thioacetamide compounds of formula (I) according to the invention, mention may be made of the following compounds:

Compound 1:

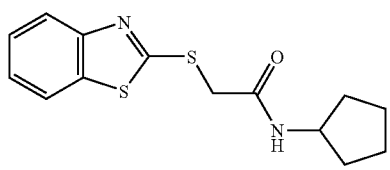

Compound 2:

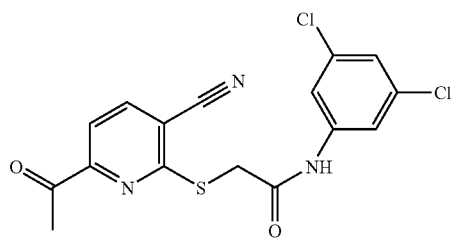

Compound 3:

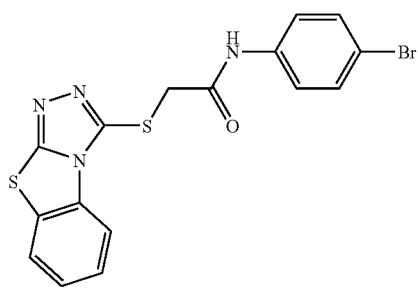

-continued

Compound 4:

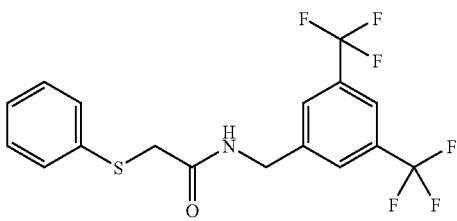

Compound 5:

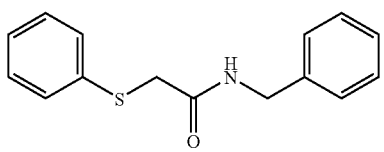

Compound 6:

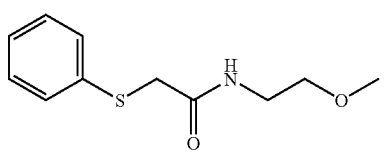

Compound 7:

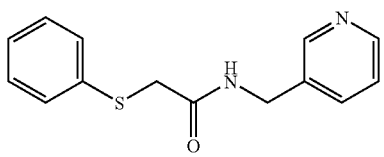

Compound 8:

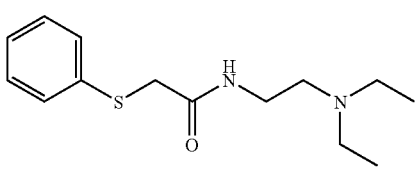

Compound 9:

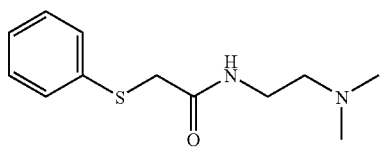

Compound 10:

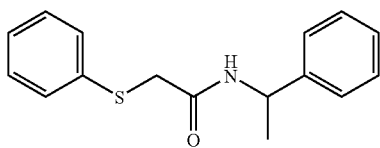

Compound 11:

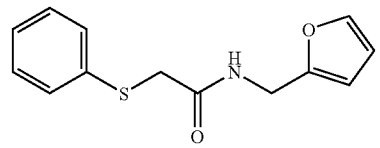

-continued
Compound 12:
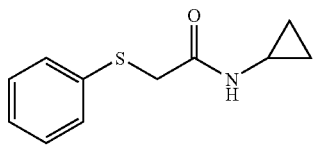
Compound 13:
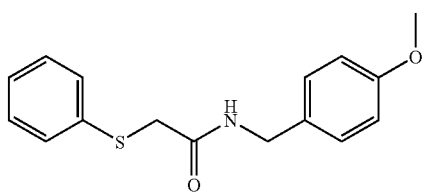
Compound 14:
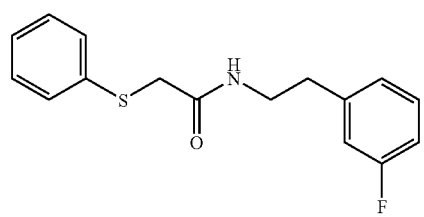
Compound 15:
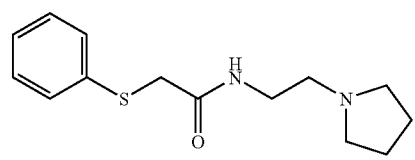
Compound 16:
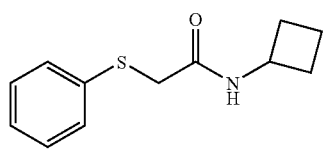
Compound 17:
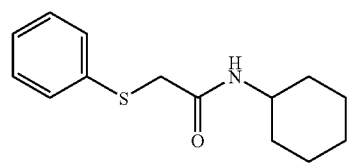
Compound 18:
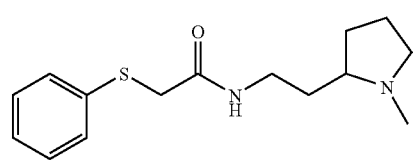
Compound 19:
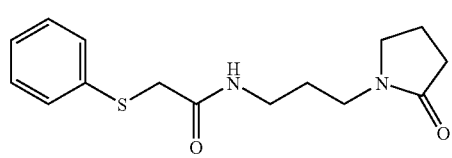
-continued
Compound 20:
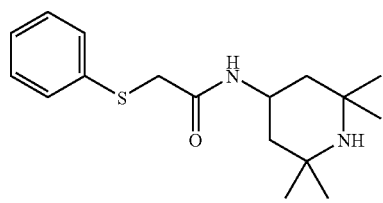
Compound 21:
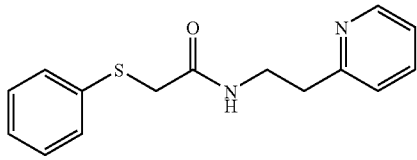
Compound 22:
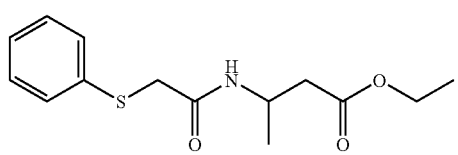
Compound 23:
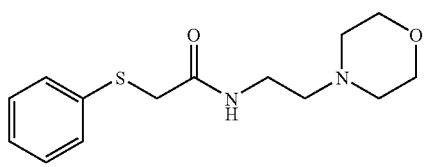
Compound 24:
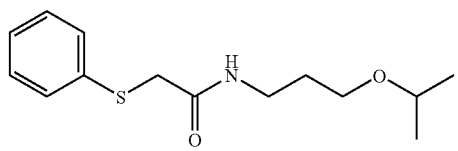
Compound 25:
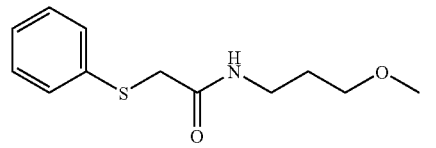
Compound 26:
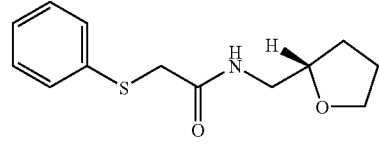
Compound 27:
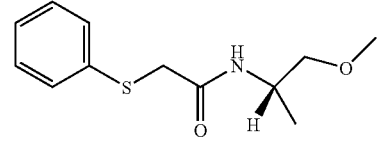

-continued
Compound 28:
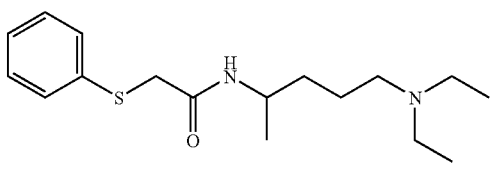
Compound 29:
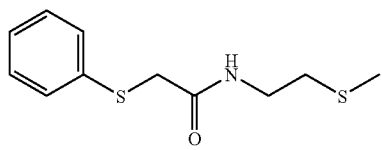
Compound 30:
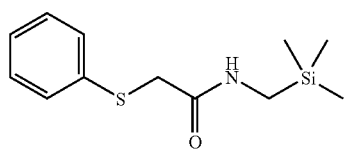
Compound 31:
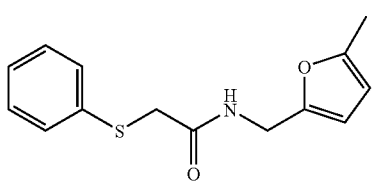
Compound 32:
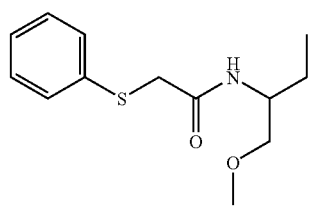
Compound 33:
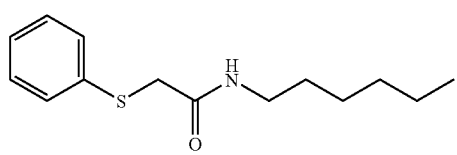
Compound 34:
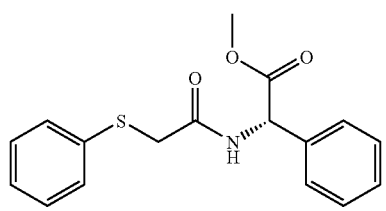
-continued
Compound 35:
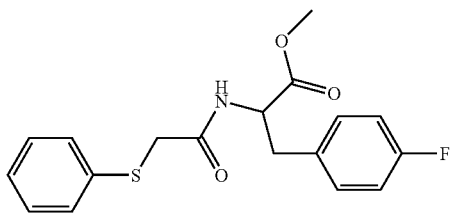
Compound 36:
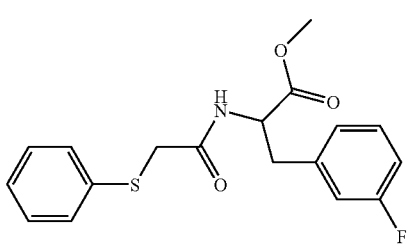
Compound 37:
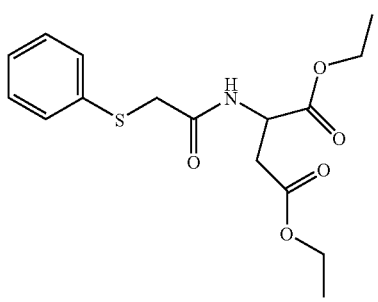
Compound 38:
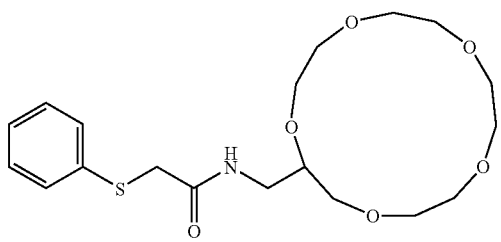
Compound 39:
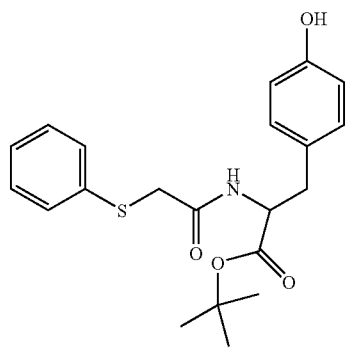

-continued

Compound 40:

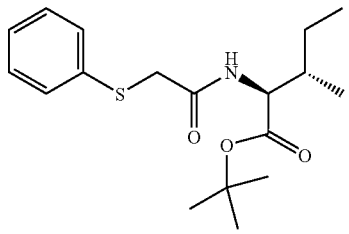

Compound 41:

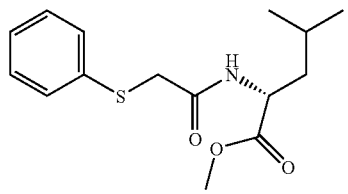

Compound 42:

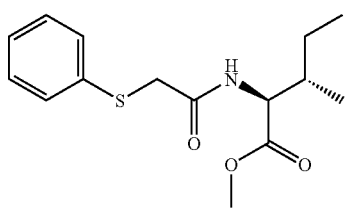

Compound 43:

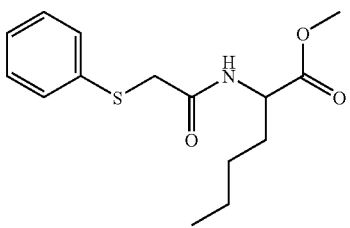

The compounds of formula (I), which may be salified or nonsalified, can be produced conventionally by successive condensation of two nucleophilic molecules with chloroacetyl acid chloride. For example, the amide function is produced by condensation of an amine with chloroacetyl chloride in a basic medium. The product obtained is itself condensed with a thiolate.

To provide an order of magnitude according to the invention, the compound of formula (I) or one of its salts or a mixture of compounds of formula (I) and/or of their salts can be used in an amount representing from $10^{-3}$% to 5% of the total weight of the composition, and preferably in an amount representing from $10^{-2}$% to 2% of the total weight of the composition, for example from 0.5% to 2%.

The compound of formula (I), which may be salified or nonsalified, can be formulated into a composition which should be ingested, injected or applied to the skin or to keratin fibers (to any area of the skin or fibers to be treated).

According to the invention, the compound of formula (I) or a mixture of compounds of formula (I) can be administered orally in an amount of from 0.1 to 300 mg per day, 5 to 10 mg/d.

Azo Compounds:

According to yet another embodiment, the 15-PGDH inhibitors according to the invention comprise at least one azo compound of formula (I) or one of its salts:

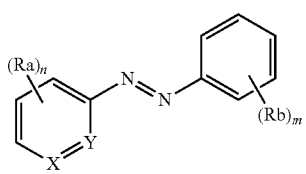

(I)

in which:
1) Ra and Rb which may be identical or different, are selected from among:
   a) a hydrogen atom, a halogen atom, a group $CF_3$, CN, OR, SR, NRR', NRC(=NR')NR''R''', COR, CSR, COOR, CONRR', $CH_2COOR$, CSNRR', NRCSR', NRCSNR'R'', NRCOR', NRCONR'R'', $SO_2NRR'$, $NRSO_2R'$, $NRSO_2NR'R''$, $SO_2R$, $NO_2$,
   b) a saturated or unsaturated, linear or branched $C_1$-$C_{10}$ alkyl radical optionally substituted with at least one substituent $A_1$ or with saturated or unsaturated rings $C^1$ containing from 3 to 7 atoms and/or optionally including at least one hetero atom and/or being optionally substituted with at least one substituent $A_2$ and/or optionally attached to at least one ring $C^3$ optionally including at least one hetero atom (to cover the fused rings) or
   c) an aromatic ring $C^2$ optionally including at least one hetero atom and/or being optionally substituted with at least one substituent $A_2$ and/or optionally attached to a ring $C^3$ optionally including at least one hetero atom (to cover the fused rings);
2) X and Y, which may be identical or different, represent —CRc or a nitrogen atom that is optionally in NO form or quaternized, Rc having the meaning of Ra or Rb, with the proviso that X and Y do not simultaneously represent a nitrogen atom that is in NO form or quaternized;
3) n and m represent integers ranging from 0 to 5;
   where R, R', R'' and R''', which may identical or different, denote:
   a hydrogen atom or a saturated or unsaturated, linear or branched $C_1$-$C_{10}$ alkyl radical,
   an aromatic ring $C^2$ optionally including at least one hetero atom, optionally substituted with at least one substituent $A^2$;
   where $A_1$ is selected from among a halogen atom, a group $CF_3$, CN, OR, SR, NRR', NRC(=NR')NR''R', COR, CSR, COOR, CONRR', CSNRR', NRCSR', NRCSNR'R'', NRCOR', NRCONR'R'', $SO_2NRR'$, $NRSO_2R'$, $NRSO_2NR'R''$, $SO_2R$, $NO_2$;
   where $A_2$ is selected from among linear or branched $C_1$-$C_{10}$ alkyl radicals, $OR_1$, $SR_1$, $NR_1R'_1$, $COOR_1$, $COR_1$ and $CH_2COOR_1$, with $R_1$ and $R'_1$, which may identical or different, denoting hydrogen, or a saturated or unsaturated, linear or branched $C_1$-$C_{10}$ alkyl radical;
   where the hetero atom is selected from N, O, S and Se.

In the subsequent text, and unless expressly mentioned, the use of the term "compound of formula (I)" should be understood to mean both the compound of formula (I) and one of its salts.

According to the invention, the term "at least one" means one or more (2, 3 or more). In particular, the composition may contain one or more compounds of formula (I). This or these compounds may be cis or trans isomers or a mixture of cis/trans isomers.

For the purpose of the invention, the term "alkyl radical" means a hydrocarbon-based radical that may be linear or branched and saturated or unsaturated. In particular, the alkyl radical contains from 1 to 10 carbon atoms, and in particular from 1 to 5 atoms. As examples of alkyl radicals that can be used in the invention, mention may be made of methyl, ethyl, isopropyl, tert-butyl or isopropyl radicals.

As halogen atoms, exemplary are chlorine, fluorine or bromine atoms, and better still chlorine or fluorine atoms.

According to the invention, the rings $C^1$, $C^2$ and $C^3$ of formula (I) contain from 3 to 7 atoms, and better still from 5 to 6 atoms, and may contain one or more hetero atoms such as S, N, O or Se, or combinations thereof, and thus form heterocycles Hy. The hydrogen atoms of these rings may also be partly substituted with a substituent $A_2$. In addition, the rings $C_1$ and $C_3$ may be saturated or unsaturated.

As saturated hydrocarbon-based rings that can be used in the invention, mention may be made of the cyclopropyl, cyclobutyl, cyclopentyl, cyclohexyl or cycloheptyl radical. As unsaturated hydrocarbon-based rings, mention may be made of the cyclohexenyl or phenyl radical.

According to the invention, $C^1$ and/or $C^2$ and/or $C^3$ may represent a heterocycle Hy containing from 3 to 7 atoms, and better still from 5 to 6 atoms, and including from 1 to 4 hetero atoms selected from N, O, S and Se, and combinations thereof, and better still selected from N and O, and combinations thereof. By way of examples of saturated heterocycles that can be used in the invention, mention may be made of the following heterocycles: azetidine, pyrrolidine, tetrahydrofuran, tetrahydrothiophene, imidazolidine, thiazolidine, pyrazolidine, oxazolidine, isoxazolidine, isothiazole, dihydroisothiazole, isothiazolidine, triazolidine, oxadiazolidine, thiadiazolidine, tetrahydropyridine, piperidine, tetrahydropyran, tetrahydropyrimidine, piperazine, hexahydrotriazines and morpholine.

By way of examples of unsaturated (or aromatic) heterocycles, the following heterocycles may be used: pyrrole, dihydropyrrole, furan, dihydrofuran, thiophene, dihydrothiophene, imidazole, dihydroimidazole, dihydrothiazole, dihydropyrazole, oxazole, dihydrooxazole, isoxazole, dihydroisoxazole, triazole, dihydrotriazole, oxadiazole, dihydrooxadiazole, thiadiazole, dihydrothiadiazole, tetrazole, pyridine, dihydropyridine, pyran, dihydropyran, pyrimidine, dihydropyrimidine, pyridazine, pyrazine, diazepine and triazine.

In addition, the rings $C^2$ and the rings $C^3$ may form fused heterocycles or rings, that may be saturated or unsaturated, and for example naphthalene, tetrahydronaphthalene, quinolene, isoquinolene, indole, benzimidazole, benzothiophene, benzofuran, purine or else pteridine or carbazole rings.

According to the invention, the compounds of formula (I) are in isolated form, i.e., nonpolymeric form. In addition, the substituents $R_a$ and $R_b$ may be located in any position of the phenyl ring bearing them.

According to the invention, the $R_a$ and $R_b$ borne by the same ring may be identical or different. Similarly, the substituents $A_1$ and $A_2$ borne, respectively, by the same alkyl radical or the same ring may be identical or different.

Preferably, n is an integer representing 0, 1, 2, 3 or 5. Moreover, m is an integer having in particular the value 0, 1 or 2.

Advantageously, at least one of $R_a$ and $R_b$ is a group COOR, OR, $NO_2$, $CF_3$, $SO_2NRR'$ or $CH_2COOR$, or a saturated or unsaturated $C_1$-$C_5$ alkyl radical, such as methyl, ethyl or allyl, optionally substituted with a morpholine heterocycle or a COOH group, with R and R' having the meaning indicated above. In particular, R and/or R' represent a hydrogen atom, a methyl radical or a pyridine group.

In addition, X and Y independently represent a nitrogen atom, or better still a CRc group, with Rc representing in particular a hydrogen atom, $NO_2$, OH, a COOR group, or a saturated or unsaturated $C_1$-$C_5$ alkyl radical, such as methyl or allyl, where R is H, methyl or ethyl.

According to the invention, the expression "salts of a compound of formula (I)" means the organic or inorganic salts of a compound of formula (I).

As inorganic salts that can be used according to the invention, mention may be made of sodium salts or potassium salts, and also zinc ($Zn^{2+}$) salts, calcium ($Ca^{2+}$) salts, copper ($Cu^{2+}$) salts, iron ($Fe^{2+}$) salts, strontium ($Sr^{2+}$) salts, magnesium ($Mg^{2+}$) salts, manganese ($Mn^{2+}$) salts, ammonium salts; hydroxides, carbonates, halides (such as chlorides), sulfates, nitrates and phosphates. Preferably, the salt is a sodium salt.

The organic salts that can be used according to the invention are, for example, triethanolamine salts, monoethanolamine salts, diethanolamine salts, hexadecylamine salts and N,N,N',N'-tetrakis(2-hydroxy-propyl)ethylenediamine salts.

As examples of azo compounds of formula (I) according to the invention, mention may be made of the following compounds:

Compound 1:

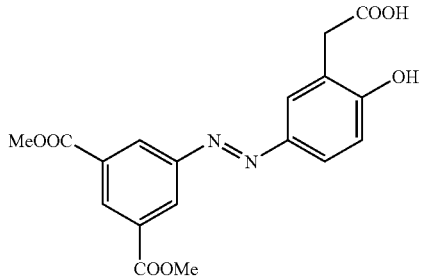

Compound 2:

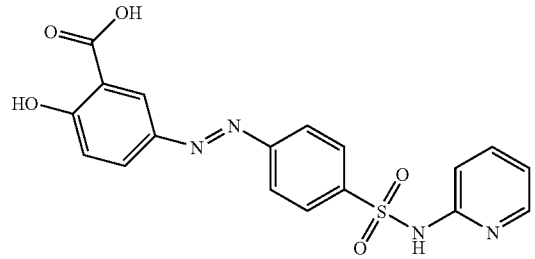

Compound 3:

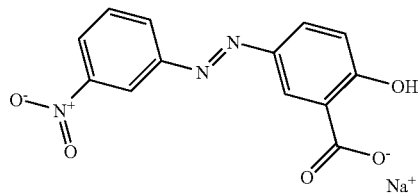

-continued

Compound 4:

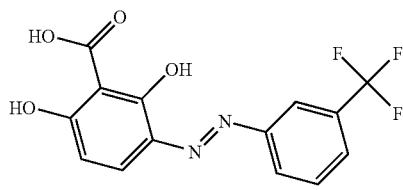

Compound 5:

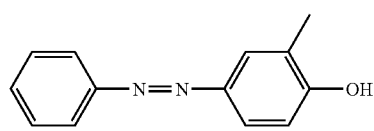

Compound 6:

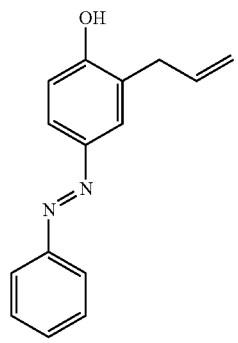

Compound 7:

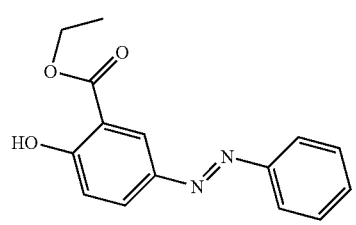

Compound 8:

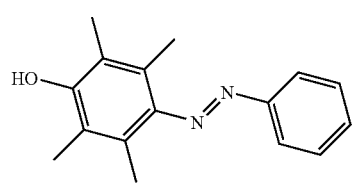

Compound 9:

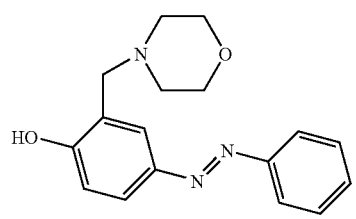

-continued

Compound 10:

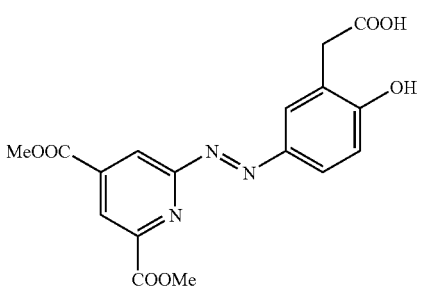

Compound 11:

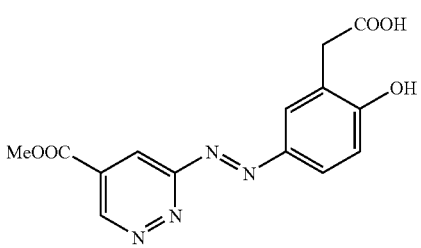

Compound 12:

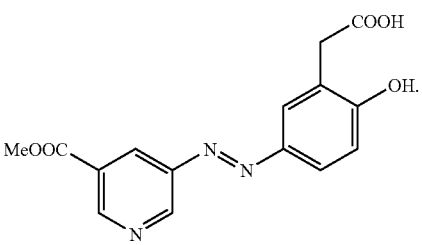

The compounds of formula (I), which may be salified or nonsalified, are known per se. They may be produced in a known manner, and in particular as described in the document Vogel's *Textbook of Practical Organic Chemistry*, 5th edition, 1989.

In particular, compound 1 of formula:

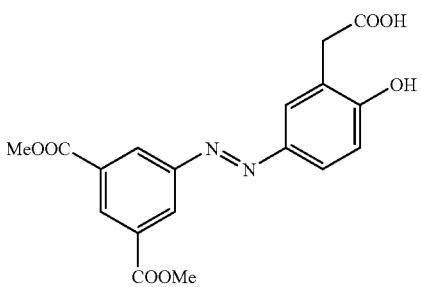

will also be referred to by the abbreviation PhCL28A, in the subsequent text.

According to a preferred embodiment, the compositions according to the invention also comprise at least one agent that is beneficial to the hair, for instance silicones, plant, animal, mineral or synthetic oils, waxes, ceramides, pseudoceramides, cationic polymers, sunscreens or vitamins.

The silicones that can be used in accordance with the invention are in particular polyorganosiloxanes that are insoluble in the composition, and may be in the form of oils, waxes, resins or gums.

Polyorganosiloxanes are defined in greater detail in the work by Walter Noll, *Chemistry and Technology of Silicones*, (1968) Academie Press. They may be volatile or nonvolatile.

According to one of its embodiments, the present invention features the nontherapeutic use of a cosmetic composition containing at least one 15-hydroxyprostaglandin dehydrogenase inhibitor, for treating canities. The use of such a composition according to the invention will in particular be intended for preventing or limiting the appearance of white body hairs or white hairs, or for reducing the number thereof.

One of the advantages of the use of 15-PGDH inhibitors according to at least one of the embodiments of the invention is that of re-establishing a pigmentation of the skin and/or of the hair corresponding to a physiological synthesis of pigmentation mediators, which results in a color close to the natural color. The main activity of the 15-PGDH inhibitors is not the direct coloring of the skin and/or skin appendages, in particular when they are compounds of the azo family, such as PhCL28A.

According to a preferred embodiment, the compositions according to the invention also contain at least one penetration-accelerating agent.

Such agents are known to those skilled in the art and in particular comprise urea or the compounds mentioned in application WO 01/74313. They will conventionally be present at concentrations of 0.01 to 20%, and in particular of 0.1 to 5%.

Advantageously, the compositions according to the invention also contain at least one agent for promoting pigmentation of the skin, of the hair and/or of body hair, that is different from a 15-hydroxyprostaglandin dehydrogenase inhibitor.

Such compounds are in particular tyrosinase substrates, such as tyrosine or L-DOPA, or compounds that activate the cAMP pathway, such as pro-opiomelanocortin derivatives, adenosine, or forskolin or its derivatives. Mention may also be made of extracts of plants such as cypress, Burnet, Sanguisorba officinalis or of chrysanthemum (Chrysanthemum morifolium), described in particular in EP 1 014 934.

The compositions comprising at least one 15-PGDH inhibitor according to the invention may also contain catalytic systems comprising 2 components, namely, a first component selected from among Mn(II) salts and oxides and/or Zn(II) salts and oxides, and mixtures thereof, and a second component selected from among alkali metal hydrogen carbonates, alkaline earth metal hydrogen carbonates, and mixtures thereof. Such compositions that promote pigmentation are in particular described in FR-2,814,947, FR-2,814,943, FR-2,814,946 or FR-2,817,469.

According to a preferred embodiment, the 15-PGDH inhibitor will be used in combination with an active compound for promoting pigmentation of the hair, that is disadvantageously liable to be metabolized by this enzyme. This is because it is now known that certain compounds conventionally proposed for this purpose have less activity due to the presence of 15-PGDH, which, by virtue of its action, decreases the concentration and therefore the effectiveness of the substances at the site of action.

In accordance with the present invention, it is now possible to obtain compositions having a reinforced effectiveness, by combining an active compound for promoting pigmentation of the hair, liable to be metabolized by 15-PGDH, and a 15-PGDH inhibitor as defined above. A synergistic action of the active agents for promoting pigmentation of the hair will thus be obtained in these compositions.

The composition will, for example, also contain at least one compound selected from among prostaglandins, in particular prostaglandin PGE1 and PGE2, their salts, their esters, their analogs and their derivatives, especially those described in WO 98/33497, WO 95/11003, JP 97-100091 and JP 96 134242, in particular prostaglandin receptor agonists. It may in particular contain at least one compound such as prostaglandin F2-alpha receptor (FP-R) agonists (in the form of an acid or in the form of a precursor, in particular in the form of an ester), just like latanoprost, fluprostenol, cloprostenol, travoprost or bimatoprost, prostaglandin E2 receptor (EP1-R, EP2-R, EP3-R, EP4-R) agonists (and precursors thereof, in particular the esters), such as 17-phenyl PGE2, viprostol, butaprost, misoprostol, sulprostone, 16,16-dimethyl PGE2, 11-deoxy-PGE1 or 1-deoxy-PGE1, prostacyclin (IP) receptor agonists and precursors thereof, in particular the esters, such as cicaprost, iloprost, isocarbacycline or beraprost, prostaglandin D2 receptor agonists and precursors thereof, in particular the esters, such as BW245C ((4S)-(3-[(3R,S)-3-cyclohexyl-3-isopropyl]-2,5-dioxo)$_4$-imidazolidineheptanoic acid) or BW246C ((4R)-(3-[(3R,S)-3-cyclohexyl-3-isopropyl]-2,5-dioxo)$_4$-imidazolidineheptanoic acid), or thromboxane A2 (TP) receptor agonists and precursors thereof, in particular the esters, such as I-BOP ([1S-[1a,2a(Z),3b(1E,3S),4a]]-7-[3-β-hydroxy-4-[4-(iodophenoxy)-1-butenyl]-7-oxabicyclo[2.2.1]hept-2-yl]-5-heptenoic acid.

Advantageously, the compositions according to the invention will comprise at least one 15-PGDH inhibitor as defined above and at least one prostaglandin or a prostaglandin derivative, for instance series 2 prostaglandins, including in particular, PGF2α and PGE2, in salt form or in the form of precursors, in particular of esters (for example, isopropyl esters), their derivatives such as 16,16-dimethyl PGE2,17-phenyl PGE2, 16,16-dimethyl PGF2α, 17-phenyl PGF2α, series 1 prostaglandins such as 11-deoxy-prostaglandin E1 or 1-deoxy-prostaglandin E1, in salt form or in the form of precursors, in particular of esters, or a nonprostanoic agonist of EP2 and/or EP4 receptors, in particular as described in EP 1 175 892.

Preferably, the 15-hydroxyprostaglandin dehydrogenase inhibitor inhibits very little, or not at all, the enzymes involved in prostaglandin synthesis in the hair, or prostaglandin synthases (in particular the synthesis of PGHS-1 or COX-1, of prostaglandin endoperoxide H synthase, or PGF synthase).

Other active agents that are beneficial to the health and the vigor of the hair or body hair may be present in the composition.

Mention may in particular be made of other active compounds for promoting hair regrowth and/or limiting hair loss.

These compounds may in particular be selected from among lipoxygenase inhibitors as described in EP-648,488, bradykinin inhibitors described in particular in EP-845,700, prostaglandins and derivatives thereof as described in the above, and nonprostanoic prostaglandin analogs as described in EP-1,175,891 and EP-1,175,890, WO 01/74307, WO 01/74313, WO 01/74314, WO 01/74315 or WO 01/72268.

Agents for promoting hair growth that may be present in the compositions according to the invention include vasodilators, anti-androgens, cyclosporines and analogs thereof, antimicrobial agents, retinoids and triterpenes, alone or as a mixture.

The vasodilators such as potassium channel agonists include minoxidil and the compounds mentioned in U.S. Pat. Nos. 3,382,247, 5,756,092, 5,772,990, 5,760,043, 5,466,694, 5,438,058 and 4,973,474; cromakalin, nicorandil and diaxozide can thus be present in the compositions.

The anti-androgens that can be used include in particular 5α-reductase inhibitors, such as finasteride and the compounds described in U.S. Pat. No. 5,516,779, cyprosterone acetate, azelaic acid, its salts and its derivatives and the compounds described in U.S. Pat. No. 5,480,913, flutamide and the compounds described in U.S. Pat. Nos. 5,411,981, 5,565,467 and 4,910,226.

The antimicrobial compounds can be selected from among selenium derivatives, ketoconazole, triclocarban, triclosan, pyrithione zinc, itraconazole, asiatic acid, hinokitiol, mipirocine, and the compounds described in EP-680,745, clinycine hydrochloride, benzoyl peroxide or benzyl peroxide, and minocycline.

The retinoids may be selected from among isotretinoin, acitretin and tazarotene. Other active compounds for promoting hair growth and/or limiting hair loss that are present in the compositions may also be selected from the group comprising aminexil and its derivatives, 6-O-[(9Z,12Z)-octadeca-9,12-dienoyl]hexapyranose, benzaconium chloride, benzethonium chloride, phenol, estradiol, chlorpheniramine maleate, chlorophyllin derivatives, cholesterol, cysteine, methionine, benzyl nictotinate, menthol, peppermint oil, calcium panthotenate, panthenol, resorcinol, protein kinase C activators, glycosidase inhibitors, glycosaminoglycanase inhibitors, pyroglutamic acid esters, hexosaccharide or acylhexosaccharide acids, substituted aryl ethylenes, N-acylated amino acids, flavonoids that have no action on COXs at the dosage used, ascomycin derivatives and analogs, histamine antagonists, triterpenes such as ursolic acid and the compounds described in U.S. Pat. Nos. 5,529,769, 5,468,888 and 5,631,282, saponins, proteoglycanase inhibitors, estrogen agonists and antagonists, pseudotrienes, cytokines and growth factor promoters, IL-1 inhibitors or IL-6 inhibitors, IL-10 promoters, TNF inhibitors, vitamins, such as vitamin D, vitamin B12 analogs and panthotenol, hydroxy acids, benzophenones and hydantoin.

The present invention also features a cosmetic regime or regimen for promoting pigmentation of the skin, the nails, body hair and/or the hair, wherein at least one 15-hydroxyprostaglandin dehydrogenase inhibitor, or a composition as defined above, is applied to the skin and/or the scalp and/or the skin appendages. The composition or the 15-PGDH inhibitor will be applied to the site of action and will be left in contact for a more or less long period of time, it being possible for the application to be repeated at regular or irregular intervals for several hours, days, weeks or months.

The 15-PGDH inhibitor may be applied simultaneously with the other active agents proposed in combination, or sequentially over time.

In order to further illustrate the present invention and the advantages thereof, the following specific examples are given, it being understood that same are intended only as illustrative and in nowise limitative. In said examples to follow, all parts and percentages are given by weight, unless otherwise indicated.

BRIEF DESCRIPTION OF THE FIGURES OF DRAWING

FIG. 1: expression of 15-hydroxyprostaglandin dehydrogenase by hair melanocytes in culture.

Figure 2:
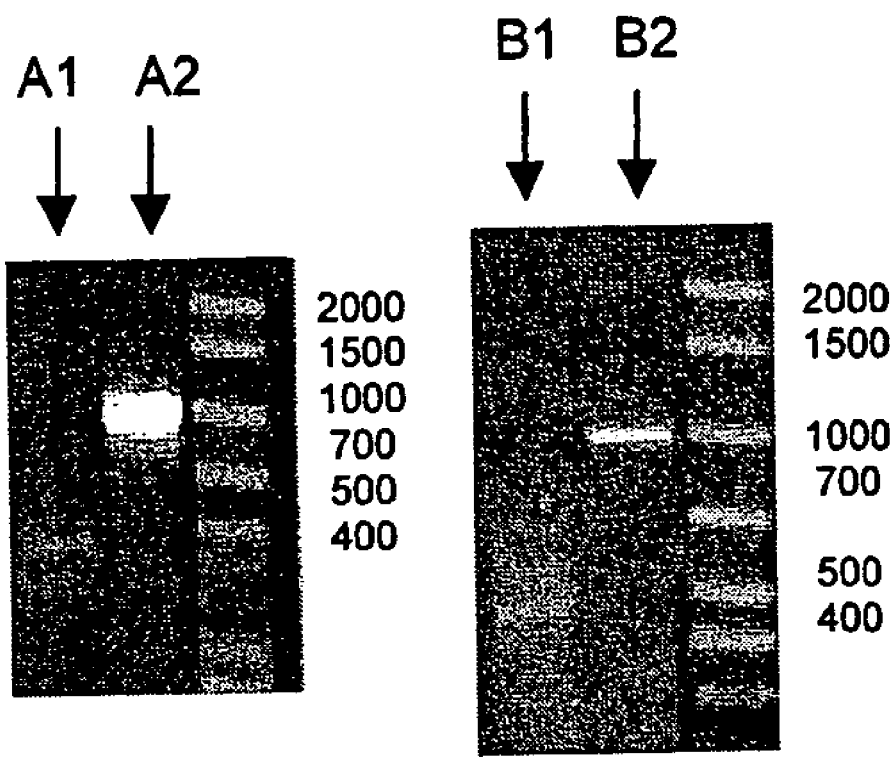

FIG. 2: expression of prostaglandin H synthase 1 by hair melanocytes in culture.

EXAMPLES

Example 1a

Demonstration of the Expression of mRNA Encoding PGHS-1 (Control, mRNA Encoding Glyceraldehyde 3-Phosphate Dehydrogenase) and encoding 15-PGDH (control, actin mRNA) in pigmented Hair melanocytes.

a—Isolation of Pigmented Hair Melanocytes:

The human scalp biopsy is cut up into small pieces, placed in a solution of dispase (2.4 U/ml, Boehringer Mannheim, Gmbh, Germany) and incubated for eighteen hours at +04° C. The fragments are then washed in PBS. The epithelial compartment is separated from the dermis using forceps under a binocular magnifying lens. The epithelial structures are then microdissected so as to separate the hair follicles and the epidermis, and then sorted. The isolated hairs are grouped together and treated with trypsin for five minutes at 37° C., and the trypsin is then neutralized (trypsin neutralizing system (TNS), C41110, Promocell, Heidelberg, Germany). The cell suspension obtained is seeded in the medium for primary culture of melanocytes (M2, Promocell, Heidelberg, Germany). After culturing for six days, the medium is renewed every two or three days. After ten to twenty days, the culture consists of keratinocytes and melanocytes. The melanocytes are selected by differential trypsination by incubating the culture with 0.05%-0.02% (w/v) trypsin-EDTA for three minutes at 37° C., and the trypsin is then neutralized by the TNS. It may be that the primary culture contains a few contaminating fibroblasts; the latter are eliminated by repeated treatment with 25 µg/ml of geneticin.

b—Extraction and Purification of Messenger RNAs:

The messenger RNAs are extracted from two different cultures of hair follicle melanocytes, that come from two samples taken from different individuals. The messenger RNA extraction (carried out on passages P3 or P4, 35 mm dish at confluence) is carried out according to the protocol and with the reagents of the QuickPrepr mRNA kit (Pharmacia Biotech, Brussels, Belgium).

For each sample (a cell culture at confluence in a 35 mm diameter dish) studied, the following protocol will be applied.

The cell culture supernatant is removed and replaced with 800 µl of lysis buffer, and the lysate obtained is recovered and introduced into a 1.5 ml polypropylene microtube (tube 1).

1 ml of suspension of oligo(dT-18) cellulose microspheres is introduced into a 1.5 ml microtube (tube 2) and centrifuged at 14000 rpm for 1 minute. The supernatant is removed. The contents of tube 1 is then introduced into tube 2, and the microspheres are resuspended in the lysate by gentle agitation of the tube for 3 minutes.

The polyA+ RNAs attached to the microspheres are isolated from the contaminants by means of washing. The tube is centrifuged at 14000 rpm for 1 minute, and the supernatant is removed and replaced with 1 ml of washing buffer (high salt buffer). The microspheres are resuspended as above and the tube is gently agitated for 1 minute. The tube is centrifuged at 14000 rpm for 1 minute, and the supernatant is again removed and replaced with 1 ml of low salt buffer.

A total of five washes with the low salt buffer followed by three washes with the high salt buffer will thus be carried out.

The content of the third wash (microspheres+buffer) is loaded onto a microcolumn containing a filter at the base (microspin™ column), placed in a 1.5 ml microtube. The entire assembly is centrifuged at 14000 rpm for 1 minute. The microcolumn is recovered and placed in a 1.5 ml microtube. The polyA+ messenger RNAs are then eluted with a total final volume of 0.4 ml of elution buffer, brought to 65° C. beforehand.

c—Synthesis of the Complementary DNA (cDNA) Strands:

This step is carried out using the first strand cDNA synthesis kit (Pharmacia Biotech, Brussels, Belgium).

The complementary DNA samples obtained are diluted to ¹⁄₁₀th in sterile water, before PCR.

d—Choice of Primers, PCR (Polymerase Chain Reaction):

Primers specific for the sequences of interest will be used after synthesis, with the client's own material, by Genset S A, rue Robert et Sonia Delaunay, Paris.

The first pair of primers hybridizes to the sequence encoding a ubiquitous protein (glyceraldehyde 3-phosphodehydrogenase). The other two pairs of primers hybridize to the sequence encoding prostaglandin H synthase 1 and 15-hydroxyprostaglandin dehydrogenase, respectively.

Human β-actin; genbank accession no.: NM 001101 SENSE PRIMER: 5'-ATGGATGATGATATCGCCGCGCT-3' (SEQ ID NO: 1) Antisense primer: 5'-CGGACTCGTCATACTCCTGCTTG-3' (SEQ ID NO: 2) Amplified fragment: 1095 base pairs.

Prostaglandin H synthase 1 (PGHS-1); genbank accession no.: 36271 Sense primer: 5'-CTCATAGGGGAGACCAT-CAAG-3' (SEQ ID NO: 3) Antisense primer: 5'-CCT-TCTCTCCTACGAGCTCCT-3' (SEQ ID NO: 4) Amplified fragment: 451 base pairs.

Human 15-hydroxyprostaglandin (15-PGDH); genbank accession no.: NM 000860 Sense primer: 5'-TGCCAATG-GATTGATAACACTCAT-3' (SEQ ID NO: 5) Antisense primer: 5'-ACAGCAGTTTTCATCTGGGATATG-3' (SEQ ID NO: 6)

The PCR reactions are carried out according to the Takara Taq™ protocol, Takara Shuzo Co., Ltd. Biomedical Group, Seta 34-1, Otsu, Shiga, 520-2193, Japan. The hybridization temperatures (THs) are, respectively, 54° C. (15-PGDH) and 57° C. (actin, GAPDH and PGHS-1); the number of cycles=35.

1 µl of each of the complementary DNA samples is placed in the reaction.

5 µl (2.5 µl+2.5 µl) of the pairs of primers at 40 ng/µl are placed in the reaction.

| | |
|---|---|
| 4' at 95° C. | 1 cycle |
| 30" at 94° C. | |
| 1' at THs° C. | 35 cycles |
| 1' at 72° C. | |
| 7' at 72° C. | 1 cycle | d—Reading:

1.1 Preparation of an Agarose Gel:

0.65 g of agar (molecular biology certified agarose, Bio-Rad Laboratories, 2000 Alfred Nobel Dr., Hercules, Calif. 94547, USA) is weighed out.

50 ml of 1×TAE buffer, Amresco, Solon, Ohio 44139, USA, are added.

The agarose in suspension is brought to boiling and then introduced into a tank containing a drop of ethydium bromide (25 ag), Amresco, Solon, Ohio 44139, USA.

A "comb" for depositing the samples is placed at one end of the tank.

After cooling for 30 minutes (room temperature), 20 µl of the results of PCRs are introduced individually into a well of the gel, along with 10 µl of a molecular weight ladder standard (Amplisize™, molecular ruler, 170-8200), Bio-Rad.

The entire assembly is subjected, immersed in a large excess of 1×TAE buffer, to an electric field of 100 volts for 45 minutes.

Exposure of the gel to ultraviolet light makes it possible to observe, by fluorescence, the results obtained.

The results of the study of the expression of 15-PGDH are shown in FIG. 1.
A. Source of cDNA derived from hair melanocytes from donor 1.
B. Source of cDNA derived from hair melanocytes from donor 2.
M. Molecular marker ladder in base pairs (bp).
A1,B1: Expression of 15-PGDH (706 bp)
A2,B2: Expression of actin (reference gene), (1096 bp).

The gels showing the expression of PGHS-1 are represented in FIG. 2:
A. Source of cDNA derived from hair melanocytes from donor 1.
B. Source of cDNA derived from hair melanocytes from donor 2.
M. Molecular marker ladder in base pairs (bp).
A1,B1: Expression of PGHS-1 (451 bp)
A2,B2: Expression of actin (reference gene), (1096 bp).

Example 2a

Demonstration of the Expression of 15-PGDH mRNA in Dermal Papilla Fibroblasts of Hair in Culture 1. Dissection of Hair Follicles:

Hair follicles originating from facelifts in volunteer donors are dissected according to the methods described in the B. Bernard/O. Gaillard patent FR-2,736,721 A1 of Jan. 17, 1997; U.S. Pat. No. 5,712,169 A of Jan. 28, 1998.

The isolated follicles are immersed in a Petri dish containing 20 ml of Gibco 199 culture medium, reference 31153-018, Life Technologies, BP 96, Cergy Pontoise Cedex, supplemented with 1% (v/v) of a solution of antibiotics, Gibco reference 15240-096.

Using two needles, reference NN-2516R, Terumo Europe N. V. Leuven, Belgium, each mounted on a 1 ml syringe, reference BS-01N, Terumo, 15 dermal papillae are extracted from the follicle bulbs.

These 15 papillae are placed in a 35 mm diameter Petri dish containing 2 ml of 199 medium previously used, containing 20% of fetal calf serum, Gibco, reference 10091-130. The dish is then placed in a thermostatic incubator at 37° C. under 5% of $CO_2$.

A first passage is carried out after incubation for 3 weeks, without the medium having been replaced beforehand. The medium is removed, 1 ml of trypsin solution, Gibco, reference 25050-022 is placed in the Petri dish, and the dish is returned to the incubator for 4 minutes. The cells (papilla fibroblasts) thus resuspended in the trypsin solution (microscopic control) are placed in a 15 ml tube, reference Falcon, 352097, Becton Dickinson, Chemin des sources, BP 37, Meylan 38241, containing 10 ml of 199 medium previously used (containing 20% of fetal calf serum).

After centrifugation for 5 minutes at 1500 rpm, the supernatant is removed and the cell pellet is taken up with 5 ml of 199 medium previously used (here containing 10% of fetal calf serum).

The cell suspension is placed in a 35 mm diameter Petri dish and returned to the incubator (37° C., 5% of $CO_2$).

The following passages P2, P3, P4, are carried out according to the same principle. They are performed as soon as the cells reach confluency.

2. Extraction and Purification of Messenger RNAS:

The extraction of the messenger RNAs of the dermal papilla fibroblasts (carried out on passages P3 or P4, 35 mm dish at confluence) is carried out according to the protocol and with the reagents of the QuickPrepr mRNA kit (Pharmacia Biotech, Brussels, Belgium).

For each sample (a cell culture at confluence in a 35 mm diameter dish) studied, the following protocol will be applied.

The cell culture supernatant is removed and replaced with 800 μl of lysis buffer, and the lysate obtained is recovered and introduced into a 1.5 ml polypropylene microtube (tube 1).

1 ml of suspension of oligo(dT-18) cellulose microspheres is introduced into a 1.5 ml microtube (tube 2) and centrifuged at 14000 rpm for 1 minute. The supernatant is removed. The contents of tube 1 is then introduced into tube 2, and the microspheres are resuspended in the lysate by gentle agitation of the tube for 3 minutes.

The polyA+ RNAs attached to the microspheres are isolated from the contaminants by means of washing. The tube is centrifuged at 14000 rpm for 1 minute, and the supernatant is removed and replaced with 1 ml of washing buffer (high salt buffer). The microspheres are resuspended as above and the tube is gently agitated for 1 minute. The tube is centrifuged at 14000 rpm for 1 minute, and the supernatant is again removed and replaced with 1 ml of low salt buffer.

A total of five washes with the low salt buffer followed by three washes with the high salt buffer will thus be carried out.

The content of the third wash (microspheres+buffer) is loaded onto a microcolumn containing a filter at the base (microspin™ column), placed in a 1.5 ml microtube. The entire assembly is centrifuged at 14000 rpm for 1 minute. The microcolumn is recovered and placed in a 1.5 ml microtube. The polyA+ messenger RNAs are then eluted with a total final volume of 0.4 ml of elution buffer, brought to 65° C. beforehand.

3. Precipitation of Messenger RNAs:

10 μl of glycogen solution, 40 μl of 2.5M potassium acetate and 1 ml of absolute ethanol, at −20° C., are introduced into the tube containing the eluate. The tube is placed in dry ice (−80° C.). After 1 hour, the tube is centrifuged at 4° C. and at 17500 rpm for 15 minutes. The supernatant is removed with care (the mRNAs form a very small pellet) and replaced with 1 ml of 80% ethanol (ethanol/water; v/v) at −20° C. The tube is centrifuged at 17500 rpm and at 4° C. for 15 min, and the supernatant is completely removed. The pellet is taken up with 8 μl of sterile distilled water.

4. Synthesis of Complementary DNA (cDNA) Strands:

This step is carried out using the first strand cDNA synthesis kit (Pharmacia Biotech, Brussels, Belgium).

The tube containing the mRNAs is placed at 65° C. for 10 minutes and then in ice for 5 minutes and the following are then introduced:

5 μl of a buffered solution containing a suspension of reverse transcriptase.

1 μl of oligodT(18) primers at 0.8 μg/ml,

1 μl of aqueous solution of dithiothreitol at 200 nM.

The tube is incubated at 37° C. for 1 hour. The reaction is blocked by placing the tube in ice.

5. Choice of Primers, Polymerase Chain Reaction (PCR):

1 μl (of a dilution to 1/10th in sterile distilled water) of complementary DNAs thus obtained is subjected, in a buffered medium, to a polymerase chain reaction (PCR) in the presence of pairs of specific primers (at a titer of 40 ng/ml), Taq polymerase and nucleotides, according to the supplier's data.

The primers specific for the sequences of interest that will be used are obtained by synthesis, using the client's own material, by Genset SA, rue Robert et Sonia Delaunay, Paris.

The first pair of primers hybridizes to the sequence encoding a ubiquitous protein (β-actin). The second pair of primers hybridizes to the sequence encoding 15-hydroxyprostaglandin dehydrogenase.

Human β-actin; genbank accession no.: NM 001101 SENSE PRIMER 5'-ATGGATGATGATATCGCCGCGCT-3' (SEQ ID NO: 1) Antisense primer: 5'CGGACTCGTCAT-ACTCCTGCTTG-3' (SEQ ID NO: 2) Amplified fragment: 1096 base pairs.

Human 15-hydroxyprostaglanding (15-PGDH); genbank accession no.: NM 000860 Sense primer: 5'-TGCCAATG-GATTGATAACACTCAT-3' (SEQ ID NO: 5) Antisense primer: 5'-ACAGCAGTTTTCATCTGGGATATG-3' (SEQ ID NO: 6) Amplified fragment: 706 base pairs.

The PCR reaction is carried out according to an adaptation of the Takara Taq™ protocol, Takara Shuzo Co., Ltd. Biomedical Group, Seta 34-1, Otsu, Shiga, 520-2193, Japan. The hybridization temperature is 54° C. for the pairs of primers (β-actin; PGFS, 15-PGHD), the number of cycles=35.

*A buffered solution of nucleotides is prepared by mixing 171 μl of sterile distilled water, 24.5 μl of 10× buffer from the kit and 20 μl of mixture of nucleotides (dNTPs) from the kit.

The following are introduced into a microtube suitable for PCR:

1 μl (of a dilution to 1/10) of complementary DNA,

43 μl of the mixture of nucleotides in buffered solution*

5 μl (2.5 μl+2.5 μl) of the pairs of primers at 40 ng/μl are used in the reaction, 50 μl of mineral oil.

The tube is placed in a PCR machine and the following cycles are programmed.

| | |
|---|---|
| 4' at 95° C. | 1 cycle |
| 30" at 94° C. | |
| 1' at 54° C. | 35 cycles |
| 1' at 72° C. | |
| 7' at 72° C. | 1 cycle |

6. Reading:

a. Preparation of an Agarose Gel:

0.65 g of agar (molecular biology certified agarose, Bio-Rad Laboratories, 2000 Alfred Nobel Dr., Hercules, Calif. 94547, USA) is weighed out.

50 ml of 1×TAE buffer, Amresco, Solon, Ohio 44139, USA, are added.

The agarose in suspension is brought to boiling and then placed into a tank containing a drop of ethydium bromide (25 μg), Amresco, Solon, Ohio 44139, USA.

A "comb" for depositing the samples is placed at one end of the tank.

After cooling for 30 minutes (room temperature), 20 μl of the results of PCRs are introduced individually into a well of the gel, as are 10 μl of a mixture of molecular weight standard (Amplisize™, molecular ruler, 170-8200, Bio-Rad Laboratories, 2000 Alfred Nobel Dr., Hercules, Calif. 94547, USA).

The entire assembly is subjected, immersed in a large excess of 1×TAE buffer, to an electric field of 100 volts for 45 minutes.

Exposure of the gel to ultraviolet light makes it possible to observe, by fluorescence, the results obtained.

Expected amplimer weights.

Actin=1096 base pairs; 15-PGDH=706 base pairs; PGFS=1061 base pairs.

Samples 1, 2 and 3 originate from different cultures of dermal papilla fibroblasts from human hair.

Investigation of the expression of 15-hydroxyprostaglandin dehydrogenase It is noted that 15-PGDH is expressed in the various samples, with a band of characteristic MW at 706 bp.

Example 3a

Cloning from Dermal Papilla Fibroblasts

The poly-A+ messenger RNAs were extracted and purified from a culture of dermal papilla fibroblasts of hair, and the complementary DNA (cDNA) was then synthesized, as described in Example 1.

Pairs of primers (synthesized by Genset) to which sequences encoding restriction sites were added, were chosen for 15-PGDH (genbank accession no.=NM 000860).

a) Primers for 15-PGDH

5'-GGG GAT OCA TGC ACG TGA ACG GCA AAG TG-3' (SEQ ID NO: 7); sense primer BamH1 site (in bold)

5'-TCT OGA GAG CTG TTC ATT GGG T-3' (SEQ ID NO: 8); antisense primer Xho1 site (in bold).

b) Polymerase Chain Reaction (PCR)

The PCR protocol used for the cloning of 15-PGDH reiterates, in the main, that described above, except for the following:

The Taq polymerase used according to the supplier's data (Pfu Turbor DNA polymerase), Stratagene Cloning Systems, 11011 North Torrey Pines Road, La Jolla, Calif. 92037.

Hybridization temperature 59° C., elongation time 2 min, 25 cycles in total for 15-PGDH, expected amplimer=815 bp.

c) The PCR products are digested with the restriction enzymes (BamH1; Xho1 for 15-PGDH) according to the supplier's data (Amersham Pharmacia Biotech, 12 avenue des Tropiques, ZA Courtaboeuf, 91944 Les Ulis) and are then migrated individually on a 1.3% agarose gel (see Example 1; 6. Reading).

d) The bands corresponding to the expected amplimers (see ac) are cut out using a scalpel (after detection under ultraviolet light) and these cut-out bands are purified according to the recommendations of the supplier of the Wizard" PCR Preps DNA Purification System kit (Promega Corporation, 2800 Woods Hollow Road, Madison, Wis. 53711-5399).

e)

15-PGDH

The ligation into a vector pGEX 4T3 (Amersham Pharmacia Biotech, 12 avenue des Tropiques, ZA Courtaboeuf, 91944 Les Ulis) digested (BamH1/Xho1) and purified beforehand, according to the indications of the supplier of the Fast-Link™ DNA ligation kit, Epicentre, 1202 Ann Street, Wis. 53713, is carried out.

f) Transformations

Competent bacteria of the BL21DE3plys type will be used for the transformation with the construct (pGEX4T3/15-PGDH). This strain is sold by Stratagene. The transformations are carried out according to a conventionally used protocol, as described, for example, in the Fast-Link™ DNA ligation kit used above. The infected bacteria (clones) are selected (white colonies) after deposit and culture for 24 hours at 37° C. of a fraction of these transformation products on LB-agar medium cooled in a Petri dish (L-2897, D'Abeau Chesne, BP701,38297 Saint Quentin Fallavier) Sigma-Aldrich, L'isle D'Abeau Chesne, BP 701, 38297, Saint Quentin Fallavier) containing 100 μg/ml of ampicillin.

g) Production of 15-PGDH

A colony originating from the "15-PGDH transformation" Petri dish is taken and placed in 250 ml of LB medium (L-3022, Sigma-Aldrich, L'isle D'Abeau Chesne, BP 701, 38297, Saint Quentin Fallavier) containing 100 μg/ml of ampicillin, and the flask is incubated for 16 hours at 37° C. with shaking.

After 16 hours, each of the flasks is introduced into an Erlenmeyer flask containing 2.5 l of LB medium containing 100 μg/ml ampicillin. These two Erlenmeyer flasks are incubated with shaking at 37° C. for 3 to 4 hours (until the optical density measured at 630 nm is between 0.6 and 0.9).

Isopropyl β-D-thiogalactopyranoside (IPTG), (16758, Sigma-Aldrich, L'isle D'Abeau Chesne, BP 701, 38297, Saint Quentin Fallavier) is added such that the final concentration is 0.1 mM.

The Erlenmeyer flasks are incubated for a further 24 hours with shaking at ambient temperature (20-25° C.).

The cultures thus obtained are centrifuged (in 250 ml fractions) at 5000 rpm for 7 minutes, and the pellets are taken up with 3 ml of 10 mM phosphate buffer, pH=7.00 (4° C.), containing a mixture of protease inhibitors (protease inhibitor cocktail set I 539131, Calbiochem-Novabiochem Corporation, 10394 Pacific Center Court, San Diego, Calif. 92121). The bacterial suspensions (grouped together in 40 ml fractions in a polypropylene tube) are blocked in ice and subjected to ultrasound (Vibra cell 20 kHz, 72434, Bioblock Scientific, Parc d'innovation, BP111, 67403 Illikirch), the probe being immersed in each tube for 15 seconds (6 shocks of 15 seconds per tube). Each tube is centrifuged at 4° C. at 16000 rpm for 1 hour.

h) Purification of 15-PGDH

The supernatants are recovered and placed in a polypropylene tube containing 1 ml of Gluthatione-Sepharose" 4B (40 ml of supernatant per 1 ml of Gluthatione-Sepharose" 4B) washed beforehand according to the supplier's recommendations (Amersham Pharmacia Biotech, 12 avenue des Tropiques, ZA Courtaboeuf, 91944 Les Ulis).

The tubes are placed vertically on a rotatory shaker, rotation at 10 rpm for 1 hour at room temperature (20-25° C.).

The tubes are centrifuged at 1,000 rpm for 3 minutes, and the supernatant is removed. 40 ml of a 10 mM phosphate buffer, pH-7.00, are introduced into each of the tubes. After gentle agitation (inverting), the tubes are again centrifuged for 3 minutes at 1,000 rpm.

The operation is carried out 5 times. A sixth wash is carried out with 40 ml of phosphate buffered saline, pH-7.2 (PBS, Bio-Merieux S, 69280 Marcy-l'Etoile). After centrifugation, the supernatant is again remained.

i) Elution of 15-PGDH

A suspension of thrombin protease is reconstituted at 1 unit/µl in PBS according to the supplier's recommendations (Amersham Pharmacia Biotech, 12 avenue des Tropiques, ZA Courtaboeuf, 91944 Les Ulis).

950 µl of PBS and 50 µl of reconstituted thrombin suspension are introduced into each tube containing 1 ml of Gluthatione-Sepharose$^r$ 4B. The tubes are shaken in a slightly inclined position, for 16 hours at 250 rpm. After 16 hours, the tubes are centrifuged at 3000 rpm for 5 min, and the supernatants are collected.

The amount of protein is evaluated by following the Bio-Rad DC protein assay procedure (Bio-Rad Laboratories, 2000 Alfred Nobel Dr., Hercules, Calif. 94547).

Thus, for 15-PGDH, between 0.2 and 5 mg of protein per ml, most commonly 1 mg/ml, are obtained.

The protein suspensions thus obtained are diluted, respectively, in PBS supplemented with 10% glycerol, and PBS, such that the final protein concentrations are at a titer of 0.2 mg/ml for 15-PGDH. The suspension is blocked at −80° C. until use.

Electrophoretic analyses (SDS-Page) carried out under standard conditions demonstrate the quality of the results thus obtained.

Example 4a

Evaluation of the Effect of Molecules on these Enzymes and Characterization of a Certain Family of Molecules such as 15-PGDH Inhibitors a) 15-PGDH Test The enzyme obtained is at a concentration of 0.3 mg/ml and is blocked at −80° C. This suspension is thawed and stored in ice.

A 100 mM Tris buffer, pH-7.4, containing 0.1 mM of dithiothreitol (D5545, Sigma-Aldrich, L'isle D'Abeau Chesne, BP 701, 38297, Saint Quentin Fallavier), 1.5 mM of β-NAD (N6522, Sigma-Aldrich, L'isle D'Abeau Chesne, BP 701, 38297, Saint Quentin Fallavier) and 50 µM of prostaglandin $E_2$ (P4172, Sigma-Aldrich, L'isle D'Abeau Chesne, BP 701, 38297, Saint Quentin Fallavier) is prepared.

0.965 ml of this buffer (brought to 37° C. beforehand) is placed in the cuvette of a spectrophotomer (Perkin-Elmer, Lambda 2) thermostated at 37° C., the measuring wavelength of which is set at 340 nm. 0.035 ml of enzyme suspension at 37° C. is placed in the cuvette concomitantly with the recording (increase in optical density at 340 nm).

The maximum reaction rate is recorded.

The assay values (molecules) are compared with the control value (without molecule), and the results are expressed as % of the control value.

The results obtained for molecules A and B are as follows:

| At 50 µM | % inhibition 15-PGDH |
|---|---|
| Molecule A | 43 |
| Molecule B | 57 |

Example 1

Examples of Phenylfuran, Phenylthiophene and Phenylpyrrole Heterocyclic Compounds of Formula (I) According to the Invention:

Compound 1: 4-{5-[(2,4-dioxo-1,3-thiazolidin-5-ylidene)methyl]-2-furyl}benzoic acid

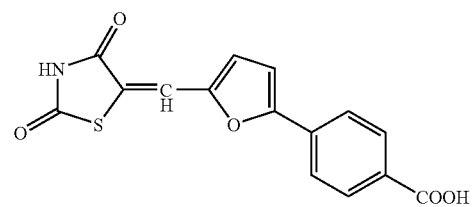

and more especially compound 1a:

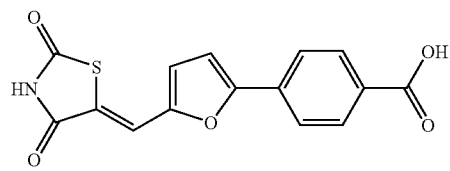

Compound 2: ethyl 4-{5-[(2,4-dioxo-1,3-thiazolidin-5-ylidene)methyl]-2-furyl}benzoate

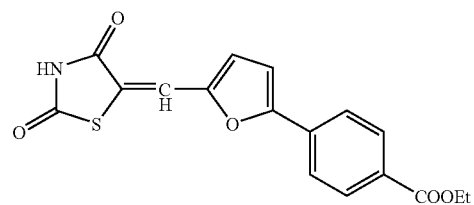

Compound 3: 5-({5-[3,5-bis(trifluoromethyl)phenyl]-2-furyl}methylene-1,3-thiazolidene-2,4-dione

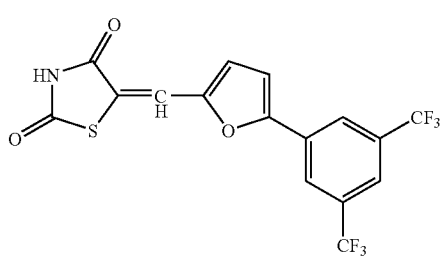

Compound 4: 3-{5-[(2,4-dioxo-1,3-thiazolidin-5-ylidene)methyl]-2-furyl}benzoic acid

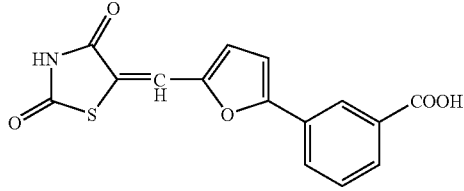

Compound 5: 4-{5-[(2,4-dioxo-1,3-thiazolidin-5-ylidene)methyl]-2-thiophyl}benzoic acid

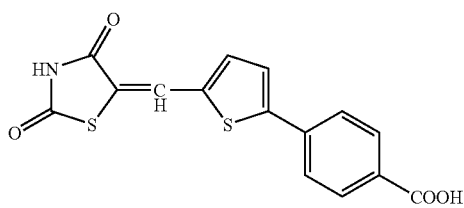

Compound 6: 4{5-[(2-sulfo-4-oxo-1,3-thiazolidin-5-ylidene)methyl]-2-furyl}benzoic acid

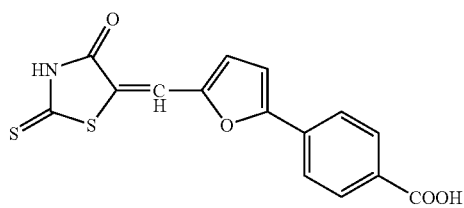

Compound 7: 4-{5-[(2,4-disulfo-1,3-thiazolidin-5-ylidene)methyl]-2-furyl}benzoic acid

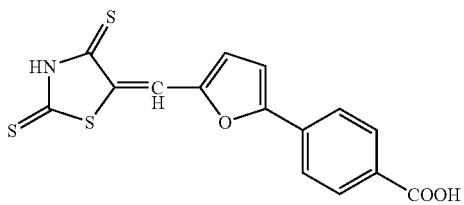

Compound 8: disodium salt of 4-{5-[(2,4-disulfo-1,3-thiazolidin-5-ylidene)methyl]-2-furyl}benzoic acid (Z isomer)

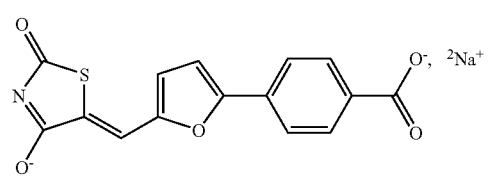

Advantageously, the compound of formula (I) is the disodium salt of 4-{5-[(2,4-disulfo-1,3-thiazolidin-5-ylidene)methyl]-2-furyl}benzoic acid, and in particular the isomer in Z form.

As other compounds of formula (I) according to the invention, exemplary are:

| Heterocyclic structure D | Appearance | LC* purity | MS** | Name |
|---|---|---|---|---|
| Compound D1 | Russet powder | 93 | M + H<br>M + Na | 5[5-(3,4-dimethoxyphenyl)-furan-2-yl-methylene]-3-ethyl-2-thioxo-oxazolidin-4-one |

-continued

| Structure | Appearance | LC purity | MS | Name |
|---|---|---|---|---|
| Compound D2 | Red powder | 100 | M + Na | 5[5-(2,5-dimethoxy-phenyl)furan-2-yl-methylene]-3-ethyl-2-thioxo-oxazolidin-4-one |
| Compound D3 | Red powder | 100 | M − H<br>M + Na | 3-ethyl-5-(5-(4-methyl-3-nitro-phenyl)furan-2-yl-methylene]-2-thioxo-oxazolidine-4-one |

| Heterocyclic structure E | Appearance | LC purity | MS | Name |
|---|---|---|---|---|
| Compound E1 | Red power | 91 | M − H<br>M + Na<br>M − H | 5-[5-(3,4-dimethoxyphenyl)-furan-2-yl-methylene]-2-thioxoimidazolidin-4-one |
| Compound E2 | Red gum | 100 | M + H<br>M − H | 5-[5-(3-hydroxymethylphenyl)furan-2-yl-methylene]-2-thioxoimidazolidin-4-one |
| Compound E3 | Orange solid | 100 | M − H | 2-thioxo-5-[5-(4-trifluoromethyl-phenyl)furan-2-yl-methylene]-imidazolidin-4-one |

-continued

| | | | | |
|---|---|---|---|---|
| 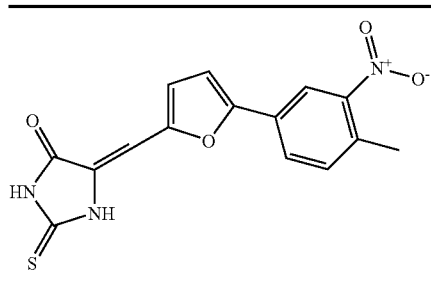  Compound E4 | Red powder | 73 | M − H | 5-[5-(4-methyl-3-nitro-phenyl)furan-2-yl-methylene]-2-thioxoimi-dazolidin-4-one |
| 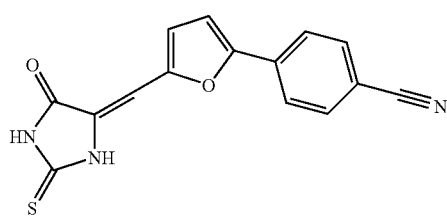  Compound E5 | Brown powder | 93 | M − H | 4-[5-(5-oxo-2-thioxoimi-dazolin-4-yl-idenemethyl)furan-2-yl]benzo-nitrile |
| 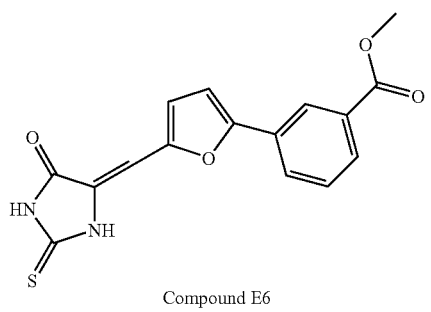  Compound E6 | Orange powder | 89 | M + H<br>M + Na<br>M − H | 3-[5-(5-oxo-2-thioxo-imidazolidin-4-yl-idenemethyl)furan-2-yl]benzoic acid methyl ester |
| 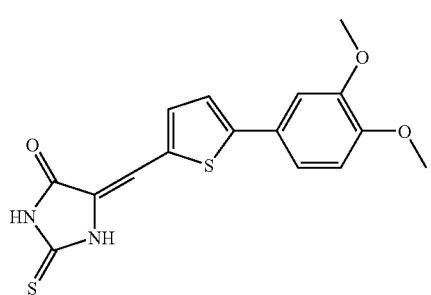  Compound E7 | Brown powder | 100 | M − H | 5-[5-(3,4-di-methoxyphenyl)-thio-phen-2-yl-methylene]-2-thioxoimi-dazolidin-4-one |
| 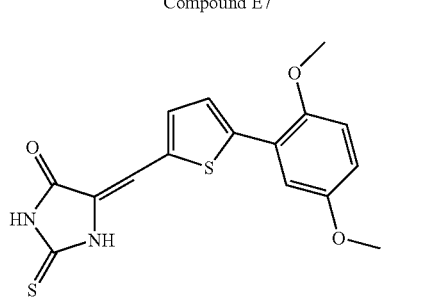  Compound E8 | Bordeaux red powder | 65 | M − H | 5-[5-(2,5-di-methoxyphenyl)-thio-phen-2-yl-methylene]-2-thioxoimi-dazolidin-4-one |

-continued

| | | | | |
|---|---|---|---|---|
| 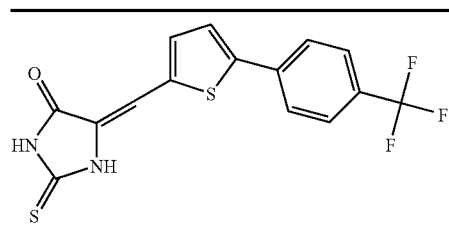  Compound E9 | Orange powder | 90 | M − H | 2-thioxo-5-[5-(4-tri-fluoromethyl-phe-nyl]thiophen-2-yl-methylene]-imi-dazolidin-4-one |
| 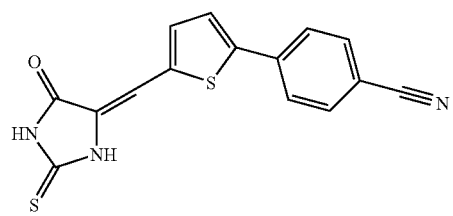  Compound E10 | Black powder | 66 | M − H | 4-[5-(5-oxo-2-thioxoimi-dazolidin-4-yl-idenemethyl)thiophen-2-yl]benzo-nitrile |
| 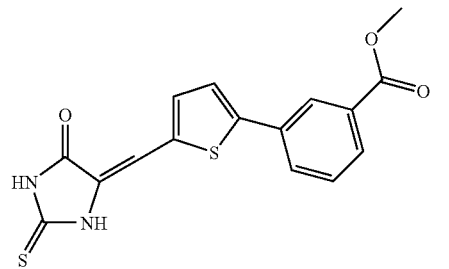  Compound E11 | Brown powder | 90 | M − H | 3-[5-(5-oxo-2-thioxo-imidazolidin-4-yl-idenemethyl)-thio-phen-2-yl]benzoic acid methyl ester |
| 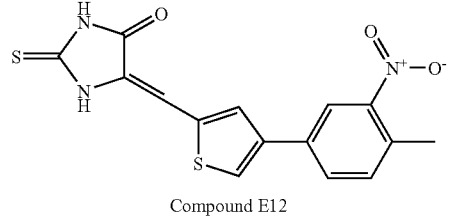  Compound E12 | Orange powder | 64 | M − H | 5-[4-(4-methyl-3-nitro-phenyl)thiophen-2-yl-methylene]-2-thioxoimi-dazolidin-4-one |
| 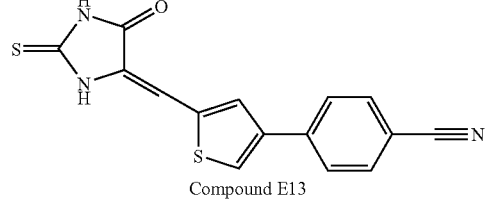  Compound E13 | Yellow powder | 53 | M − H | 4-[5-(5-oxo-2-thioxo-imi-dazolidin-4-yl-idenemethyl)-thio-phen-3-yl]benzo-nitrile |
| 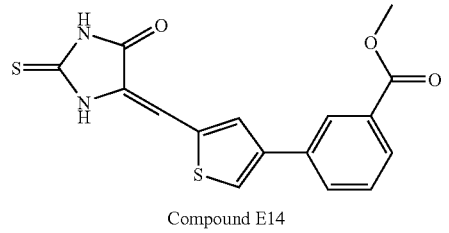  Compound E14 | Yellow powder | 91 | M − H | 3-[5-(5-oxo-2-thioxo-imidazolidin-4-yl-idenemethyl)-thio-phen-3-yl]benzoic acid methyl ester |

-continued

| Structure | Appearance | LC purity | MS | Name |
|---|---|---|---|---|
| Compound E15 | Red gum | 100 | M − H | 5-(5-phenylfuran-2-yl-methylene)-2-thioxoimi-dazolidin-4-one |
| Compound E16 | Solid orange | 81 | M − H | 5-(5-phenylthiophen-2-yl-methylene)-2-thioxo-imidazolidin-4-one |

| Heterocyclic structure F | Appearance | LC purity | MS | Name |
|---|---|---|---|---|
| Compound F1 | Orange powder | 90 | M − H | 5-[5-(3,4-di-methoxyphenyl)fur-an-2-yl-methylene]-thia-zolidine-2,4-dione |
| Compound F2 | Yellow powder | 88 | M − H | 5-(5-biphenyl-4-yl-furan-2-yl-methylene)thiazoli-dine-2,4-dione |
| Compound F3 | Yellow powder | 91 | M − H | 5[5-(3-hydroxy-methylphenyl)furan-2-yl-methylene]-thia-zolidine-2,4-dione |

-continued

| | | | | |
|---|---|---|---|---|
| 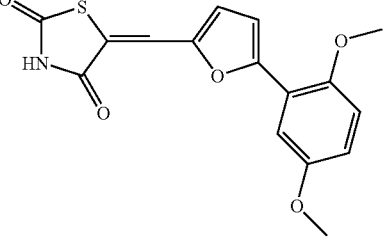<br>Compound F4 | Orange cotton | 100.00 | M − H | 5-[5-(2,5-dimethoxy-phenyl)furan-2-yl-methylene]-thia-zolidine-2,4-dione |
| 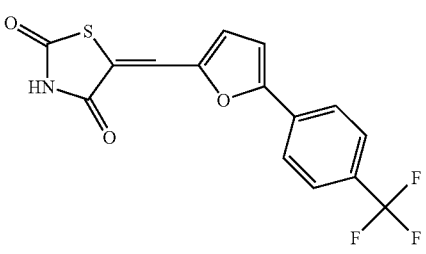<br>Compound F5 | Yellow powder | 100 | M − H | 5-[5-(4-tri-fluoromethyl-phenyl)furan-2-yl-methylene]-thia-zolidine-2,4-dione |
| 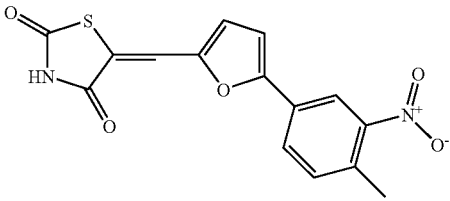<br>Compound F6 | Yellow powder | 69 | M + Na<br>M − H | 5-[5-(4-methyl-3-nitro-phenyl)furan-2-yl-methylene]-thia-zolidine-2,4-dione |
| 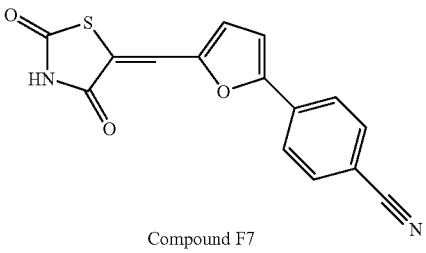<br>Compound F7 | Brown gum | 100 | M − H | 4-[5-(2,4-dioxo-thiazolidin-5-yl-idenemethyl)furan-2-yl]benzo-nitrile |
| 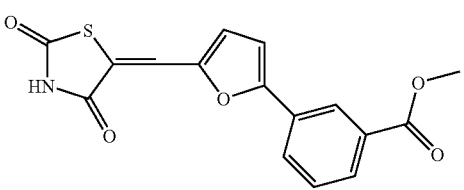<br>Compound F8 | Yellow powder | 61 | M − H | 3-[5-(3,4-dioxo-thiazolidin-5-yl-idenemethyl-furan-2-yl]benzoic acid methyl ester |
| 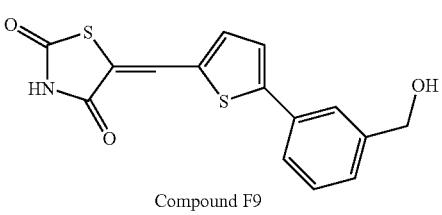<br>Compound F9 | Orange powder | 93 | M − H | 5-[5-3-hydroxy-methylphenyl)-thio-phen-2-yl-methylene]-thia-zolidine-2,4-dione |

-continued

| | | | | |
|---|---|---|---|---|
| 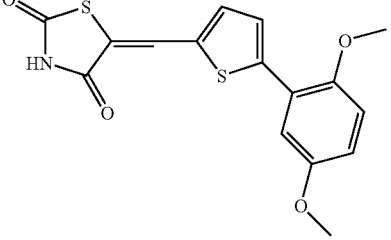 Compound F10 | Orange powder | 59 | M − H | 5[5-(2,5-dimethoxy-phenyl)thiophen-2-yl-methylene]-thia-zolidine-2,4-dione |
| 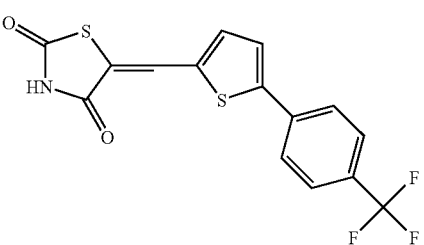 Compound F11 | Red solid | 100 | M − H | 5[5-(4-trifluoro-methylphenyl)-thio-phen-2-yl-methylene]-thia-zolidine-2,4-dione |
| 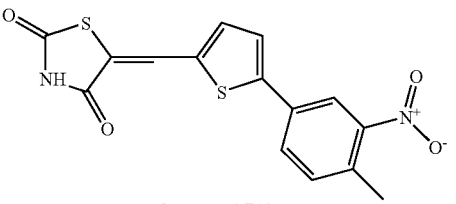 Compound F12 | Russet powder | 56 | M − H | 5-[5-(4-methyl-3-nitro-phenyl)thiophen-2-yl-methylene]-thia-zolidine-2,4-dione |
| 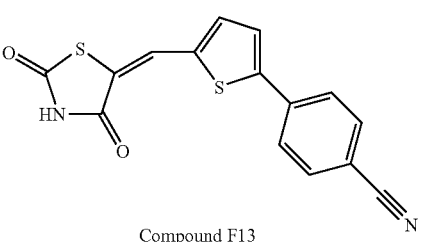 Compound F13 | Red powder | 41 | M − H | 4-[5-(2,4-dioxo-thiazolidin-5-yl-idenemethyl)-thio-phen-2-yl]benzonitrile |
| 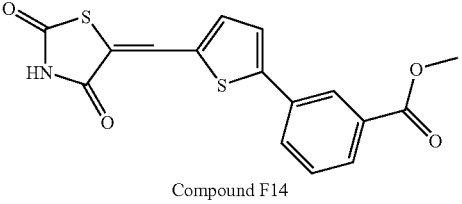 Compound F14 | Red powder | 54 | M − H | 3-[5-(2,4-dioxo-thiazolidin-5-yl-idenemethyl)-thio-phen-2-yl)benzoic acid methyl ester |
| 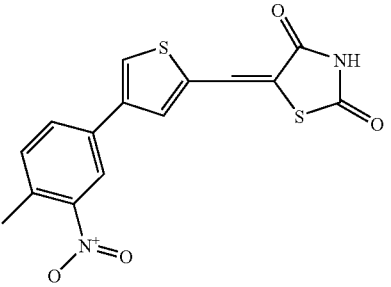 Compound F15 | Orange gum | 50 | M − H | 5-[4(4-methyl-3-nitro-phenyl)thiophen-2-yl-methylene]thiazolidine-2,4-dione |

| Structure | Appearance | LC purity | MS | Name |
|---|---|---|---|---|
| Compound F16 | Yellow powder | 59 | M − H | 3-[5-(2,4-dioxo-thiazolidin-5-yl-idenemethyl)-thiophen-3-yl]benzoic acid methyl ester |
| Compound F17 | Yellow flakes | 71 | M − H | 5-(5-phenylfuran-2-yl-methylene)-thiazolidine-2,4-dione |
| Compound F18 | Yellow powder | 84 | M − H | 5-(5-phenyl-thiophene-2-yl-methylene)-thiazolidine-2,4-dione |

| Heterocyclic structure G | Appearance | LC purity | MS | Name |
|---|---|---|---|---|
| Compound G1 | Orange powder | 62 | M − H | 2-[5-(3,4-di-methoxyphenyl)-furan-2-yl-methylene]-benzo[4,5]imidazo[2,1-b]thiazol-3-one |

*LC: liquid chromatography
**MS: mass spectrometry

The compounds according to the invention can be synthesized according to the process described hereinafter.

General procedure for synthesizing the compounds of structure D, E, F or G:

These heterocyclic structures correspond, respectively, to 3-ethyl-2-thioxo-4-oxazolidinone (CAS number: 10574-66-0, molar mass: 145, structure D), to 2-thiohydantoin (CAS number: 503-87-7, molar mass: 116, structure E), to 2,4-thiazolidinedione (CAS number: 2295-31-0, molar mass: 117, structure F), and to thiazolo(2,3-b)benzimidazol-3 (2H)-one (CAS number: 3042-01-1, molar mass: 190, structure G).

100 mg of aldehyde, 1 equivalent of heterocycle of structure D, E, F or G, 20 µl of piperidine and then 1.5 ml of absolute ethanol are placed in a Pyrex® reaction tube of the synthesis system under Discover microwave irradiation from the company Stem.

The tube is equipped with a magnetic bar and then closed by means of a crimped stopper.

The reaction medium is then irradiated in the Discover device according to the following parameters:

power released: 250W set temperature: 150° C.

irradiation time: 2 minutes maximum time to reach the set: 4 minutes.

After cooling, the reaction medium is filtered through a sintered glass filter and the solid is washed with a minimum amount of absolute ethanol and then dried under vacuum.

Yield: 40-100%

The samples are analyzed by LC-UV-MS according to the following conditions:

gradient: acetonitrile 10/water 90 to acetonitrile 90/water 10 in 8 minutes

Column: X-terra_MS C18 3.5 μm 3×50 mm

Flow rate: 0.5 ml/min

UV: 290 nm-450 nm diode array

MS: electrospray with ionization at positive and negative atmospheric pressure.

The reaction scheme for compounds 1, 3, 4 and 8 is given below by way of example.

Example I-1

Compound 1

Preparation of 4-{5-[(2,4-dioxo-1,3-thiazolidin-5-ylidene)methyl]-2-furyl}benzoic acid:

Reaction scheme:

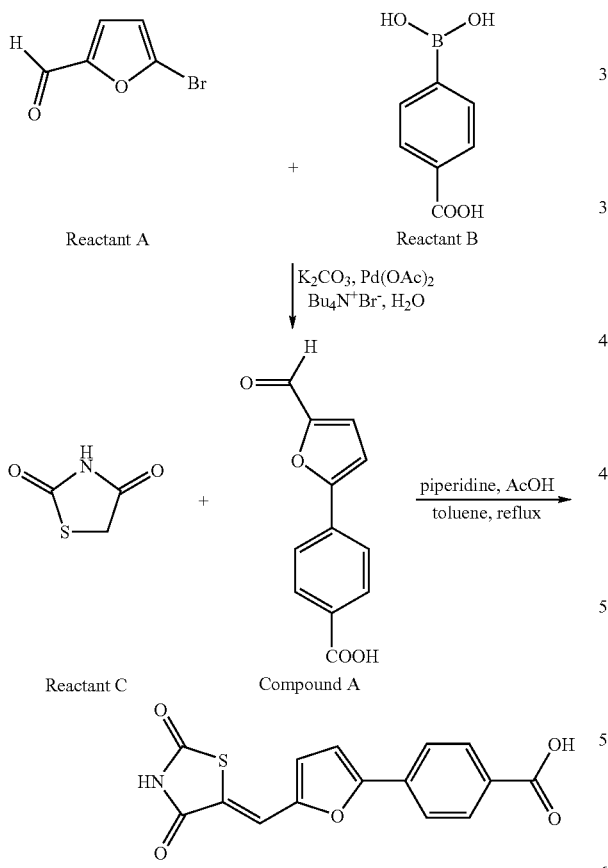

Procedure:
Stage 1:
1.99 g (6.16 mmol) of tetrabutylammonium bromide are dissolved in 100 ml of water in a 50 ml three-necked round-bottomed flask equipped with a cooling system and with a magnetic stirrer, and then 1.12 g (6.7 mmol) of 4-carboxyphenylboronic acid (reactant B), 1.08 g (6.16 mmol) of 5-bromo-2-furaldehyde (reactant A), 30 mg (2 mol %) of palladium acetate and 2.12 g (15.4 mmol) of potassium carbonate are introduced. The reaction medium is left at ambient temperature (20-25° C.) for 12 hours. The mixture is subsequently washed with ethyl acetate (3 times with 50 ml). The aqueous phase is acidified to pH=1-2 with a 35% hydrochloric acid solution. The yellow-beige solid formed (compound A) is filtered off, then rinsed with water (3 times with 20 ml) and dried under vacuum in the presence of 1.2 g of phosphorus pentoxide. The reaction yield is 90%.

Stage 2:
0.38 g (3.25 mmol) of thiazolidin-2,4-dione is dissolved in 20 ml of toluene in a 50 ml three-necked round-bottomed flask equipped with a Dean and Stark apparatus, a thermometer and a magnetic stirrer, and then 0.7 g (3.25 mmol) of yellow-beige solid formed above (compound A) is introduced. 0.15 ml of acetic acid and 0.15 ml of piperidine are subsequently added and the mixture is then brought to reflux for 5 hours. A yellow solid is formed and is filtered off and then rinsed with toluene (twice with 20 ml). The product is then dried under vacuum in the presence of 0.85 g of phosphorus pentoxide. The crude reaction yield is 78%.

Analysis:
Nuclear magnetic resonance: the spectrum obtained is in agreement with the structure proposed.

Example I-2

Compound 3

Preparation of 5-({5-[3,5-bis(trifluoromethyl)phenyl]-2-furyl}-methylene-1,3-thiazolidine-2,4-dione Reaction scheme:

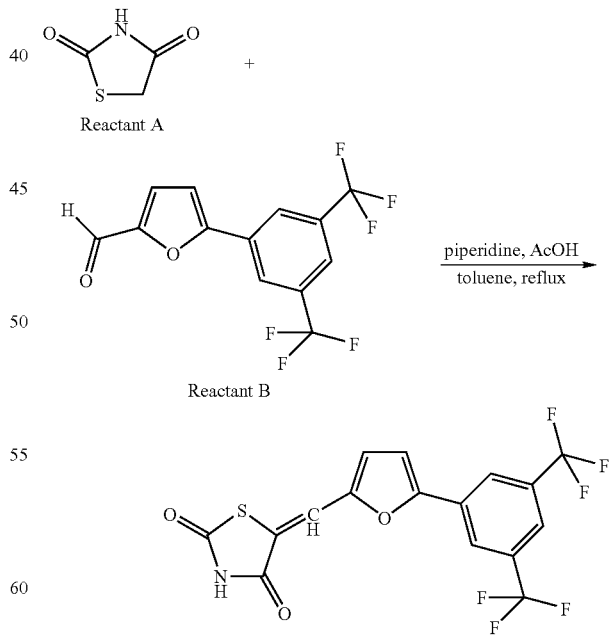

Procedure:
0.38 g (3.25 mmol) of thiazolidin-2,4-dione (reactant A) is dissolved in 20 ml of toluene in a 50 ml three-necked round-bottomed flask equipped with a Dean and Stark apparatus, a thermometer and a magnetic stirrer, and then 1 g (3.25 mmol) of 5-[3,5-bis(trifluoromethyl)phenyl]-2-furaldehyde (reactant B) is introduced. 0.15 ml of acetic acid (AcOH) and 0.15 ml of piperidine are subsequently added and the mixture is then brought to reflux for 5 hours. A yellow solid was formed during the reaction. It is filtered off, then rinsed with toluene (twice with 20 ml) and dried under vacuum in the presence of 0.86 g of phosphorus pentoxide. The reaction yield is 65%.

Analysis:

Mass spectrometry: the quasimolecular ion (M—H)— of the expected molecule, $C_{16}H_7F_6NO_3S$, is mainly detected.

Nuclear magnetic resonance: the spectrum obtained is in agreement with the structure proposed.

Example I-3

Compound 4

Preparation of 3-{5-[(2,4-dioxo-1,3-thiazolidin-5-ylidene)methyl]-2-furyl}benzoic acid Reaction scheme:

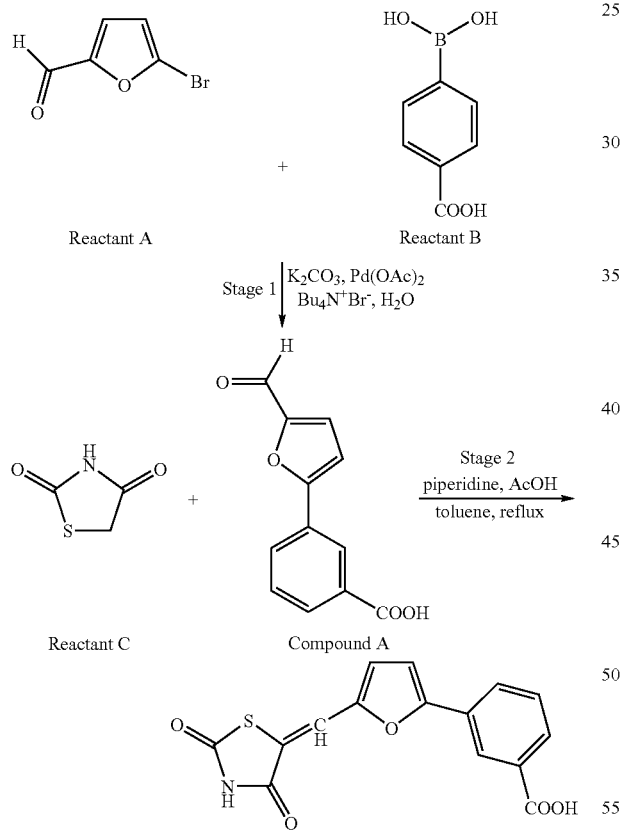

Procedure:

Stage 1:

1.99 g (6.16 mmol) of tetrabutylammonium bromide are dissolved in 100 ml of water in a 50 ml three-necked round-bottomed flask equipped with a cooling system and a magnetic stirrer, and then 1.12 g (6.7 mmol) of 3-carboxyphenylboronic acid (reactant B), 1.08 g (6.16 mmol) of 5-bromo-2-furaldehyde (reactant A), 30 mg (2 mol %) of palladium acetate and 2.12 g (15.4 mmol) of potassium carbonate are introduced. The reaction medium is left at ambient temperature (20-25° C.) for 12 hours. The mixture is subsequently washed with ethyl acetate (3 times with 50 ml). The aqueous phase is acidified to pH=1-2 with an aqueous hydrochloric acid solution: 35%. The pinkish-beige solid formed (compound A) is filtered off, then rinsed with water (3 times with 20 ml) and dried under vacuum in the presence of 1.1 g of phosphorus pentoxide. The reaction yield obtained is 82%.

Stage 2:

0.542 g (4.62 mmol) of thiazolidin-2,4-dione is dissolved in 20 ml of toluene in a 50 ml three-necked round-bottomed flask equipped with a Dean and Stark apparatus, a thermometer and a magnetic stirrer, and then 1 g (4.62 mmol) of the pinkish-beige solid formed above (compound A) is introduced. 0.15 ml of acetic acid (AcOH) and 0.15 ml of piperidine are subsequently added, and the mixture is then brought to reflux for 5 hours. The formation of a yellow solid is observed, which solid is filtered off and then rinsed with toluene (twice with 20 ml). The solid is subsequently dispersed in 100 ml of water. A 2N aqueous sodium hydroxide solution is then added until the product has completely dissolved and then acidification is carried out with a 1N aqueous hydrochloric acid solution until a pH of 1-2 is reached. The brown solid formed is filtered off, then washed with water (twice with 50 ml) and dried under vacuum in the presence of 0.86 g of phosphorus pentoxide. The yield is 63%.

Analysis:

Nuclear magnetic resonance: the spectrum obtained is in agreement with the structure proposed.

Example I-4

Compound 8

Preparation of the disodium salt of 3-{5-[(2,4-dioxo-1,3-thiazolidin-5-ylidene)methyl]-2-furyl}benzoic acid Reaction scheme:

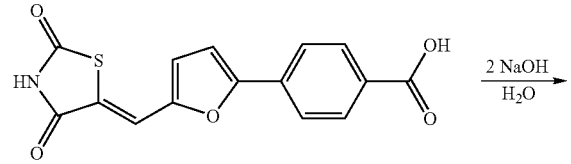

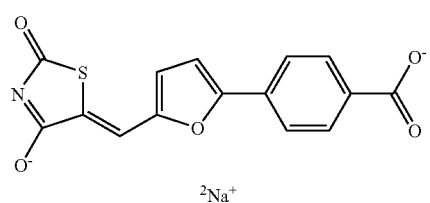

Procedure:

15 g of 3-[5-[(2,4-dioxo-1,3-thiazolidin-5-ylidene)methyl]-2-furyl}benzoic acid are dissolved in 500 ml of an aqueous sodium hydroxide solution (2 equivalents). This solution is washed twice with 50 ml of dichloromethane and then partially concentrated. This solution is then run into acetone. 11 g of an orange-yellow precipitate, corresponding to the disodium salt of 3-{5-[(2,4-dioxo-1,3-thiazolidin-5-ylidene)methyl]-2-furyl}benzoic acid, in the Z form, are thus obtained.

Analysis:

Nuclear magnetic resonance: the spectrum obtained is in agreement with the structure proposed.

Example I-5

Demonstration of the Specific Inhibitory Properties with Respect to 15-PGDH of the Compounds of Formula (I)

1) Test on 15-PGDH:

The assay is carried out as described in example 4a.

The assay values (comprising compounds (I)) are compared with the control value (comprising no compound (I)); the results indicated represent the concentration at which the compound (I) inhibits 50% of the enzyme activity of 15-PGDH, referred to as IC50 dh.

2) Test on PGFS:

The PGF synthase enzyme is obtained as described in FR-A-02/05067, at a concentration of 0.5 mg/ml, in suspension in an appropriate medium, and is blocked at −80° C. For the needs of the test, this suspension is thawed and stored in ice.

Moreover, a 100 mM Tris buffer, pH=6.5, containing 20 µM of 9.10-phenanthrenequinone* (P2896, Sigma-Aldrich, L'isle D'Abeau Chesne, BP 701, 38297, Saint Quentin Fallavier) and 100 µM of β-NAPDH (N1630, Sigma-Aldrich, L'isle D'Abeau Chesne, BP 701, 38297, Saint Quentin Fallavier), is prepared in a brown bottle (exclusion of light).

*A stock solution having a titer of 1 mM is prepared in absolute ethanol, brought to 40° C.; the flask is placed in an ultrasound tank so as to facilitate solubilization of the product.

0.950 ml of this buffer (brought beforehand to 37° C.) is introduced into the cuvette of a spectrophotometer (Perkin-Elmer, Lambda 2) thermostatically controlled at 37° C., the measuring wavelength of which is set at 340 nm. 0.05 ml of enzymatic suspension at 37° C. is introduced into the cuvette concomitantly with the recording (corresponding to a decrease in optical density at 340 nm). The maximum reaction rate is recorded.

The assay values (comprising compound (I)) are compared with the control value (comprising no compound (I)), and the results indicated represent the concentration at which compound (I) inhibits the enzyme activity of PGFS by 50%, referred to as $IC_{50}fs$.

It will be seen from this table that the $IC_{50}fs/IC_{50}dh$ ratio of compound I is greater than 13. Compound 1 therefore clearly has inhibitory activity with respect to 15-PGDH, and in particular is selective with respect to PGFS.

Example I-6

Demonstration of the Specific Inhibitory Effectiveness with Respect to 15-PGDH on a Cell Model The present study evaluates the compounds of example I in a cell model. This study makes it possible to determine the penetration of the active principle into the cytosol and also its effectiveness as a selective inhibitor of 15-PGDH, under more complex experimental conditions than a simple reaction medium.

Materials and Methods:

D-2. Culturing of U397 (CRL-1593 American Type Cells Collection) in RPMI 1640 medium+10% fetal calf serum+2 mM of L-glutamine+antibiotics, at 37° C. under 5% $CO_2$.

D-1. Preparation of a suspension of U937 ($1\times10^6$ cells/mL) in the RPMI 1640 medium+10% fetal calf serum+2 mM of glutamine+antibiotics+10 nM of PMA (phorbol 12 myristate 13 acetate); introduction of 200 µL per test well of this suspension into a 96-well plate (3 wells per molecule and per concentration to be tested+corresponding controls); incubation at 37° C. for 36 hours under 5% $CO_2$.

D0. Removal of the supernatants (the cells have adhered to the bottom of the wells: monitoring under a microscope), and introduction, into each well, of 100 µL of RPMI 1640+2 mM of L-glutamine+10 ng of lipopolysaccharide (LPS) (except absolute control)+the molecule to be tested at the desired concentration (in this case, 5 and 25 µM).

Incubation at 37° C. for 6 hours under 5% $CO_2$.

The stock solutions of molecules to be tested are at 25 mM in dimethyl sulfoxide.

All the wells contain the same final amount of DMSO.

Immediate evaluation of the amount of PGF2α secreted by the cells (50 µL) under the various conditions (molecules or controls) using an enzymatic immunoassay kit (Cayman, ref: 516011).

Results below as % of the LPS control:

| Reference molecule (5 µM) | % of the control |
| --- | --- |
| Compound 1: | +76 ± 20 |
| Compound 8: | +44 ± 16 |

This confirms that the compounds according to the invention are selective inhibitors of 15-PGDH in a cell enviroment, and protect prostaglandins.

| Compound | Structure | Inhibition of 15-PGDH $IC_{50}dh(\mu M)$ | Inhibition of PGFS $IC_{50}fs(\mu M)$ |
| --- | --- | --- | --- |
| 1 | (structure shown) | 0.3 | 4 |

The compositions hereinafter are formulated by means of the usual techniques commonly employed in the cosmetics or pharmaceutical field.

Example I-7

Hair Lotion

| | |
|---|---|
| Compound 1 | 0.80 g |
| Propylene glycol | 10.00 g |
| Isopropyl alcohol | qs 100.00 g |

This lotion is applied to the scalp one or two times daily at a rate of 1 ml per application, the scalp being slightly massaged so as to bring about the penetration of the active principle. The head of hair is subsequently dried in the open air.

Example I-8

Hair Lotion

| | |
|---|---|
| Compound 2 | 1.00 g |
| Propylene glycol | 30.00 g |
| Ethyl alcohol | 40.00 g |
| Water | qs 100.00 g |

This lotion is applied to the scalp one or two times daily at a rate of 1 ml per application, the scalp being slightly massaged so as to bring about the penetration of the active principle. The head of hair is subsequently dried in the open air.

Example I-9

Hair Lotion

| | |
|---|---|
| Compound 1 | 1 g |
| Ethyl alcohol | 40.00 g |
| NaOH | qs(*) |
| Water | qs 100.00 g |

(*) amount sufficient to neutralize the acid function carried by a phenyl ring ($R_1$).

This lotion is applied to the scalp one or two times daily at a rate of 1 ml per application, the scalp being slightly massaged so as to bring about the penetration of the active principle.

Example I-10

Hair Lotion

| | |
|---|---|
| Compound 8 | 1 g |
| Ethyl alcohol | 40.00 g |
| Propylene glycol | 30.00 g |
| Water | qs 100.00 g |

Example I-11

Wax/Water Mascara

| | |
|---|---|
| Beeswax | 6.00% |
| Paraffin wax | 13.00% |
| Hydrogenated jojoba oil | 2.00% |
| Water-soluble film-forming polymer | 3.00% |
| Triethanolamine stearate | 8.00% |
| Compound 5 | 1.00% |
| Black pigment | 5.00% |
| Preservative | qs |
| Water | qs 100.00% |

This mascara is applied to the eyelashes like a conventional mascara, with a mascara brush.

Example I-12

Hair Lotion

| | |
|---|---|
| Compound 8 | 0.10 g |
| Latanoprost | 0.10 g |
| Propylene glycol | 30.00 g |
| Ethyl alcohol | 40.00 g |
| Water | qs 100.00 g |

Example I-13

Hair Lotion

| | |
|---|---|
| Compound 8 | 1% |
| Ethyl alcohol | 49.5% |
| Water | qs 100% |

This lotion is applied to the scalp one or two times daily at a rate of 1 ml per application, the scalp being slightly massaged so as to bring about the penetration of the active principle. The head of hair is subsequently dried in the open air.

Example 5a

Effect of a Selection of 15-PGDH Inhibitors on a Melanocyte Line MeWo (Protection of $PGF_{2\alpha}$)

Methodology:
D=0

An ampoule of Mewo melanocytes (American type cell collection, HTB-65) is amplified (75 cm² flask, Costar), in DMEM medium (Gibco)+10% fetal calf serum+2 mM of L-glutamine+1% of antibiotics (Gibco). After confluence, these cells (48 hours to 72 hours) are resuspended in this same culture medium, after the action of trypsin (according to a procedure conventionally used in cell culture), in a proportion of 600 000 cells per ml.

200 µl of this suspension are introduced into n times 6 wells (n being the total number of assays, i.e., x molecules at 2 concentrations) of a 96-well plate (Costar). The plate is placed in an incubator at 37° C. under 5% $CO_2$.

D=1

Preparation, in DMSO of the 1000× stock solutions of the active agents to be evaluated (i.e., 5 and 25 mM).

Removal of the supernatants from the cultures previously prepared (96-well plate), and rinsing with 100 μl/well of DMEM medium+additives (see above description) preheated to 37° C.

Introduction of 100 μl/well of DMEM medium (+additives) containing 0.1 μl of DMSO (control) or 0.1 μl of the stock solution of the active agent to be evaluated (there are 6 assay wells per molecule and per concentration).

Practically 1 ml of solution is prepared for each of the active agents (and per concentration) to be tested, therefore 1 ml of medium+1 μl of DMSO (control) or of 1000× stock solution.

The plate is again placed in an incubator at 37° C. under 5% $CO_2$ for 4 hours, and then a $PGF_{2\alpha}$ assay is carried out on 50 μl of each of the supernatants (of the various assays) by means of an immunoenzymatic kit (according to the supplier's recommendations ($PGF_{2\alpha}$, EIA kit, ref. 516011, Cayman)).

Results (as % of the amount of $PGF_{2\alpha}$ measured under the control conditions):

| Molecules | 5 μM | 25 μM |
| --- | --- | --- |
| PhCL28A | +43% | +147% |
| Compound 1a of example I | +67% | +51% |
| Compound 8 of example I | +78% | +64% |

These results show that the selection of 15-PGDH inhibitors results in the preservation of $PGF_{2\alpha}$, compared with the control conditions.

These active agents are therefore advantageous in pigmentation insofar as prostaglandins are described for their action on melanogenesis.

Example II

As examples of pyrazole compounds according to the invention, the following compounds are representative:

Compound 1:

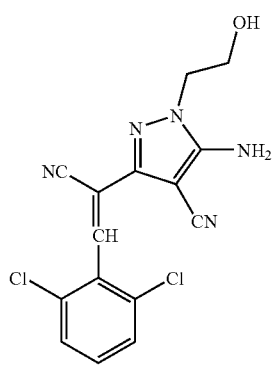

and more especially compound 1a (ring in the z position with respect to the double bond)

Compound 1a:

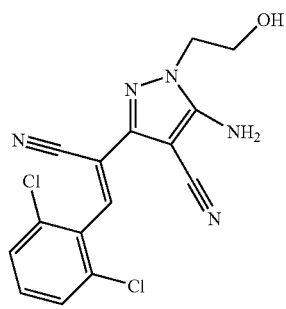

Compound 2:

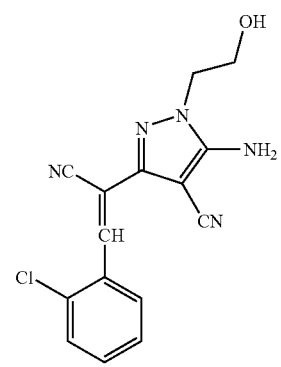

Compound 3:

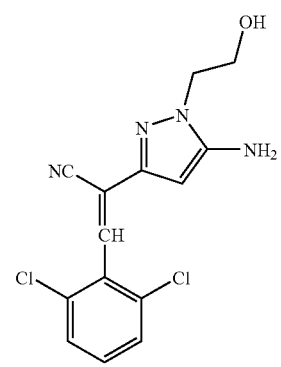

Compound 4:

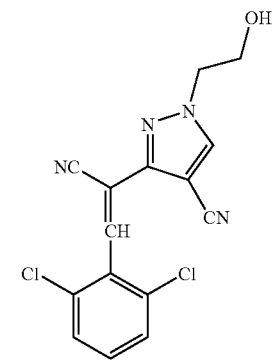

-continued

Compound 5:

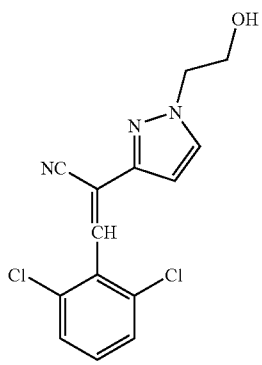

Compound 6:

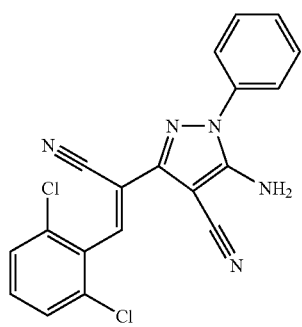

Compound 7:

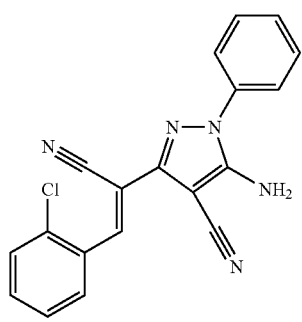

Compound 8:

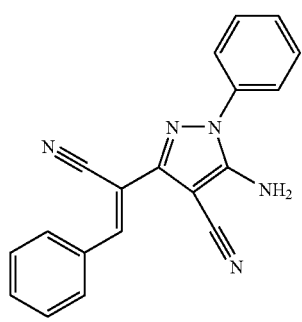

-continued

Compound 9:

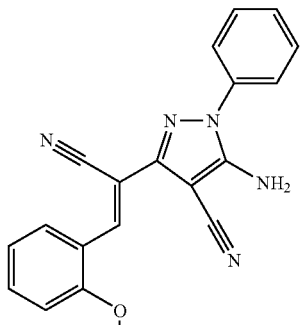

Compound 10:

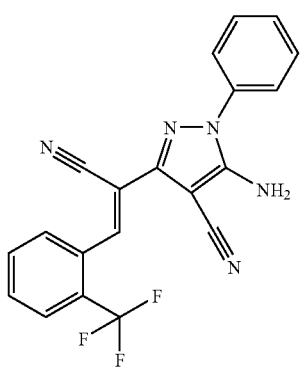

As a novel pyrazole compound of formula (I) and (III), compound 11 is exemplary.

Compound 11:

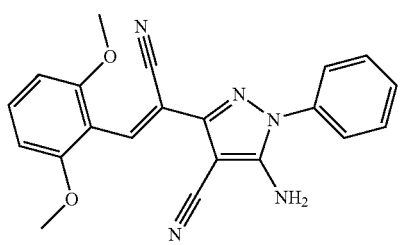

Example II-1

Procedure for the synthesis of 5-amino-3-[1-cyano-2-(2,6-dimethoxyphenyl)vinyl]-1-phenyl-1H-pyrazole-4-carbonitrile (compound 11)

1 g (4.48 mmol) of 5-amino-4-cyano-1-phenyl-3-pyrazoleacetonitrile is suspended in 15 mL of toluene, in a round-bottomed flask, under an argon atmosphere, surmonted by a Dean and Stark apparatus. 0.744 g (1 eq.) of 2,6-dimethoxybenzaldehyde and 0.030 mL of piperidine are added to the mixture. The reaction medium is refluxed overnight, and is then allowed to return to ambient temperature. A whitish precipitate forms and is filtered off and washed with toluene. The filtrate is concentrated to dryness and the residue is taken up in ethanol with agitation for 15 minutes. The suspension is filtered and the filtrate is concentrated to dryness. The residue is combined with the precipitate previously obtained, and purified on silica gel (eluent: 98/2 dichloromethane/methanol). 619 mg of product are thus obtained with a yield of 37%.

Analyses:

Mass spectrometry: (ESI +/− in $CH_3OH/H_2O$): 372 $(MH)^+$, 394$(MNa)^+$, 743$(2MH)^+$, 765$(2MNa)^+$, 370$(M-H)^-$;

Nuclear magnetic resonance: $^1H$ (400 MHz; DMSO-$d_6$) δ ppm: 3.85 (s, 6H, $OCH_3(13)$ and $OCH_3(9)$); 6.78 (d, 2H, H(10) and H(12)); 6.95 (s, 2H, $NH_2(3)$); 7.42 to 7.57 (m, 6H, H(2') to H(6') and H(11)); 7.86 (s, 1H, H(7))

Elemental Analysis:

| | | | | |
|---|---|---|---|---|
| Theory: | C 67.91%; | H 4.61%; | N 18.86%; | O 8.62% |
| Analysis: | C 67.30%; | H 4.46%; | N 18.88%; | O 8.96% |

Example II-2

Demonstration of the Specific Inhibitory Properties with Respect to 15-PGDH of the Compounds of Example II 1) Test on 15-PGDH:

The methodology is that described in example I-5.

The assay values (containing compounds tested) are compared with the control value (no compound); the results indicated represent the concentration at which compound (I) inhibits 50% of the enzyme activity of 15-PGDH, referred to as $IC_{50dh}$.

2) Test on PGF Synthase:

The methodology is that described in example I-6.

The assay values (containing the compounds tested) are compared with the control value (no compound); the results indicated represent the concentration at which compound (I) inhibits 50% of the enzyme activity of PGFS, referred to as $IC_{50fs}$.

| Compound | Structure | Inhibition of 15-PGDH $IC_{50dh}$ µM | Inhibition of PGF synthase $IC_{50fs}$ µM | Selectivity |
|---|---|---|---|---|
| 1a | 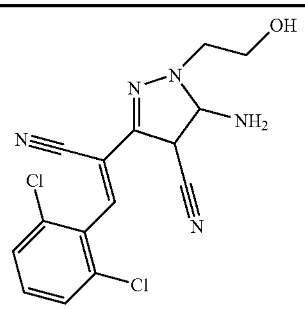 | 3 | >50 | >16.6 |
| 6 | 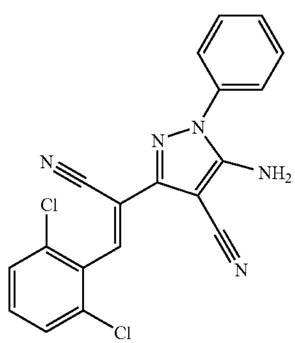 | 0.8 | >50 | >62 |
| 7 | 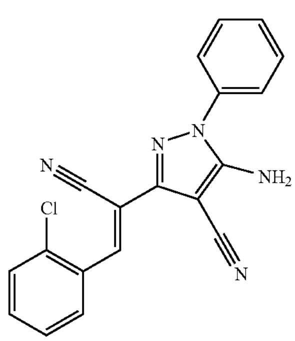 | 3 | >50 | >16 |

-continued

| Compound | Structure | Inhibition of 15-PGDH IC$_{50dh}$ µM | Inhibition of PGF synthase IC$_{50fs}$ µM | Selectivity |
|---|---|---|---|---|
| 8 | 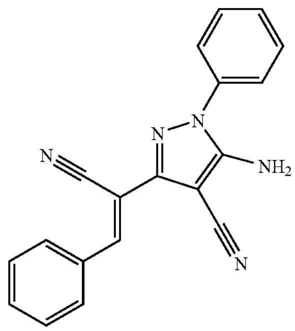 | 50 | >75 | >1.5 |
| 9 | 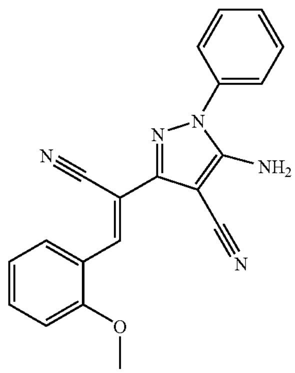 | 5 | >50 | >10 |

It will be seen from this table that the IC$_{50fs}$/IC$_{50dh}$ ratio for compounds 1a, 6, 7, 8 and 9 is >161.56. Compounds 1a, 6, 7, 8 and 9, and more especially 1a, 6, 7 and 9, therefore have selective inhibitory activity for 15-PGDH, relative to PGF synthase.

Example III
Examples of Pyrazole Compounds According to the Invention

Compound 1:

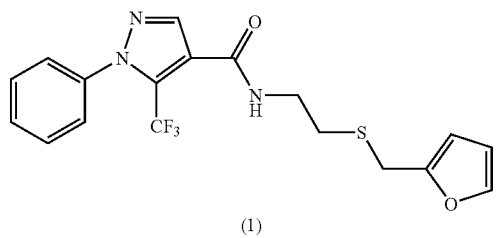

(1)

Compound 2:

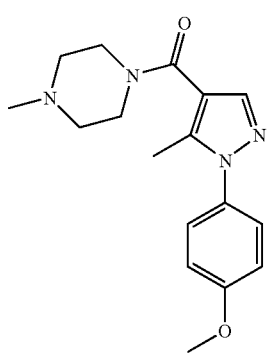

-continued

Compound 3:

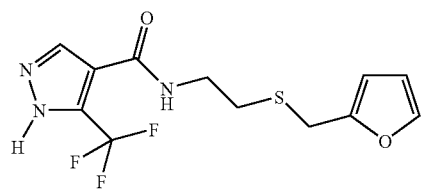

Compound 4:

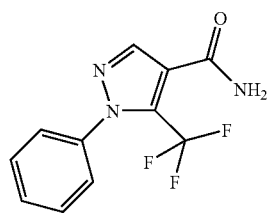

Compound 5:

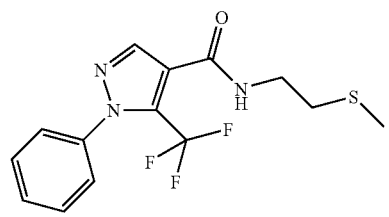

Compound 6:

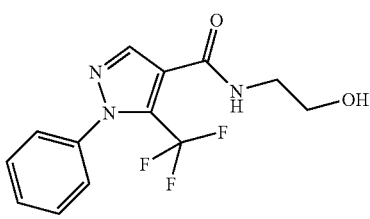

Compound 7:

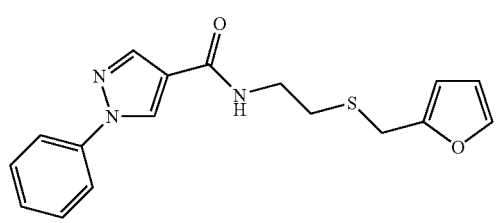

Compound 8:

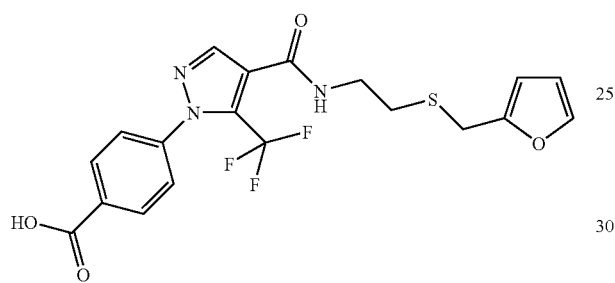

The examples of synthesis of compounds 3, 5, 6, 7 and 8 of example III are given hereinafter.

Synthesis of Compound 3

Synthesis of ethyl 5-trifluoromethyl-1H-pyrazole-4-carboxylate

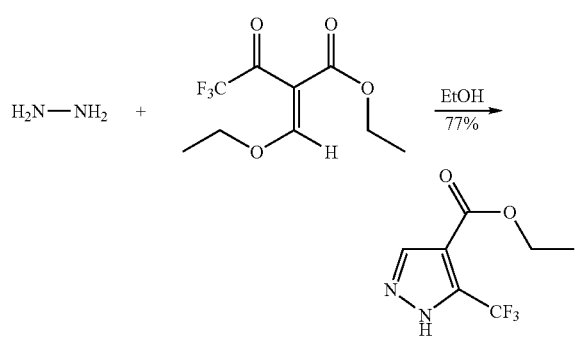

Reactants:

| | |
|---|---|
| Ethyl 2-(ethoxymethylene-4,4,4-trifluoro)-3-oxobutyrate - $C_9H_{11}F_3O_4$ | MW: 240.18 m = 4.49 g 18.71 mmol/1 eq. |
| Hydrazine (1M tetrahydrofuran) $H_4N_2$ | V = 18.71 ml 18.71 mmol/1 eq. |
| Ethanol | V = 25 ml. |

Procedure:

A 1M hydrazine solution (THF) is added to 25 mL of ethanol in a 100 ml three-necked reactor, under argon and with magnetic stirring. The suspension is cooled to −15° C. ($CCl_4/N_2$ bath) and the oxybutyrate is added to the hydrazine, dropwise, in 30 minutes.

After 2 h 30 min at ambient temperature, since no change is visible by thin layer chromatography, the reaction medium is heated at the reflux of ethanol (EtOH) for 16 hours. Once the reaction medium has returned to ambient temperature, the solvent is then evaporated off and the solid obtained is washed twice with 10 ml of pentane and filtered through a sintered glass filter.

3 g of a crystalline white solid are thus recovered (yield: 77%).

Analyses:

Beige solid for which the structure obtained is in conformity ($^1$H NMR)($^{13}$C NMR).

Synthesis of 5-trifluoromethyl-1H-pyrazole-4-carboxylic acid

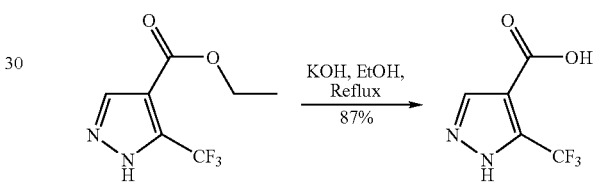

Reactants:

| | |
|---|---|
| Ethyl 5-trifluoromethyl-1H-pyrazole-4-carboxylate - $C_7H_7N_2O_2F_3$ | MW: 208.14 m = 2.97 g 14.3 mmol/1 eq. |
| Sodium hydroxide HNaO | MW: 39.99 m = 5.71 g 142 mmol/10 eq. |
| Ethanol | V = 30 ml. |

Procedure:

The pyrazole is solubilized in ethanol in a 250 ml reactor, with magnetic stirring. After 15 minutes at ambient temperature, a 1.2N sodium hydroxide solution (120 ml of water) is added. The reaction medium is then refluxed for 18 h.

The solution is subsequently brought back to 10° C. and then acidified with 1N HCl. After evaporation under reduced pressure of all the ethanol and of two thirds of the water, the white precipitate formed is recovered by filtration through a sintered glass filter, washed with water, and then dried under a strong vacuum.

The fine white powder (2.30 g) obtained is characterized and corresponds to the expected product (yield: 87%).

Analyses:

White solid for which the structure obtained is in conformity ($^1$H NMR)($^{13}$C NMR).

Synthesis of N-{2-[(2-furylmethyl)thio]ethyl}-5-trifluoromethyl-1H-pyrazole-4-carboxylic acid

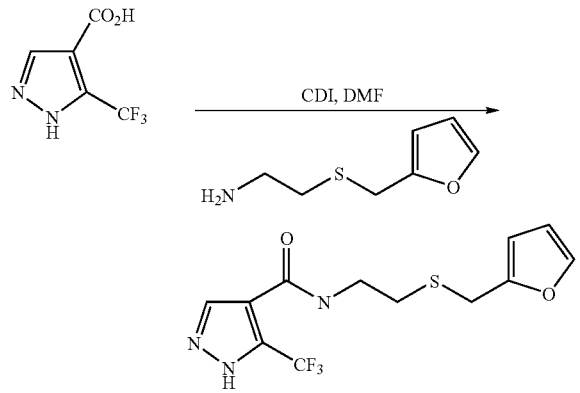

Reactants:

| | | |
|---|---|---|
| 5-Trifluoromethyl-1H-pyrazole-4-carboxylic acid | $C_5H_3N_2O_2F_3$ | MW: 180.08 m = 0.80 g 4.44 mmol/1 eq |
| Carbonyldiimidazole {CDI} - | $C_7H_6N_4O$ | MW: 162.15 m = 0.815 g 5.39 mmol/1.4 eq. |
| 2-(Furfurylthio)ethylamine - | $C_7H_{11}NOS$ | MW: 157.234 m = 3.22 g 21.9 mmol/4.6 eq. |
| Dimethylformamide | | V = 10 ml |

Procedure:

The pyrazole is solubilized in DMF in a 100 ml reactor under nitrogen and with magnetic stirring. CDI is then added rapidly in a single portion and the mixture is kept stirring for approximately 45 minutes. A persistent insoluble product is observed. The amine is then rapidly added dropwise using a syringe. After overnight stirring, the reaction medium is poured into 100 ml of an ice/water mixture. The white precipitate formed is recovered by filtration and the filtrate is extracted with ethyl acetate (2×25 ml). The organic phase is added to the precipitate and concentrated to dryness.

This crude mixture is then chromatographed on silica gel (flash chromatography, elution with 3/1 hexane/ethyl acetate, 1% aqueous ammonia). The fraction corresponding to the expected product (Rf: 0.45 in $CH_2Cl_2/1\%\ NH_3$) is then isolated and concentrated to dryness. The oil obtained is taken up in 2 ml of ethanol and poured into 100 ml of an ice/water mixture. The precipitate obtained is recovered by filtration, filtered through a sintered glass filter, and concentrated to dryness.

402 mg of a white solid are thus obtained (yield: 30%).

Analyses:

White solid $^1$H NMR: (DMSO); 7.93 (s, 1H, CH pyrazole), 7.26 (s, 1H, CH furyl), 7.19 (m, 2H, NH+CONH), 6.10 (d, 2H, H furyl), 3.61 (, 2H, $CH_2$), 3.37 (q, 2H, $CH_2$), 2.43 (t, 2H, $CH_2$). $^{13}$C NMR: (DMSO/$CDCl_3$); 158.43 (CONH), 143.1 (CH), 111.4 (2CH), 108.7 (CH), 39.3 ($CH_2$), 32.1 ($CH_2$), 28.8 ($CH_2$). Quaternary carbons not visible due to the small amount of compound in the tube.

Synthesis of Compounds 5 and 6

Synthesis of ethyl 5-methyl-1-phenyl-1H-pyrazole-4-carboxylate

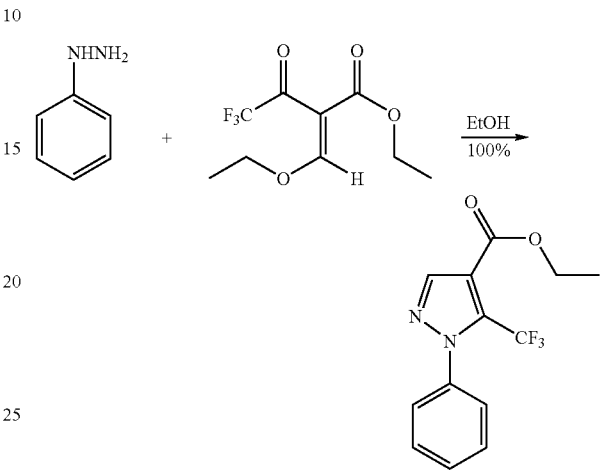

Reactants:

| | | |
|---|---|---|
| Ethyl 2-(ethoxymethylene-4,4,4-trifluoro-3-oxobutyrate - | $C_9H_{11}F_3O_4$ | MW: 240.18 m = 15.00 g 62 mmol/1 eq. |
| Phenylhydrazine - | $C_7H_8N_2O_2$ | MW: 108.14 m = 6.38 g 60 mol/1.1 eq. |
| Ethanol | | V = 500 ml |

Procedure:

The phenylhydrazine is suspended in 500 ml of absolute ethanol in a 1 l three-necked reactor under argon and with magnetic stirring. The solution is cooled to −15° C. ($CCl_4/N_2$ bath) and the oxobutyrate is added to the hydrazine, dropwise, in 45 minutes. After 4 h at ambient temperature, the solution is concentrated to dryness. The yellow powder obtained is washed with pentane and dried under vacuum, and 18.5 g of a white solid are thus isolated (yield: greater than 100%).

Analyses:

White solid for which the structure obtained is in conformity ($^1$H NMR)($^{13}$C NMR).

Synthesis of ethyl 5-methyl-1-phenyl-1H-pyrazole-4-carboxylate

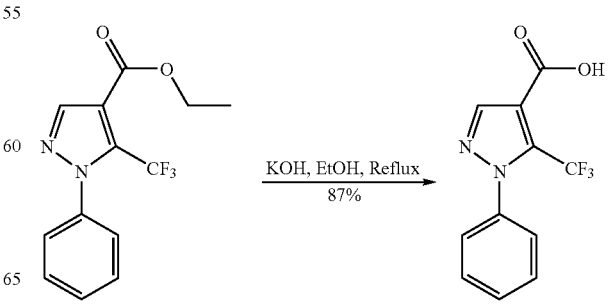

Reactants:

| | |
|---|---|
| Ethyl 5-trifluoromethyl-1-phenyl-1H-pyrazole-4-carboxylate - $C_{21}H_{17}N_2O_4F_3$ | MW: 418.37 m = 18.5 g 65 mmol/1 eq. |
| Potassium hydroxide (85%) HKO | MW: 56.11 m = 6.43 g 97.5 mmol/1.5 eq. |
| Ethanol | V = 150 ml |

Procedure:

The pyrazole is added to a solution of potassium hydroxide in ethanol in a 250 ml reactor with magnetic stirring. After 15 minutes at ambient temperature, the reaction medium is then refluxed for 3 h. Once it has been brought back to ambient temperature, the solution is added to 600 ml of water. The mixture is washed 3 times with 250 ml of ether. The aqueous phase is acidified with 37% HCl until pH=1 is reached. The residual ethanol is evaporated off and a yellow precipitate appears in solution. The precipitate is filtered through a sintered glass filter, washed with water, and dried under a strong vacuum for 72 hours.

14.5 g of a yellow powder are thus obtained (yield: 87%).

Analyses: Yellow solid for which the structure obtained is in conformity ($^1$H NMR)($^{13}$C NMR).

Synthesis of N-(2-methylthioethyl)-1-phenyl-5-trifluoromethyl-1H-pyrazole-4-carboxamide (compound 5)

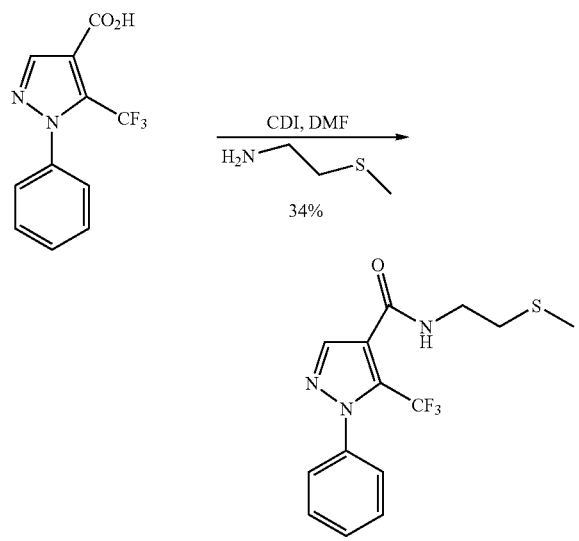

Reactants:

| | |
|---|---|
| 1-Phenyl-5-trifluoromethyl-1H-pyrazolecarboxylic acid - $C_{10}H_8N_2O_2$ | MW: 188.19 m = 1.20 g 4.71 mmol/1 eq. |
| Carbonyldiimidazole (CDI) - $C_7H_6N_4O$ | MW: 162.15 m = 0.88 g 5.42 mmol/1.15 eq. |
| 2-Thiomethylethylamine - $C_3H_9NS$ | MW: 91.18 m = 2.00 g 21.97 mmol/4.7 eq. |
| DMF | V = 8.3 ml |

Procedure:

The pyrazole is solubilized in DMF in a reactor under nitrogen and with magnetic stirring. CDI is then added rapidly in a single portion and the mixture is kept stirring for approximately 20 minutes. The amine is then rapidly added dropwise by means of a syringe. After stirring for 3 h, TLC monitoring of the reaction indicates that the starting product has completely disappeared.

The reaction medium is then poured into 80 ml of an ice/water mixture. The white precipitate formed after stirring for 15 minutes is then recovered by filtration through a sintered glass filter, and dried by suction. The orangey solid obtained is then taken up in 50 ml of ethyl ether, washed once with water, and dried over sodium sulfate. After filtration through a sintered glass filter and evaporation under partial vacuum, 0.8 g of a yellow solid is thus obtained. After having been again taken up in 50 ml of dichloromethane and then dried over sodium sulfate, the product is chromatographed on silica (elution: 7/3 hexane/ethyl acetate) and then recrystallized from toluene, to give 530 mg of a white solid (yield: 34%), which is characterized by NMR in monohydrate form (peak at 1.6 ppm).

Analyses:

White Solid $^1$H NMR: (CDCl$_3$); 7.93 (s, 1H, H pyrazole), 7.52-7.32 (m, 5H, H arom.) 6.35 (m, 1H, NH), 3.68 (q, 2H, CH$_2$), 2.72 (t, 2H, CH$_2$), 2.15 (s, 3H, CH$_3$), $^{13}$C NMR: (CDCl$_3$); 161.7 (CO—NH), 140.0 (CH arom.) 139.6 (C arom.), 130.3 (CH arom.), 129.8 (C), 129.6 (2 CH arom.), 126.2 (2 CH arom.), 121.2 (C), 119 (not visible, CF$_3$), 38.3 (CH$_2$), 34.0 (CH$_2$), 15.2 (CH$_3$).

Synthesis of N-(2-hydroxyethyl)-1-phenyl-5-trifluoromethyl-1H-pyrazole-4-carboxamide (compound 6)

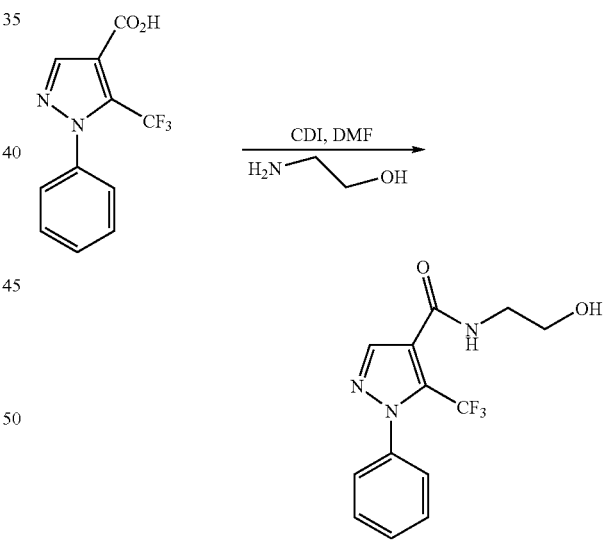

Reactants:

| | |
|---|---|
| 1-Phenyl-5-trifluoromethyl-1H-pyrazolecarboxylic acid - $C_{10}H_8N_2O_2$ | MW: 188.19 m = 0.83 g 4.41 mmol/1 eq. |
| Carbonyldiimidazole (CDI) - $C_7H_6N_4O$ | MW: 162.15 m = 0.82 g 5.05 mmol/1.15 eq. |
| 2-Ethanolamine - $C_2H_7NO$ | MW: 61.08 m = 1.34 g 20.5 mmol/4.7 eq. |
| DMF | V = 10 ml |

Procedure:

The pyrazole is solubilized in DMF in a reactor under nitrogen and with magnetic stirring. CDI is then added rapidly in a single portion and the mixture is kept stirring for approximately 20 minutes. The amine is then rapidly added dropwise by means of a syringe. After stirring for 3 h, TLC monitoring of the reaction indicates that the starting product has completely disappeared.

The reaction medium is then poured into 75 ml of an ice-water mixture. The white precipitate formed after stirring for 15 minutes is then recovered by filtration through a sintered glass filter and dried by suction. The orangey solid obtained is then taken up in 50 ml of dichloromethane, washed once with water, and dried over sodium sulfate. After filtration through a sintered glass filter and evaporation under partial vacuum, 1.1 g of a yellow solid are thus obtained.

The latter is taken up in a minimum amount of toluene, but the product is found to be partially soluble in the solvent. The product is therefore recrystallized under cold conditions, so as to give the formation of 470 mg of a white solid (yield: 33%), which is characterized in the form of a derivative associated with 0.5 molecule of water.

Analyses:

White Solid $^1$H NMR: (CDCl$_3$); 7.93 (s, 1H, H pyrazole), 7.60-7.20 (m, 5H, H arom.) 6.48 (m, 1H, NH), 3.85 (t, 2H, CH$_2$), 3.63 (t, 2H, CH$_2$), 2.00 (broad s, 2H, OH+H$_2$O). $^{13}$C NMR: (CDCl$_3$); 162.4 (CO—NH), 140.0 (CH arom.) 139.4 (C arom.), 130.4 (CH arom.), 130.3 (C), 129.6 (2 CH arom.), 126.2 (2 CH arom.), 121.1 (C), 119.8 (q, CF$_3$).

Synthesis of Compound 7

Synthesis of 1-phenyl-1H-pyrazolecarbaldehyde

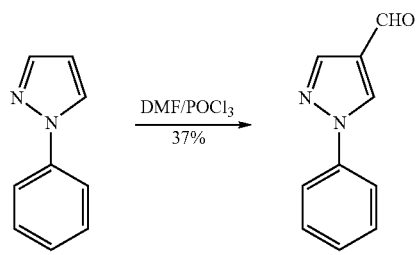

Reactants:

| | |
|---|---|
| 1-Phenyl-1H-pyrazole - C$_2$H$_3$N [75-05-8] | MW: 41.05 V = 39.9 ml |
| | 77 mmol/1 eq. |
| DMF - C$_2$H$_6$O [64-17-5] | MW: 46.06 V = 1.1 l |
| Phosphorus oxychloride [7803-49-8] | MW: 33.03 V = 100 ml |
| | 1.63 mmol/2.13 eq. |

Procedure: (Vilsmeier-type formylation reaction)

A 100 ml reactor, under nitrogen and with magnetic stirring, is loaded with 10 ml of DMF which are immediately cooled to 0° C. by means of an ice/water bath. The phosphorus oxychloride is added dropwise, by means of a syringe, in 12 minutes. After 1 hour at 0° C., a solution of 1-phenylpyrazole (in 10 ml of DMF) is added in 2 minutes by means of a syringe, by rapidly running it in dropwise. After a further 5 minutes at 0° C., the mixture is brought back to ambient temperature for 15 minutes and then placed at 100° C. for 2 h 30 min. Complete disappearance of the starting product is observed by TLC (9/1 hexane/acetic acid (EtOAc): Rf: 0.35). Once it has returned to ambient temperature, the reaction medium is carefully added to 20 g of ice-cold water, under a hood.

After stirring for 18 hours, the mixture is extracted twice with 250 ml of ethyl acetate. The combined organic phases are dried over sodium sulfate, filtered through a sintered glass filter, and evaporated to dryness, and the residue is then filtered through a patch of silica on a sintered glass filter (elution: pure hexane, 8/2 hexane/CH$_2$Cl$_2$, 1/1 hexane/CH$_2$Cl$_2$, 100% CH$_2$Cl$_2$). The purely chlorinated fractions make it possible to isolate 1.17 g of a yellow oil, which crystallizes spontaneously once taken up in hexane. A second fraction (eluted with 1/1 hexane/CH$_2$Cl$_2$) taken up with hexane also makes it possible to isolate a solid. The solids are combined and washed three times with 10 ml of hexane so as to obtain 2.21 g of a white solid (yield 37%).

Analyses:

White Solid

TLC: (pure dichloromethane): Rf: 0.05 (UV), $^1$H NMR, $^{13}$C NMR.

Synthesis of 1-phenyl-1H-pyrazolecarboxylic acid

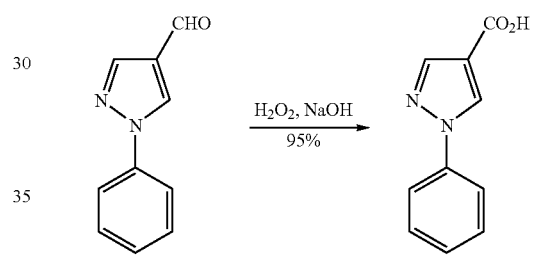

Reactants:

| | |
|---|---|
| 1-Phenyl-1H-pyrazolecarbaldehyde - C$_{10}$H$_8$N$_2$O | MW: 172.18 m = 2.12 g |
| | 12.31 mmol/1 eq. |
| H$_2$O$_2$ (30% aqueous.) - H$_2$O$_2$ | MW: 34.01 m = 8.02 g |
| | 70.6 mmol/6.1 eq. |
| Sodium hydroxide HNaO | MW: 40.0 m = 1.04 g |
| | 26 mmol/2.1 eq. |

Procedure:

The sodium hydroxide is dissolved in 20 ml of water in a 100 ml three-necked reactor under nitrogen and with magnetic stirring. The pyrazole is then added in a single step. A persistent insoluble product is observed, even at a temperature of 45-50° C. The hydrogen peroxide is added to the suspension in 6 portions over 50 minutes. After 5 hours at 50° C., TLC monitoring makes it possible to observe that a substantial part of the substrate remains. 10 ml of 1N NaOH (0.4 g of NaOH) and 5 g of aqueous hydrogen peroxide are added. After stirring for a further hour at 50° C., the insoluble product has completely disappeared and TLC monitoring makes it possible to observe that the starting product has been entirely consumed (visualization: dinitrophenylhydrazine).

The reaction medium brought back to ambient temperature is then added to 150 ml of an ice/2N HCl mixture (2/1). The white precipitate formed is filtered through a Buchner funnel after stirring for 30 minutes and washed 3 times with water.

After having been resolubilized in 250 ml of ethyl acetate, dried over $MgSO_4$ and then filtered and evaporated to dryness, 2.25 g of a white product are thus isolated (yield: 96%).

Analyses:

White solid for which the structure obtained is in conformity ($^{H}1$ NMR)($^{13}C$ NMR).

Synthesis of N-{2-[(2-furylmethyl)thio]ethyl}-1-phenyl-1H-pyrazole-4-carboxamide

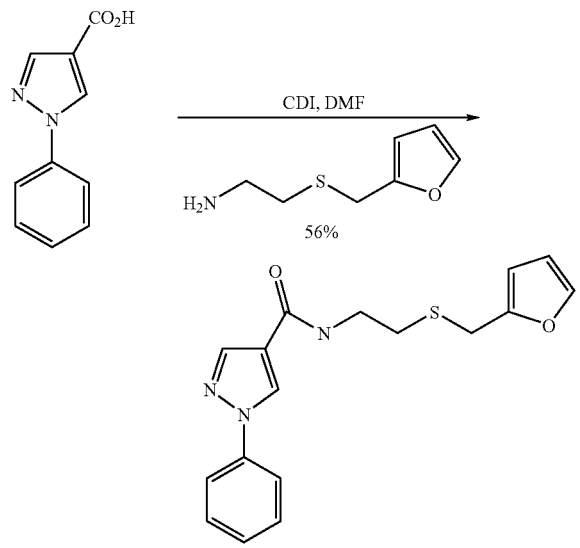

Reactants:

| | |
|---|---|
| 1-Phenyl-1H-pyrazolecarboxlic acid - $C_{10}H_8N_2O_2$ | MW: 188.19 m = 0.83 g 4.41 mmol/1 eq. |
| Carbonyldiimidazole (CDI) - $C_7H_6N_4O$ | MW: 162.15 m = 0.82 g 5.05 mmol/1.15 eq. |
| 2-(Furfurylthio)ethylamine - $C_7H_{11}NOS$ | MW: 157.234 m = 3.23 g 20.5 mmol/4.7 eq. |
| DMF | V = 10 ml |

Procedure:

The pyrazole is solubilized in DMF in a reactor under nitrogen and with magnetic stirring. CDI is then rapidly added in a single portion and the mixture is kept stirring for approximately 20 minutes. The amine is then rapidly added dropwise by means of a syringe. After stirring for 3 h 30 min, TLC monitoring of the reaction indicates that the starting product has completely disappeared.

The reaction medium is then poured into 80 ml of an ice/water mixture. The white precipitate formed after stirring for 15 minutes is then recovered by filtration through a sintered glass filter and dried by suction. The orangey solid obtained is then taken up in 50 ml of dichloromethane, washed once with water, and dried over sodium sulfate. After filtration through sintered glass filter and evaporation under partial vacuum, 0.8 g of a yellow solid is thus obtained.

The latter is chromatographed on silica (elution: 7/3 hexane/ethyl acetate) and then recrystallized from toluene.

0.80 g of a beige solid is thus recovered (yield: 56%). It is characterized in the form of a compound associated with half a molecule of water.

Analyses:

Beige Solid

TLC (3/7 hexane/EtOAc): Rf=0.70. $^1H$ NMR: ($CDCl_3$); 8.38 (s, 1H, CH), 7.95 (s, 1H, CH), 7.72 (m, 2H, H arom.), 7.45 (m, 2H, H arom.), 7.36 (m, 2H), 6.31 (m, 3H, 2CH+NH), 3.78 (s, 2H, S—$CH_2$), 3.60 (q, 2H, N—$CH_2$), 2.78 (t, 2H, $CH_2$—S). $^{13}C$ NMR: ($CDCl_3$); 162.5 (CO), 151.6 (C), 14.5 (CH), 139.7 (2 CH), 139.4 (C), 129.8 (CH), 128.6 (CH), 127.6 (CH), 120.3 (C), 119.7 (CH), 110.8 (CH), 108.1 (CH), 38.2 ($CH_2$), 31.8 ($CH_2$), 28.2 ($CH_2$).

Synthesis of Compound 8

Synthesis of 4-[4-(ethoxycarbonyl)-5-methyl-1H-pyrazol-1-yl]benzoic acid

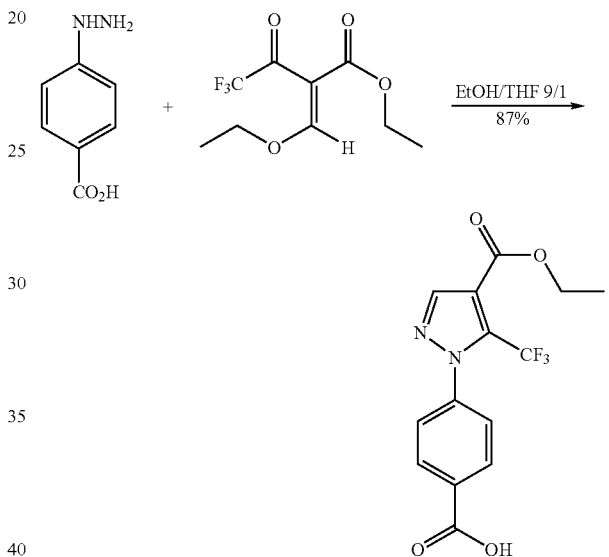

Reactants:

| | |
|---|---|
| Ethyl 2-(ethoxymethylene-4,4,4-trifluoro)-3-oxobutyrate - $C_9H_{11}F_3O_4$ | MW: 240.18 m = 6.50 g 27.07 mmol/1 eq. |
| 4-Hydrazinobenzoic acid - $C_7H_8N_2O_2$ | MW: 152.17 m = 4.12 g 27.07 mmol/1 eq. |
| Ethanol | V = 90 ml |
| THF | V = 10 ml |

Procedure:

The hydrazinobenzoic acid is suspended in 90 ml of absolute ethanol in a 250 ml three-necked reactor under argon and with magnetic stirring. 10 ml of THF are added so as to promote solublization of the reactant (without success). The suspension is cooled to −15° C. ($CCl_4/N_2$ bath) and the oxobutyrate is added to the hydrazine dropwise in 30 minutes. After 2 h 30 mm at ambient temperature, the solution has become completely clear (1 single spot visible by TLC with a characteristic visualization of pyrazoles by UV at 254 nm). The solvent is then evaporated off and the yellow solid obtained is washed twice with 20 ml of pentane and filtered through a sintered glass filter. The yellow powder obtained is dried under vacuum and 7.70 g of a beige solid are thus isolated (yield: 87%).

Analyses:

Beige solid for which the structure obtained is in conformity (TLC, $^1$H NMR, $^{13}$C NMR).

Synthesis of 1-(4-carboxyphenyl)-5-trifluoromethyl-1H-pyrazole-4-carboxylic acid

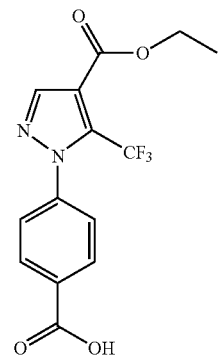 NaOH, EtOH, Reflux / 77% → 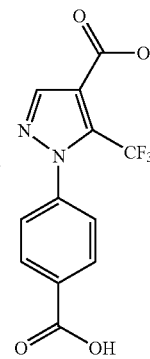

Reactants:

| | |
|---|---|
| 4-[4-(ethoxycarbonyl)-5-methyl-1H-pyrazol-1-yl]benzoic acid - $C_{14}H_{11}N_2O_4F_3$ | MW: 328.24 m = 3.25 g<br>9.9 mmol/1 eq. |
| Sodium hydroxide HNaO | MW: 39.99 m = 1.38 g<br>150 mmol/15 eq. |
| Ethanol | V = 30 ml |

Procedure:

The pyrazole is dissolved in ethanol in a 100 ml reactor (equipped with a cooling system) with magnetic stirring. After 15 minutes at ambient temperature, a solution of sodium hydroxide (1.38 g in 50 ml of water) is added. The reaction medium is stirred at ambient temperature for 5 minutes and then refluxed for 13 h.

The mixture is then returned to ambient temperature and acidified with a 3N HCl solution. The white precipitate obtained is then filtered through a sintered glass filter, rinsed with water, and then dried in a rotary evaporator and then with a drying pump.

2.03 g of solid are thus obtained (yield: 77%).

Analyses:

White solid for which the structure is in conformity ($^1$H NMR)($^{13}$C NMR).

Synthesis of 4-{4-[({2-[(2-furylmethyl)-thio]ethyl}amino)carbonyl]-5-trifluoromethyl-1H-pyrazol-1-yl}benzoic acid

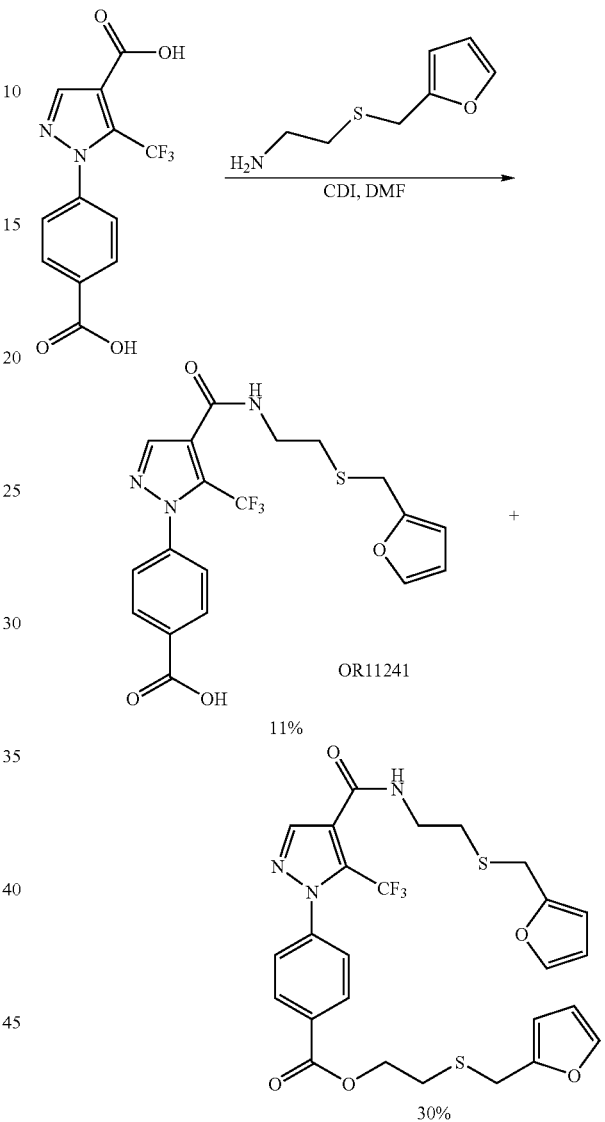

Reactants:

| | |
|---|---|
| 1-(4-Carboxyphenyl)-5-trifluoromethyl-1H-pyrazole-4-carboxylic acid - $C_{12}H_7N_2O_2F_3$ | MW: 268.19 m = 1.03 g<br>3.04 mmol/1 eq. |
| Carbonyldiimidazole (CDI) - $C_7H_6N_4O$ | MW: 162.15 m = 0.81 g<br>5.0 mmol/1.3 eq. |
| 2-(Furfurylthio)ethylamine - $C_7H_{11}NOS$ | MW: 157.23 m = 2.25 g<br>14.3 mmol/4.7 eq. |
| DMF | V = 12 ml |

Procedure:

The pyrazole is solubilized in DMF in a reactor under nitrogen and with magnetic stirring. CDI is then added rapidly in a single portion and the mixture is kept stirring for approximately 30 minutes. The amine is then rapidly added dropwise by means of a syringe. After overnight stirring, TLC monitoring of the reaction indicates that the starting product has completely disappeared.

The reaction medium is then poured into 100 ml of an ice/water mixture. The white precipitate formed after stirring for 15 minutes is then recovered by filtration through a sintered glass filter and dried by suction. The white solid obtained is then analyzed (TLC, NMR) and two products are thus identified. This crude mixture is then chromatographed on silica gel (flash chromatography, elution with hexane/ethyl acetate 2/1 and then 1/1 with 1% of formic acid).

The first fraction (Rf: 0.65 in pure $CH_2Cl_2$, 1% $HCO_2H$) contains 140 mg of the expected product (yield 11%). The identification was carried out by NMR, by analogy with the other compounds synthesized.

The second fraction (Rf: 0.48) contains 500 mg of the product having two amide functions (30% yield).

Analyses:

White solid for which the structure obtained is in conformity ($^1H$ NHR; $^{13}C$ NMR).

Example IV

Examples of 2-alkylideneaminooxyacetamide Compounds that can be used in the Invention Compound 1: N-phenyl-2-({[(1Z)-1-thien-2-ylethylidene]-amino}oxy)acetamide

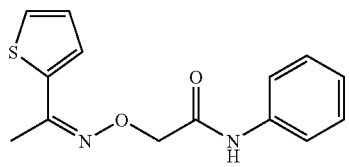

Compound 2: 2-({[(1Z)-1-(furyl)ethylidene]amino}oxy)-N-phenylacetamide

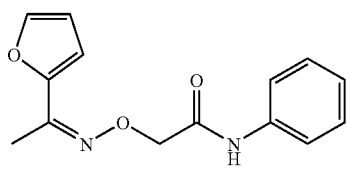

Compound 3: N-(4-Methoxyphenyl)-2-({[(1Z)-1-thien-2-ylethylidene]amino}oxy)acetamide

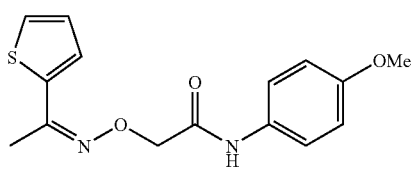

Compound 4: N-Phenyl-2-({[(1Z)-1-thien-2-ylpropylidene]-amino}oxy)acetamide

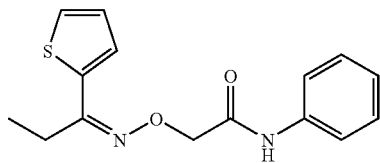

Compound 5: 2-{[(1-methylethylidene)amino]oxy}-N-phenylacetamide

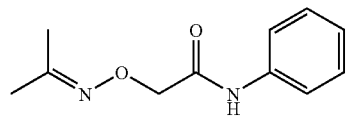

Compound 6: N-Methyl-2-({[(1Z)-1-thien-2-ylethylidene]-amino}oxy)acetamide

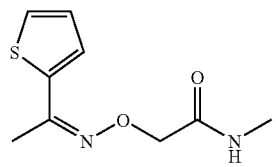

Compound 7: 7N-Methyl-N-phenyl-2-({[(1Z)-1-thien-2ylethylidene]amino}oxy)acetamide

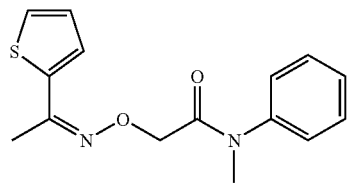

Compound 8: N-(2-Hydroxyethyl)-N-phenyl-2-({[(1Z)-1-thien-2-ylethylidene]amino}oxy)acetamide

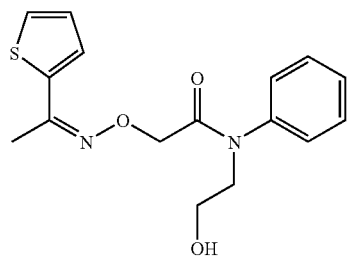

Cosmetic compositions can be formulated according to the methods described in examples 1-7 to 1-13 with the compounds of examples I to IV or those indicated herein.

Each patent, patent application, publication and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

```
                              SEQUENCE LISTING

<160> NUMBER OF SEQ ID NOS: 8

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
atggatgatg atatcgccgc gct                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cggactcgtc atactcctgc ttg                                              23

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ctcatagggg agaccatcaa g                                                21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccttctctcc tacgagctcc t                                                21

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgccaatgga ttgataacac tcat                                             24
```

```
<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
acagcagttt tcatctggga tatg                                              24

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggggatccat gcacgtgaac ggcaaagtg                                         29

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tctcgagagc tgttcattgg gt                                                22
```

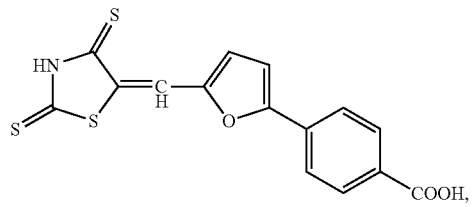

disodium salt of 4-{5-[(2,4-disulfo-1,3-thiazolidin-5-ylidene)methyl]-2-furyl}benzoic acid, and in particular the isomer in Z form- -continued
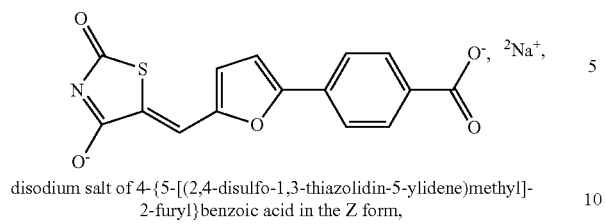
disodium salt of 4-{5-[(2,4-disulfo-1,3-thiazolidin-5-ylidene)methyl]-2-furyl}benzoic acid in the Z form,
Compound D1
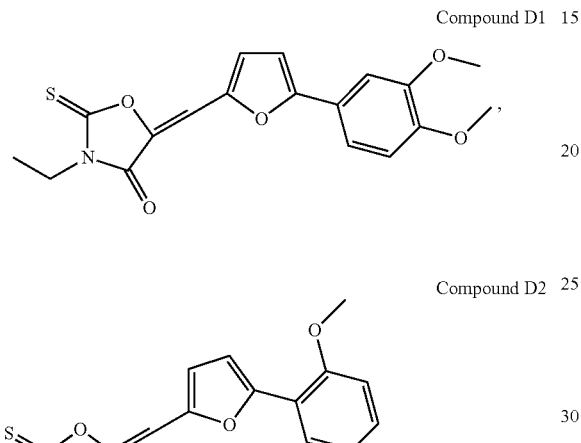
Compound D2
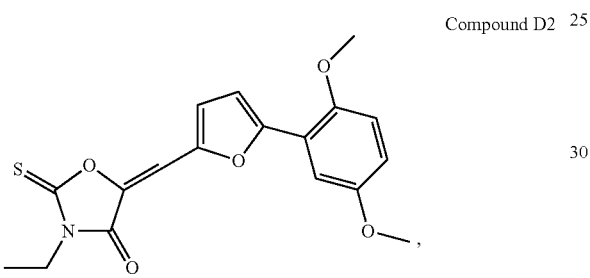
Compound D3
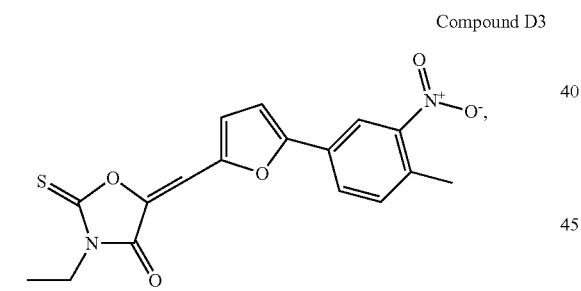
Compound E1
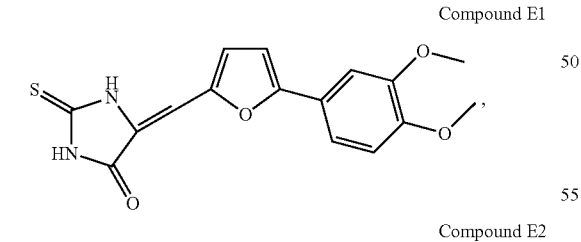
Compound E2
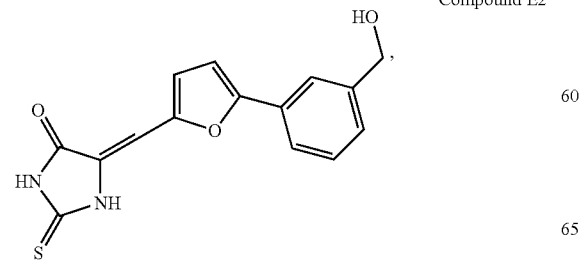
-continued
Compound E3
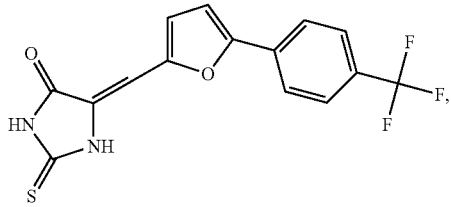
Compound E4
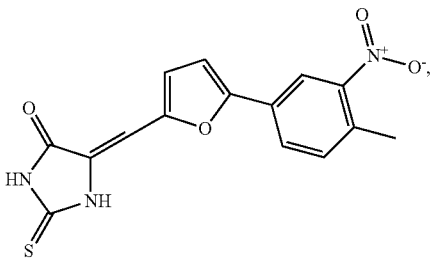
Compound E5
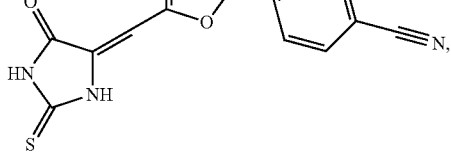
Compound E6
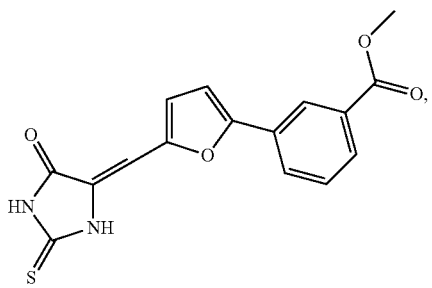
Compound E15
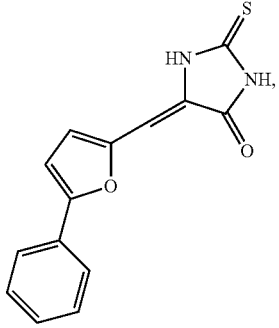
Compound F1
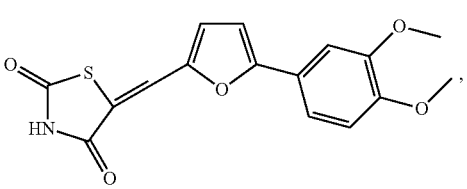

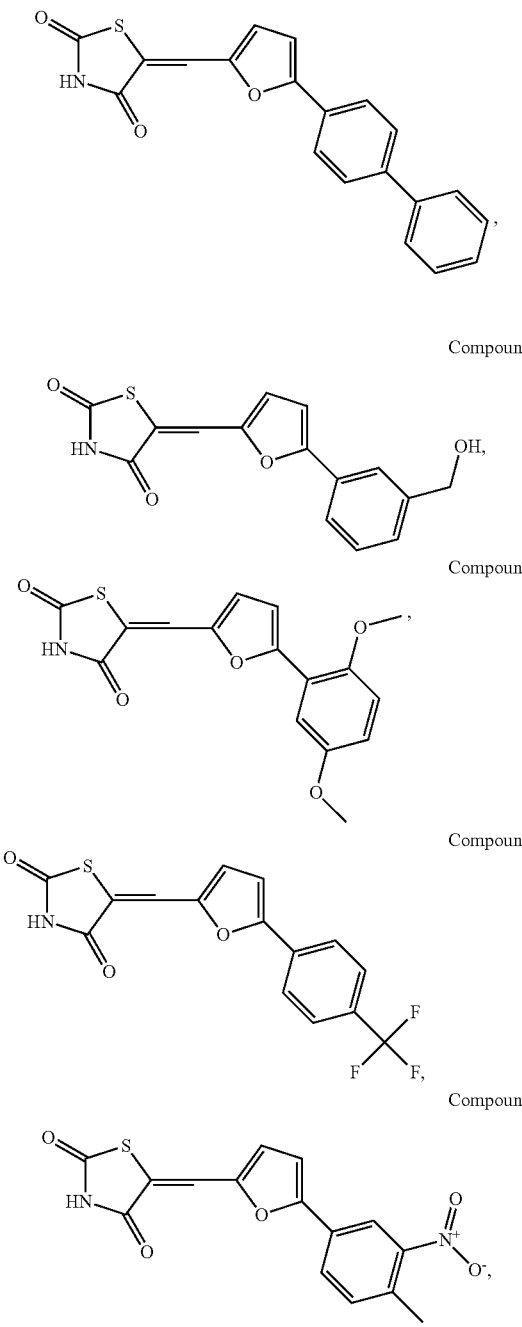

What is claimed is:

1. A regime or regimen for promoting or stimulating pigmentation of the skin and/or skin appendages and/or for limiting depigmentation and/or whitening of the skin and/or skin appendages, comprising administering to a mammalian organism in need of such treatment, a thus effective amount of at least one inhibitor of 15-hydroxyprostaglandin dehydrogenase (15-PGDH) of formula (I), or salt thereof:

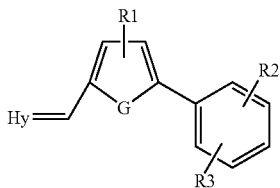

(I)

in which:

Hy is a heterocycle having 4, 5, 6 or 7 atoms, optionally comprising at least one carbonyl function and/or one thiocarbonyl function, said heterocycle being optionally substituted with at least one substituent selected from the group consisting of a halogen, the groups OR, SR, NRR', COR, CSR, NRCONR'R", C(=NR)R', C(=NR)NR'R", NRC(=NR')NR"R'", OCOR, COSR, SCOR, CSNRR', NRCSR', NRCSNR'R", COOR, CONRR', CF$_3$, CN, NRCOR', SO$_2$R', SO$_2$NRR' or NRSO$_2$R', saturated or unsaturated, linear or branched C$_1$-C$_{20}$ alkyl radicals, and saturated or unsaturated rings having 4 to 7 atoms, optionally containing at least one hetero atom, with the proviso that the alkyl radicals and the rings may be substituted, wherein R, R', R" and R'", which may be identical or different, are each a hydrogen, or a linear or branched C$_1$-C$_{20}$ alkyl radical or an aryl radical, that is optionally substituted;

G is O;

R$_1$, R$_2$ and R$_3$ represent, independently of one another, a hydrogen, a halogen, a group OR$_0$, SR$_0$, NR$_0$R'$_0$, COR$_0$, CSR$_0$, NR$_0$CONR'$_0$R"$_0$, C(=NR$_0$)R'$_0$, C(=NR$_0$)NR'$_0$R"$_0$, NR$_0$C(=NR'$_0$)NR"$_0$R'"$_0$, OCOR$_0$, COSR$_0$, SCOR$_0$, CSNR$_0$R'$_0$, NR$_0$CSR'$_0$, NR$_0$CSNR'$_0$R"$_0$, COOR$_0$, CONR$_0$R'$_0$, CF$_3$, NO$_2$, CN, NR$_0$COR'$_0$, SO$_2$R'$_0$, SO$_2$NR$_0$R'$_0$ or NR$_0$SO$_2$R'$_0$, a saturated or unsaturated, linear or branched C$_1$-C$_{20}$ alkyl radical, or at least one saturated or unsaturated ring having 4 to 7 atoms, optionally containing at least one hetero atom, with the proviso that the rings may be separated or attached, also with the proviso that the alkyl radicals and the rings may be substituted, wherein R$_0$, R'$_0$, R"$_0$ and R'"$_0$, which may identical or different, are each a hydrogen, or a linear or branched C$_1$-C$_{20}$ alkyl radical or an aryl radical, that is optionally substituted, wherein said inhibitor also has prostaglandin synthase-inhibiting activity, and the ratio of the 15-PGDH-inhibiting activity of said at least one inhibitor of 15-PGDH to the prostaglandin synthase-inhibiting activity thereof is greater than 1.

2. The regime or regimen as defined by claim 1, for limiting canities.

3. The regime or regimen as defined by claim 1, said at least one inhibitor of 15-PGDH being encapsulated in microspheres, nanospheres, oleosomes or nanocapsules.

4. The regime or regimen as defined by claim 1, said at least one inhibitor of 15-PGDH comprising an inhibitor specific for 15-PGDH type 1.

5. The regime or regimen as defined by claim 1, comprising topically applying said at least one inhibitor of 15-PGDH onto the skin, the head hair and/or body hair of said mammalian organism.

6. The regime or regimen as defined by claim 1, said ratio being at least 3:1.

7. The regime or regimen as defined by claim 1, said ratio being at least 5:1.

8. The regime or regimen as defined by claim 1, said ratio being at least 10:1.

9. The regime or regimen as defined by claim 1, said ratio being at least 15:1.

10. The regime or regimen as defined by claim 1, said ratio being at least 25:1.

11. A regime or regimen for stimulating the production of melanin by the melanocytes, comprising administering to a mammalian organism in need of such treatment, a thus effective amount of at least one inhibitor of 15-hydroxyprostaglandin dehydrogenase (15-PGDH) of formula (I), or salt thereof:

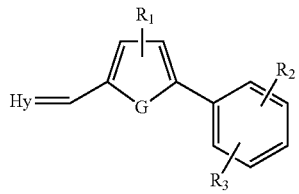

(I)

in which:
Hy is a heterocycle having 4, 5, 6 or 7 atoms, optionally comprising at least one carbonyl function and/or one thiocarbonyl function, said heterocycle being optionally substituted with at least one substituent selected from the group consisting of a halogen, the groups OR, SR, NRR', COR, CSR, NRCONR'R", C(=NR)R', C(=NR)NR'R", NRC(=NR')NR"R"', OCOR, COSR, SCOR, CSNRR', NRCSR', NRCSNR'R", COOR, CONRR', $CF_3$, CN, NRCOR', $SO_2R'$, $SO_2NRR'$ or $NRSO_2R'$ saturated or unsaturated, linear or branched $C_1$-$C_{20}$ alkyl radicals, and saturated or unsaturated rings having 4 to 7 atoms, optionally containing at least one hetero atom, with the proviso that the alkyl radicals and the rings may be substituted, wherein R, R', R" and R"', which may be identical or different, are each a hydrogen, or a linear or branched $C_1$-$C_{20}$ alkyl radical or an aryl radical, that is optionally substituted;

G is O;

$R_1$, $R_2$ and $R_3$ represent, independently of one another, a hydrogen, a halogen, a group $OR_0$, $SR_0$, $NR_0R'_0$, $COR_0$, $CSR_0$, $NR_0CONR'_0R"_0$, $C(=NR_0)R'_0$, $C(=NR_0)NR'_0R"_0$, $NR_0C(=NR'_0)NR"_0R"'_0$, $OCOR_0$, $COSR_0$, $SCOR_0$, $CSNR_0R'_0$, $NR_0CSR'_0$, $NR_0CSNR'_0R"_0$, $COOR_0$, $CONR_0R'_0$, $CF_3$, $NO_2$, CN, $NR_0COR'_0$, $SO_2R'_0$, $SO_2NR_0R'_0$ or $NR_0SO_2R'_0$, a saturated or unsaturated, linear or branched $C_1$-$C_{20}$ alkyl radical, or at least one saturated or unsaturated ring having 4 to 7 atoms, optionally containing at least one hetero atom, with the proviso that the rings may be separated or attached, also with the proviso that the alkyl radicals and the rings may be substituted, wherein $R_0$, $R'_0$, $R"_0$ and $R"'_0$, which may identical or different, are each a hydrogen, or a linear or branched $C_1$-$C_{20}$ alkyl radical or an aryl radical, that is optionally substituted, wherein said inhibitor also has prostaglandin synthase-inhibiting activity, and the ratio of the 15-PGDH-inhibiting activity of said at least one inhibitor of 15-PGDH to the prostaglandin synthase-inhibiting activity thereof is greater than 1.

12. The regime or regimen as defined by claim 1, comprising coadministering at least one active agent for promoting pigmentation of the head and/or body hair that is other than said at least one inhibitor of 15-PGDH.

13. The regime or regimen as defined by claim 1, comprising coadministering at least one penetration-accelerating agent.

14. The regime or regimen as defined by claim 1, comprising coadministering at least one prostaglandin or prostaglandin derivative.

15. A regime or regimen for promoting or stimulating pigmentation of the skin and/or skin appendages and/or for limiting depigmentation and/or whitening of the skin and/or skin appendages, comprising administering to a mammalian organism in need of such treatment, a thus effective amount of at least one inhibitor of 15-hydroxyprostaglandin dehydrogenase (15-PGDH), said at least one inhibitor of 15-PGDH comprising at least one heterocyclic compound of formula (I), or salt thereof:

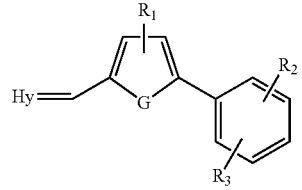

(I)

in which:
Hy is a heterocycle having 4, 5, 6 or 7 atoms, optionally comprising at least one carbonyl function and/or one thiocarbonyl function, said heterocycle being optionally substituted with at least one substituent selected from the group consisting of a halogen, the groups OR, SR, NRR', COR, CSR, NRCONR'R", C(=NR)R', C(=NR)NR'R", NRC(=NR')NR"R"', OCOR, COSR, SCOR, CSNRR', NRCSR', NRCSNR'R", COOR, CONRR', $CF_3$, CN, NRCOR', $SO_2R'$, $SO_2NRR'$ or $NRSO_2R'$ saturated or unsaturated, linear or branched $C_1$-$C_{20}$ alkyl radicals, and saturated or unsaturated rings having 4 to 7 atoms, optionally containing at least one hetero atom, with the proviso that the alkyl radicals and the rings may be substituted, wherein R, R', R" and R"', which may be identical or different, are each a hydrogen, or a linear or branched $C_1$-$C_{20}$ alkyl radical or an aryl radical, that is optionally substituted;

G is O;

$R_1$, $R_2$ and $R_3$ represent, independently of one another, a hydrogen, a halogen, a group $OR_0$, $SR_0$, $NR_0R'_0$, $COR_0$, $CSR_0$, $NR_0CONR'_0R"_0$, $C(=NR_0)R'_0$, $C(=NR_0)NR'_0R"_0$, $NR_0C(=NR'_0)NR"_0R"'_0$, $OCOR_0$, $COSR_0$, $SCOR_0$, $CSNR_0R'_0$, $NR_0CSR'_0$, $NR_0CSNR'_0R"_0$, $COOR_0$, $CONRR'_0$, $CF_3$, $NO_2$, $CN$, $NR_0COR'_0$, $SO_2R'_0$, $SO_2NR_0R'_0$ or $NR_0SO_2R'_0$, a saturated or unsaturated, linear or branched $C_1$-$C_{20}$ alkyl radical, or at least one saturated or unsaturated ring having 4 to 7 atoms, optionally containing at least one hetero atom, with the proviso that the rings may be separated or attached, also with the proviso that the alkyl radicals and the rings may be substituted, wherein $R_0$, $R'_0$, $R''_0$ and $R'''_0$, which may identical or different, are each a hydrogen, or a linear or branched $C_1$-$C_{20}$ alkyl radical or an aryl radical, that is optionally substituted.

16. A regime or regimen for promoting or stimulating pigmentation of the skin and/or skin appendages and/or for limiting depigmentation and/or whitening of the skin and/or skin appendages, comprising administering to a mammalian organism in need of such treatment, a thus effective amount of at least one inhibitor of 15-hydroxyprostaglandin dehydrogenase (15-PGDH) of formula (I), or salt thereof:

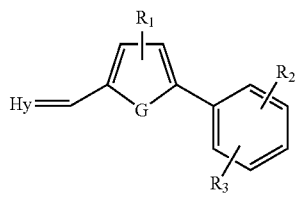

(I)

in which:
Hy is a heterocycle having 4, 5, 6 or 7 atoms, optionally comprising at least one carbonyl function and/or one thiocarbonyl function, said heterocycle being optionally substituted with at least one substituent selected from the group consisting of a halogen, the groups OR, SR, NRR', COR, CSR, NRCONR'R'', C(=NR)R', C(=NR)NR'R'', NRC(=NR')NR''R''', OCOR, COSR, SCOR, CSNRR', NRCSR', NRCSNR'R'', COOR, CONRR', $CF_3$, CN, NRCOR', $SO_2R'$, $SO_2NRR'$ or $NRSO_2R'$ saturated or unsaturated, linear or branched $C_1$-$C_{20}$ alkyl radicals, and saturated or unsaturated rings having 4 to 7 atoms, optionally containing at least one hetero atom, with the proviso that the alkyl radicals and the rings may be substituted, wherein R, R', R'' and R''', which may be identical or different, are each a hydrogen, or a linear or branched $C_1$-$C_{20}$ alkyl radical or an aryl radical, that is optionally substituted;

G is O;

$R_1$, $R_2$ and $R_3$ represent, independently of one another, a hydrogen, a halogen, a group $OR_0$, $SR_0$, $NR_0R'_0$, $COR_0$, $CSR_0$, $NR_0CONR'_0R''_0$, $C(=NR_0)R'_0$, $C(=NR_0)NR'_0R''_0$, $NR_0C(=NR'_0)NR''_0R'''_0$, $OCOR_0$, $COSR_0$, $SCOR_0$, $CSNR_0R'_0$, $NR_0CSR'_0$, $NR_0CSNR'_0R''_0$, $COOR_0$, $CONR_0R'_0$, $CF_3$, $NO_2$, $CN$, $NR_0COR'_0$, $SO_2R'_0$, $SO_2NR_0R'_0$ or $NR_0SO_2R'_0$, a saturated or unsaturated, linear or branched $C_1$-$C_{20}$ alkyl radical, or at least one saturated or unsaturated ring having 4 to 7 atoms, optionally containing at least one hetero atom, with the proviso that the rings may be separated or attached, also with the proviso that the alkyl radicals and the rings may be substituted, wherein $R_0$, $R'_0$, $R''_0$ and $R'''_0$, which may identical or different, are each a hydrogen, or a linear or branched $C_1$-$C_{20}$ alkyl radical or an aryl radical, that is optionally substituted, and co-administering at least one prostaglandin or prostaglandin derivative, said at least one prostaglandin or derivative thereof being selected from the group consisting of prostaglandin PGE1, PGE2, the salts and esters thereof, analogs and derivatives thereof, prostaglandin F2-alpha receptor (FP-R) agonists, latanoprost, fluprostenol, cloprostenol, travoprost or bimatoprost, prostaglandin E2 receptor (EP1-R, EP2-R, EP3-R, EP4-R) agonists, 17-phenyl PGE2, viprostol, butaprost, misoprostol, sulprostone, 16,16-dimethyl PGE2, 11-deoxy-PGE1 or 1-deoxy-PGE1, prostacyclin (IP) receptor agonists and esters thereof, cicaprost, iloprost, isocarbacycline or beraprost, prostaglandin D2 receptor agonists and esters thereof, BW245C ((4S)-(3-[(3R,S)-3-cyclohexyl-3-isopropyl]-2,5-dioxo)4-imidazolidineheptanoic acid) or ((4R)-(3-[(3R,S)-3-cyclohexyl-3-isopropyl]-2,5-dioxo)-4-imidazolidine-heptanoic acid), or thromboxane A2 (TP) receptor agonists, I-BOP ([1S-[1a,2a(Z),3b( 1E, 3S),4a]]-7-[3-[3-hydroxy-4-[4-(iodophenoxy)- 1-butenyl]-7-oxabicyclo[2.2.1]hept-2-yl]-5-heptenoic acid, precursors of these compounds and esters and derivatives thereof.

17. The regime or regimen as defined by claim 1, said at least one inhibitor of 15-PGDH comprising PhCL28A or a thiazolidinedione.

18. A cosmetic/dermatological composition suited for promoting or stimulating pigmentation of the skin and/or skin appendages and/or for limiting depigmentation and/or whitening of the skin and/or skin appendages, comprising a thus effective amount of at least one inhibitor of 15-PGDH of formula (I), or salt thereof:

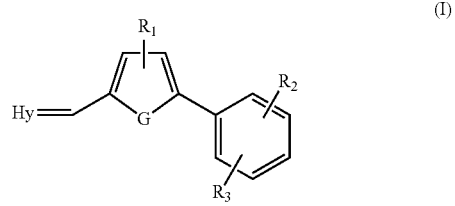

(I)

in which:
Hy is a heterocycle having 4, 5, 6 or 7 atoms, optionally comprising at least one carbonyl function and/or one thiocarbonyl function, said heterocycle being optionally substituted with at least one substituent selected from the group consisting of a halogen, the groups OR, SR, NRR', COR, CSR, NRCONR'R'', C(=NR)R', C(=NR)NR'R'', NRC(=NR')NR''R''', OCOR, COSR, SCOR, CSNRR', NRCSR', NRCSNR'R'', COOR, CONRR', $CF_3$, CN, NRCOR', $SO_2R'$, $SO_2NRR'$ or $NRSO_2R'$ saturated or unsaturated, linear or branched $C_1$-$C_{20}$ alkyl radicals, and saturated or unsaturated rings having 4 to 7 atoms, optionally containing at least one hetero atom, with the proviso that the alkyl radicals and the rings may be substituted, wherein R, R', R'' and R''', which may be identical or different, are each a hydrogen, or a linear or branched $C_1$-$C_{20}$ alkyl radical or an aryl radical, that is optionally substituted;

G is O;

$R_1$, $R_2$ and $R_3$ represent, independently of one another, a hydrogen, a halogen, a group $OR_0$, $SR_0$, $NR_0R'_0$, $COR_0$, $CSR_0$, $NR_0CONR'_0R''_0$, $C(=NR_0)R'_0$, $C(=NR_0)$ NR'₀R"₀, NR₀C(=NR'₀)NR"₀R'"₀, OCOR₀, COSR₀, SCOR₀, CSNR₀R'₀, NR₀CSR'₀,NR₀CSNR'₀R"₀, COOR₀, CONR₀R'₀, CF₃, NO₂, CN, NR₀COR'₀, SO₂R'₀, SO₂NR₀R'₀ or NR₀SO₂R'₀, a saturated or unsaturated, linear or branched C₁-C₂₀ alkyl radical, or at least one saturated or unsaturated ring having 4 to 7 atoms, optionally containing at least one hetero atom, with the proviso that the rings may be separated or attached, also with the proviso that the alkyl radicals and the rings may be substituted, wherein R₀, R'₀, R"₀and R'"₀, which may identical or different, are each a hydrogen, or a linear or branched C₁-C₂₀ alkyl radical or an aryl radical, that is optionally substituted, formulated into a cosmetically/dermatologically acceptable medium therefor, wherein said inhibitor also has prostaglandin synthase-inhibiting activity, and the ratio of the 15-PGDH-inhibiting activity of said at least one inhibitor of 15-PGDH to the prostaglandin synthase-inhibiting activity thereof is greater than 1.

19. The cosmetic/dermatological composition as defined by claim 18, said at least one inhibitor of 15-PGDH comprising a tetrazole, styrylpyrazole, phenylfuran, phenylthiophene, phenylpyrrazole, pyrazolecarboxamide, thioacetamide and/or azo compound.

20. The cosmetic/dermatological composition as defined by claim 19, said at least one inhibitor of 15-PGDH being encapsulated in microspheres, nanospheres, oleosomes or nanocapsules.

21. The cosmetic/dermatological composition as defined by claim 19, further comprising at least one prostaglandin or prostaglandin derivative.

22. The cosmetic/dermatological composition as defined by claim 19, further comprising at least one active agent for promoting pigmentation of the head and/or body hair that is other than said at least one inhibitor of 15-PGDH.

23. The cosmetic/dermatological composition as defined by claim 19, said at least one inhibitor of 15-PGDH being formulated into a topically applicable, cosmetically/dermatologically acceptable medium therefor.

24. The cosmetic/dermatological composition as defined by claim 19, formulated as a lotion, gel, emulsion, cream, serum, powder, salve, tincture, milk, ointment, spray, shampoo, mascara, foam, syrup, capsules, granules, tablets or conditioner.

25. The regime or regimen of claim 15, wherein said at least one inhibitor of 15-PGDH comprises at least one heterocyclic compound selected from the group consisting of:

4-{5-[(2,4-dioxo-1,3-thiazolidin-5-ylidene)methyl]-2-furyl}benzoic acid—

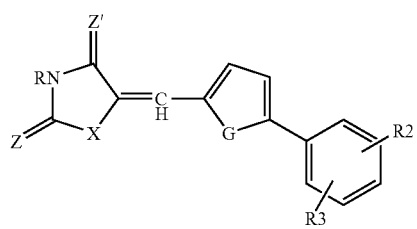

Compound 1a

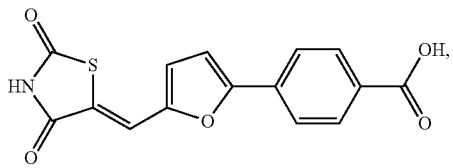

ethyl 4-{5-[(2,4-dioxo-1,3-thiazolidin-5-ylidene)methyl]-2-furyl}benzoate-

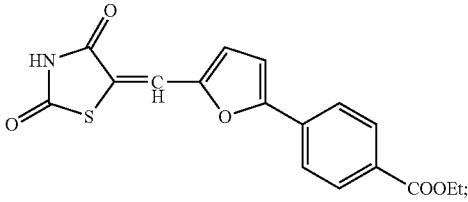

5-({5-[3,5-bis(trifluoromethyl)phenyl]-2-furyl}methylene-1,3-thiazolidene-2,4-dione-

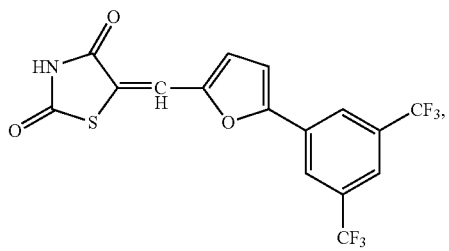

3-{5-[(2,4-dioxo-1,3-thiazolidin-5-ylidene)methyl]-2-furyl}benzoic acid-

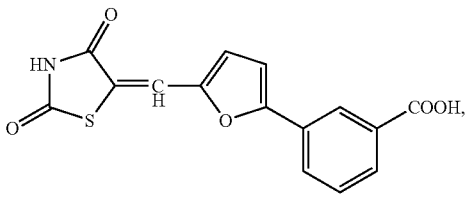

4{5-[(2-sulfo-4-oxo-1,3-thiazolidin-5-ylidene)methyl]-2-furyl}benzoic acid-

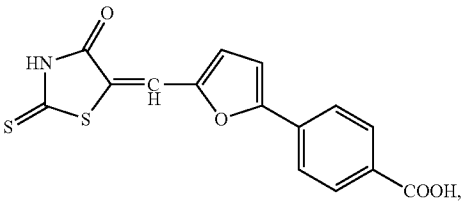

4-{5-[(2,4-disulfo-1,3-thiazolidin-5-ylidene)methyl]-2-furyl}benzoic acid-